(12) United States Patent
Dudash et al.

(10) Patent No.: US 8,796,313 B2
(45) Date of Patent: Aug. 5, 2014

(54) SUBSTITUTED DIHYDROISOINDOLONES AS ALLOSTERIC MODULATORS OF GLUCOKINASE

(75) Inventors: Joseph Dudash, Hillsborough, NJ (US); Philip Rybczynski, Somerville, NJ (US); Maud Urbanski, Flemington, NJ (US); Amy Xiang, Bridgewater, NJ (US); Roxanne Zeck, Whitehouse Station, NJ (US); Xiaoyan Zhang, Belle Mead, NJ (US); Yongzheng Zhang, Hillsborough, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 1016 days.

(21) Appl. No.: 11/554,500

(22) Filed: Oct. 30, 2006

(65) Prior Publication Data
US 2007/0099930 A1    May 3, 2007

Related U.S. Application Data

(60) Provisional application No. 60/732,370, filed on Nov. 1, 2005.

(51) Int. Cl.
*A61K 31/4439* (2006.01)
*C07D 401/12* (2006.01)

(52) U.S. Cl.
USPC ........................................ 514/339; 546/277.1

(58) Field of Classification Search
USPC ........................................ 546/277.1; 514/339
See application file for complete search history.

(56) References Cited

U.S. PATENT DOCUMENTS 7,521,451 B2 *    4/2009    Toyooka et al. ............... 514/247

FOREIGN PATENT DOCUMENTS

| EP | 1566378 A1 | 8/2005 |
|---|---|---|
| WO | WO 98/35957 A1 | 8/1998 |
| WO | WO 01/16122 A1 | 3/2001 |
| WO | WO 01/16123 A1 | 3/2001 |
| WO | WO 02/48106 A2 | 6/2002 |
| WO | WO 03/055482 A1 | 7/2003 |
| WO | WO 2004/041813 A1 | 5/2004 |
| WO | WO 2005/095418 A1 | 10/2005 |

OTHER PUBLICATIONS

Balant et al., "Metabolic Considerations, etc.," in Manfred ed. Burger's Medicinal Chemistry and Drug Discovery, 5th ed. vol. 1:Principles and Practice, John Wiley & Sons, Inc., 1995.*
Lowney, V. K. Obesity *Decision Resources Inc.* Mosaic Study #20, 2000.
Connolly et al., "Valvular Heart Disease Associated With Fenfluramine-Phentermine.", N. Engl. J. Med., Aug. 28, 1997, vol. 337(9), pp. 581-588.
Gould P.L., "Salt Selection for Basic Drugs.", International J. Pharm., 1986, vol. 33, pp. 201-217.
Berge et al., "Pharmaceutical Salts.", J. Pharm. Sci., 1977, vol. 66(1), pp. 1-19.
Epsztajn et al., "Application of Organolithium and Related Reagents in Synthesis. Part 13. Synthetic Strategies based on Aromatic Metallation. A Concise Regiospecific Conversion of Benzoic Acids Into 4-Hydroxy-l-Arylnaphthaelenes.", Tetrahedron, 1993, vol. 49(4), pp. 929-938, Great Britain, Pergamon Press, Ltd.
Chihab-Eddine et al., "Studies on (1S)-N-(1-phenylethyl)phthalimide: Synthesis of both chiral spiro indane and benzazepine derivative.", Heterocycles, Nov. 22, 2002, vol. 58, pp. 449-456.
Luzzio et al., "Alkylation and Annulation of 3-(Phenylsulfonyl)-2,3-Dihydroisoindol-1-ones.", Tetrahedron Letters, 1998, vol. 39, pp. 2285-2288, Elsevier Science Ltd.
Grimsby et al., "Allosteric Activators of Glucokinase: Potential Role in Diabetes Therapy.", Science, Jul. 18, 2003, vol. 301, pp. 370-373.
PCT International Search Report No. PCT/US2006/042188 dated Apr. 2, 2007, which relates to U.S. Appl. No. 11/554,500.

* cited by examiner

*Primary Examiner* — Patricia L Morris
(74) *Attorney, Agent, or Firm* — Jeremy K. McKown

(57) ABSTRACT

The present invention relates to compounds of Formula (I),

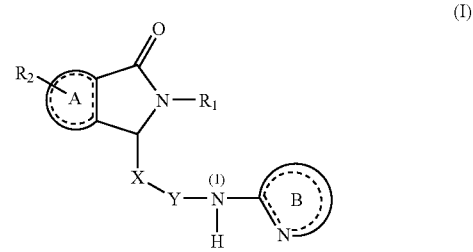

methods for preparing these compounds, compositions, intermediates and derivatives thereof and for treating glucokinase mediated disorders. More particularly, the compounds of the present invention are glucokinase modulators useful for treating disorders including, but not limited to, type II diabetes.

17 Claims, No Drawings

SUBSTITUTED DIHYDROISOINDOLONES AS ALLOSTERIC MODULATORS OF GLUCOKINASE

CROSS REFERENCE TO RELATED APPLICATION

This application claims the benefit of U.S. provisional application Ser. No. 60/732,370 filed Nov. 1, 2005, which is incorporated by reference herein.

FIELD OF THE INVENTION

The present invention relates to certain novel compounds, methods for preparing compounds, compositions, intermediates and derivatives thereof and for treating metabolic disorders. More particularly, the compounds of the present invention are glucokinase modulators useful for treating, ameliorating or inhibiting the onset of metabolic disorders such as diabetes and obesity.

BACKGROUND OF THE INVENTION

Diabetes is a chronic disorder affecting carbohydrate, fat and protein metabolism in animals.

Type I diabetes mellitus, which comprises approximately 10% of all diabetes cases, was previously referred to as insulin-dependent diabetes mellitus ("IDDM") or juvenile-onset diabetes. This disease is characterized by a progressive loss of insulin secretory function by beta cells of the pancreas. This characteristic is also shared by non-idiopathic, or "secondary," diabetes having its origins in pancreatic disease. Type I diabetes mellitus is associated with the following clinical signs or symptoms: persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Type II diabetes mellitus (non-insulin-dependent diabetes mellitus or "NIDDM") is a metabolic disorder involving the dysregulation of glucose metabolism and impaired insulin sensitivity. Type II diabetes mellitus usually develops in adulthood and is associated with the body's inability to utilize or make sufficient insulin. In addition to the insulin resistance observed in the target tissues, patients suffering from the late-stage type II diabetes mellitus have a relative insulin insensitivity—that is patients have higher than predicted insulin levels for a given plasma glucose concentration. Type II diabetes mellitus is characterized by the following clinical signs or symptoms: persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Obesity is rapidly becoming a major health crisis in developed countries as well as some regions of developing countries. The available evidence indicates that the prevalence of obesity in adults and children is growing at an alarming pace. In the developed world, estimates for 1999 suggest that the number of obese adults was approximately 88 million and growing at an annual rate of 2.8% (Decision Resources Report (2000), *Mosaic/Obesity* 20: 1-126). Obesity is believed to cause or exacerbate many health complications and social problems such as coronary heart disease, stroke, obstructive sleep apnea, gout, hyperlipidemia, osteoarthritis, reduced fertility, and impaired psychosocial function.

The widely held view that obesity is the result of a lack of self-control is slowly changing. Physicians are beginning to perceive obesity as a serious condition caused by a variety of complex messages involving signals for hunger, satiety, and determinants of energy consumption. It is now recognized that factors such as specific environmental cues, cultural norms, and genetic predisposition all contribute to excessive weight gain. The two major objectives for obesity treatment include a modest weight loss followed by appropriate weight maintenance, with the ultimate goal of reducing morbidity and mortality. A 5-10% reduction in body weight has been shown to produce clinically significant improvements in blood pressure, cholesterol, and blood glucose levels. General practitioners commonly cite three concerns with the existing treatments for obesity. These concerns include 1) the limited efficacy of current therapies, 2) poor side-effect profiles, and 3) non-compliance due to high cost of medication. Although obesity researchers have made great strides in understanding the fundamental causes of obesity, much remains to be done in the search for therapies with 1) increased efficacy, 2) better safety profiles, 3) lower cost, and 4) improved patient compliance.

Several products have been approved for treatment of obesity in the United States, such as the anorectic agent dexfenfluramine (d-FF or REDUX™) and fenfluramine, both 5-HT reuptake inhibitors, and the antiobesity agent sibutramine (MERIDIA™), a serotonin and noradrenaline uptake inhibitor. However, dexfenfluramine and fenfluramine were withdrawn from marketing on the basis of the reports that these drugs, when used in combination with phentermine, an anti-obesity agent that increases extraneuronal norepinephrine by enhancing its release, result in conditions including pulmonary hypertension and valvular heart disease (Connolly, H. M, Crary, J. M., McGoon, M. D. et al. Valvular heart disease associated with fenfluramine-phentermine. N. Engl. J. Med. (1997) 337:581-588). On the other hand, sibutramine, which reduces appetite, is only used by a small fraction of eligible obese patients due to the belief that anti-obesity drugs are unsafe. Thus, approved drugs for the treatment of a disorder that affects many millions are only moderately successful because of their widely recognized shortcomings.

Glucokinase ("GK" or "GLK") is a rate-limiting enzyme that catalyzes the conversion of glucose to glucose-6-phosphate, the first step in glucose metabolism. It is expressed in the pancreatic β-cells and hepatocytes, both of which are known to play critical roles in whole-body blood glucose homeostasis. The compounds of this invention act as glucokinase modulators. A modulator that raises the enzyme's affinity for glucose ($K_m$) and its velocity ($V_{max}$) would increase the flux of glucose metabolism in both cell types. Since pancreatic glucokinase modulation is coupled with an increase in insulin secretion, a modulator would be useful for the treatment of diabetes such as type II diabetes.

There is a continuing need for new glucokinase modulators. There is also a need for glucokinase modulators useful for the treatment of conditions including but not limited to metabolic disorders such as diabetes and obesity.

SUMMARY OF THE INVENTION

In its many embodiments, the present invention provides a novel class of compounds useful as, for example, glucokinase modulators, methods of preparing such compounds, pharmaceutical compositions comprising one or more such compounds, methods of preparing pharmaceutical compositions comprising one or more such compounds, and methods of treatment, prevention, inhibition or amelioration of one or more diseases associated with glucokinase using such compounds or pharmaceutical compositions.

One aspect of the present invention features a compound of Formula (I)

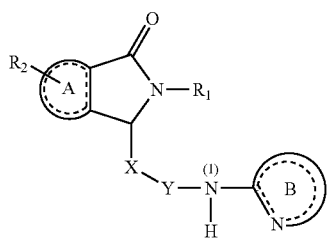

wherein $R_1$ is H or $C_{1-6}$alkyl optionally substituted with optionally substituted aryl, optionally substituted heteroaryl, or optionally substituted heterocyclyl;

$R_2$ is 0-3 members independently selected from halo, —$OR_4$, —$SR_4$, —$SO_2$—$R_4$, carboxy, nitro, hydroxyl, amido, optionally substituted $C_{1-6}$alkyl, optionally substituted $C_{2-6}$alkenyl, optionally substituted $C_{2-6}$alkynyl, and amino optionally substituted with optionally substituted $C_{1-6}$alkyl, optionally substituted aryl, optionally substituted $C_{5-6}$heteroaryl, or optionally substituted $C_{5-8}$heterocyclyl, wherein $R_4$ is selected from H, $C_{1-6}$alkyl, aryl, heteroaryl, and heterocyclyl;

A is aryl or heteroaryl;

B is heteroaryl or heterocyclyl, said heteroaryl being connected to N(1) through a ring carbon atom adjacent to a ring nitrogen, said heterocyclyl being connected to N(1) through a carbon atom that is double-bonded to a ring nitrogen, and additionally said heteroaryl and heterocyclyl having an additional 0 to 3 heteroatoms selected from O, S, and N, wherein one or more ring nitrogen atoms in said heteroaryl or heterocyclyl can be optionally in an N-oxide form, and said heteroaryl or heterocyclyl being further optionally substituted with 1 or 2 members selected from optionally substituted $C_{1-4}$alkyl, optionally substituted $C_{2-4}$alkenyl, halo, —CN, aryl, heteroaryl, heterocyclyl, —$SO_3H$, —C(O)OH, —C(O)O—$C_{1-4}$alkyl, —$OR_4$, —$SR_4$, —C(O)$R_4$, —N($R_4$)($R_5$), —C(O)—N($R_4$)($R_5$), —$SO_2$—$R_4$, and —$SO_2$—N($R_4$)($R_5$), wherein $R_4$ and $R_5$ are independently selected from H, $C_{1-6}$alkyl, aryl, heteroaryl, and heterocyclyl;

X is optionally substituted $C_{1-3}$alkylene; and

Y is —O—C(O)—, —N(H)—C(O)—, —C(O)—, or —S(O)$_2$—, wherein said C(O) functionality is adjacent to N(1);

or an optical isomer, enantiomer, diastereomer, racemate, prodrug or pharmaceutically acceptable salt thereof.

Another aspect of the present invention features a pharmaceutical composition comprising at least one compound of Formula (I) and at least one pharmaceutically acceptable carrier.

One embodiment of the invention is a method for treating or ameliorating a glucokinase-mediated condition in a subject in need thereof comprising administering to the subject a therapeutically effective amount of at least one compound of Formula (I). Particularly, it is an embodiment of the invention to provide a method for treating or ameliorating a condition selected from diabetes, obesity, and associated symptoms or complications thereof in a subject in need thereof, comprising administering to said subject a therapeutically effective amount of (a) at least one compound of Formula (I); and (b) at least one additional agent selected from an anti-diabetic agent, a lipid lowering agent, an anti-thrombotic agent, and a blood pressure lowering agent, said co-administration being in any order. In one embodiment the additional agent is a glucokinase modulator.

Another embodiment of the invention is a method for preventing or inhibiting the onset of a glucokinase-mediated condition in a subject in need thereof, comprising administering to said subject a therapeutically effective amount of (a) at least one compound of Formula (I); and (b) at least one additional agent selected from an anti-diabetic agent, a lipid lowering agent, an anti-thrombotic agent, and a blood pressure lowering agent, said co-administration being in any order and the combined amounts providing the desired prophylactic effect. In one embodiment the additional agent is also a glucokinase modulator.

It is a further embodiment of the invention to provide a process for making a pharmaceutical composition comprising admixing any of the compounds according to Formula (I) and a pharmaceutically acceptable carrier.

Another embodiment of the invention is a method for treating or ameliorating glucokinase-mediated diseases such as diabetes ((including, but not limited to IDDM, NIDDM, IGT (Impaired Glucose Tolerance), IFG (Impaired Fasting Glucose)), obesity, and Syndrome X (or Metabolic Syndrome). A further embodiment of the invention is a method for treating or ameliorating the associated symptoms or complications of diabetes, obesity and/or Syndrome X, including, but not limited to hyperglycemia, elevated blood glucose level, and insulin resistance.

Additional embodiments and advantages of the invention will become apparent from the detailed discussion, examples, and claims below.

DETAILED DESCRIPTION OF THE INVENTION

This invention relates to novel glucokinase modulators and compositions thereof for treatment or prophylaxis of conditions such as diabetes, obesity, and associated symptoms or complications thereof.

One aspect of the present invention features a compound of Formula (I)

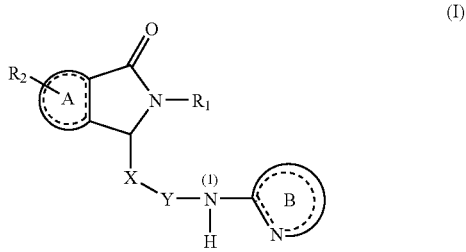

wherein $R_1$ is H or $C_{1-6}$alkyl optionally substituted with optionally substituted aryl, optionally substituted heteroaryl, or optionally substituted heterocyclyl;

$R_2$ is 0-3 members independently selected from halo, —$OR_4$, —$SR_4$, —$SO_2$—$R_4$, carboxy, nitro, hydroxyl, amido, optionally substituted $C_{1-6}$alkyl, optionally substituted $C_{2-6}$alkenyl, optionally substituted $C_{2-6}$alkynyl, and amino optionally substituted with optionally substituted $C_{1-6}$alkyl, optionally substituted aryl, optionally substituted heteroaryl, or optionally substituted $C_{5-8}$heterocyclyl, wherein $R_4$ is selected from H, $C_{1-6}$alkyl, aryl, heteroaryl, and heterocyclyl;

A is aryl or heteroaryl;

B is heteroaryl or heterocyclyl, said heteroaryl being connected to N(1) through a carbon atom adjacent to a ring nitrogen, said heterocyclyl being connected to N(1) through a ring carbon atom that is double-bonded to a ring nitrogen, and additionally said heteroaryl and heterocyclyl having an additional 0 to 3 heteroatoms selected from O, S, and N, wherein one or more ring nitrogen atoms in said heteroaryl or heterocyclyl can be optionally in an N-oxide form, and said heteroaryl or heterocyclyl being further optionally substituted with 1 or 2 members selected from optionally substituted $C_{1-4}$alkyl, optionally substituted $C_{2-4}$alkenyl, halo, —CN, aryl, heteroaryl, heterocyclyl, —SO$_3$H, —C(O)OH, —C(O)O—$C_{1-4}$alkyl, —OR$_4$, —SR$_4$, —C(O)R$_4$, —N(R$_4$)(R$_5$), —C(O)—N(R$_4$)(R$_5$), —SO$_2$—R$_4$, and —SO$_2$—N(R$_4$)(R$_5$), wherein R$_4$ and R$_5$ are independently selected from H, $C_{1-6}$alkyl, aryl, heteroaryl, and heterocyclyl;

X is optionally substituted $C_{1-3}$alkylene; and

Y is —O—C(O)—, —N(H)—C(O)—, —C(O)—, or —S(O)$_2$—, wherein said C(O) functionality is to N(1);

or an optical isomer, enantiomer, diastereomer, racemate, prodrug or pharmaceutically acceptable salt thereof.

In particular, the present invention features a compound of Formula (I) wherein $R_1$ is $C_{1-6}$alkyl optionally substituted with optionally substituted $C_6$aryl or $C_{10}$aryl;

$R_2$ is 0-2 members independently selected from halo;

A is $C_6$aryl or $C_{10}$aryl;

B is heteroaryl or heterocyclyl, said heteroaryl being connected to N(1) through a ring carbon atom adjacent to a ring nitrogen, said heterocyclyl being connected to N(1) through a carbon atom that is double-bonded to a ring nitrogen, and additionally said heteroaryl and heterocyclyl having 0 to 2 heteroatoms selected from S and N, wherein one or more ring nitrogen atoms in said heteroaryl or heterocyclyl can be optionally in an N-oxide form, and said heteroaryl or heterocyclyl being further optionally substituted with 1 or 2 members selected from optionally substituted $C_{1-4}$alkyl, optionally substituted $C_{2-4}$alkenyl, halo, —CN, optionally substituted $C_{6-10}$aryl, —C(O)OH, —C(O)O—$C_{1-4}$alkyl, —OR$_4$, —C(O)R$_4$, —S(O)$_2$—R$_4$, and —S(O)$_2$—N(R$_4$)(R$_5$), wherein R$_4$ and R$_5$ are independently selected from H, $C_{1-6}$alkyl, aryl, heteroaryl, and heterocyclyl;

X is optionally substituted $C_{1-3}$alkylene; and

Y is —O—C(O)—, —N(H)—C(O)—, —C(O)—, or —S(O)$_2$— wherein said C(O) functionality is adjacent to N(1);

or an optical isomer, enantiomer, diastereomer, racemate, prodrug or pharmaceutically acceptable salt thereof.

Particularly, the present invention features a compound of Formula (I) wherein $R_1$ is $C_{1-6}$alkyl substituted with optionally substituted aryl. More particularly, $R_1$ is methyl substituted with phenyl, said phenyl being optionally substituted with halo, methoxy, dimethoxy, dimethylamino, or pyrrolyl.

Particularly, the present invention features a compound of Formula (I) wherein $R_2$ is 0-2 members independently selected from F and Cl.

Particularly, the present invention features a compound of Formula (I) wherein A is phenyl.

Particularly, the present invention features a compound of Formula (I) wherein B is heteroaryl having 1-2 nitrogen atoms. Particularly, the present invention features a compound of Formula (I) wherein B is an optionally substituted heteroaryl selected from

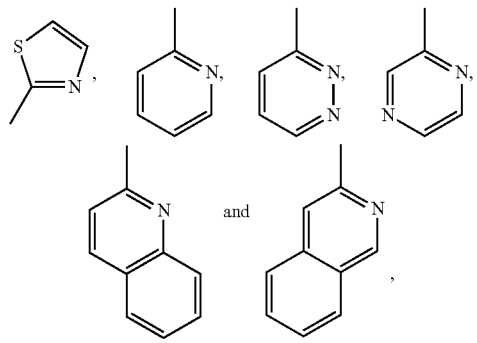

More particularly, one or more ring nitrogen atoms may optionally be in an N-oxide form. Specifically, an embodiment of the present invention is

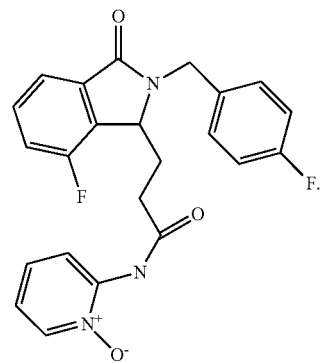 [SMILES: O=C(CCC1c2c(F)cccc2C(=O)N1Cc1ccc(F)cc1)Nc1cccc[n+]1[O-]]

Particularly, B is substituted with 0-2 members selected from halo, $C_{1-4}$alkyl, substituted $C_{1-4}$alkyl, aryl, substituted aryl, —C(O)OH, —C(O)R$_4$, —C(O)O—$C_{1-4}$alkyl, and —SO$_2$—N(R$_4$)(R$_5$), wherein R$_4$ and R$_5$ are as described above. In particular, B is substituted with 0-2 members selected from F, Br, —CH$_3$, —CF$_3$, —CH$_2$—C(O)OH, —C(O)—CH$_3$, —CH$_2$—O—CH$_2$—O—CH$_3$, unsubstituted phenyl, halo substituted aryl, —C(O)OH, —C(O)O—CH$_3$, —C(O)O—CH$_2$—CH$_3$, and —SO$_2$—NH$_2$.

Particularly, the present invention features a compound of Formula (I) wherein X is unsubstituted $C_{1-3}$alkylene.

Particularly, the present invention features a compound of Formula (I) wherein Y is —O—C(O)—.

Particularly, the present invention features a compound of Formula (I) wherein Y is —N(H)—C(O)—.

Particularly, the present invention features a compound of Formula (I) wherein Y is —C(O)—.

Particularly, the present invention features a compound of Formula (I) wherein Y is —S(O)$_2$—.

More particularly, the present invention features a compound of Formula (I) wherein $R_1$ is methyl substituted with phenyl, said phenyl being optionally substituted with halo, methoxy, dimethoxy, or pyrrolyl;

$R_2$ is 0-2 members independently selected from F and Cl;

A is phenyl;

B is an optionally substituted member selected from

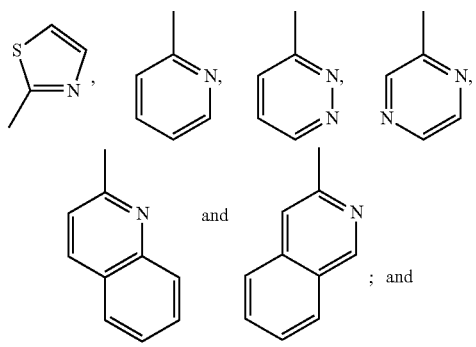

X is —CH₂— or —CH₂—CH₂—.

In particular, B is substituted with 0-2 members selected from halo, $C_{1-4}$alkyl, substituted $C_{1-4}$alkyl, aryl, substituted aryl, —C(O)OH, —C(O)R₄, —C(O)O—$C_{1-4}$alkyl, and —SO₂—N(R₄)(R₅), wherein R₄ and R₅ are as described above. More particularly, B is substituted with 0-2 members selected from F, Br, —CH₃, —CF₃, —CH₂—C(O)OH, —C(O)—CH₃, —CH₂—O—CH₂—O—CH₃, unsubstituted phenyl, halo substituted aryl, —C(O)OH, —C(O)O—CH₃, —C(O)O—CH₂—CH₃, and —SO₂—NH₂. For example, halo substituted aryl can be

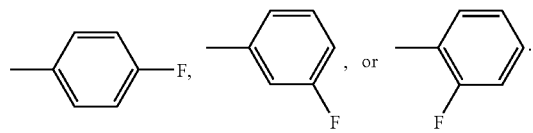

In one aspect, the present invention features a compound of Formula (I) selected from:

(S)-6-{3-[7-fluoro-2-(4-fluoro-benzyl)-3-oxo-2,3-dihydro-1H-isoindol-1-yl]-propionylamino}-nicotinic acid methyl ester;
(S)-6-{3-[7-fluoro-2-(4-fluoro-benzyl)-3-oxo-2,3-dihydro-1H-isoindol-1-yl]-propionylamino}-nicotinic acid;
6-{3-[2-(4-Dimethylamino-benzyl)-7-fluoro-3-oxo-2,3-dihydro-1H-isoindol-1-yl]-propionylamino}-nicotinic acid;
6-{3-[4,7-difluoro-2-(4-fluoro-benzyl)-3-oxo-2,3-dihydro-1H-isoindol-1-yl]-propionylamino}-nicotinic acid;
6-{3-[4-fluoro-2-(4-fluoro-benzyl)-3-oxo-2,3-dihydro-1H-isoindol-1-yl]-propionylamino}-nicotinic acid;
3-[7-fluoro-2-(4-fluoro-benzyl)-3-oxo-2,3-dihydro-1H-isoindol-1-yl]-N-(5-fluoro-pyridin-2-yl)-propionamide;
3-[7-fluoro-2-(4-fluoro-benzyl)-3-oxo-2,3-dihydro-1H-isoindol-1-yl]-N-pyridin-2-yl-propionamide;
3-[7-fluoro-2-(4-fluoro-benzyl)-3-oxo-2,3-dihydro-1H-isoindol-1-yl]-N-pyrazin-2-yl-propionamide;
3-[7-fluoro-2-(4-fluoro-benzyl)-3-oxo-2,3-dihydro-1H-isoindol-1-yl]-N-isoquinolin-3-yl-propionamide;
3-[7-fluoro-2-(4-fluoro-benzyl)-3-oxo-2,3-dihydro-1H-isoindol-1-yl]-N-quinolin-2-yl-propionamide;
N-(5-acetyl-pyridin-2-yl)-3-[7-fluoro-2-(4-fluoro-benzyl)-3-oxo-2,3-dihydro-1H-isoindol-1-yl]-propionamide;
6-{3-[2-(4-methoxy-benzyl)-3-oxo-2,3-dihydro-1H-isoindol-1-yl]-propionylamino}-nicotinic acid;
6-{3-[2-(4-fluoro-benzyl)-3-oxo-2,3-dihydro-1H-isoindol-1-yl]-propionylamino}-nicotinic acid;
3-[7-fluoro-2-(4-fluoro-benzyl)-3-oxo-2,3-dihydro-1H-isoindol-1-yl]-N-(5methoxymethoxymethyl-pyridin-2-yl)-propionamide;
3-[7-chloro-2-(4-fluoro-benzyl)-3-oxo-2,3-dihydro-1H-isoindol-1-yl]-N-pyridin-2-yl-propionamide; and
3-[7-fluoro-2-(4-fluoro-benzyl)-3-oxo-2,3-dihydro-1H-isoindol-1-yl]-N-[5-(4-fluoro-phenyl)-pyridin-2-yl]-propionamide.

In another aspect, the present invention features a compound of Formula (I) selected from

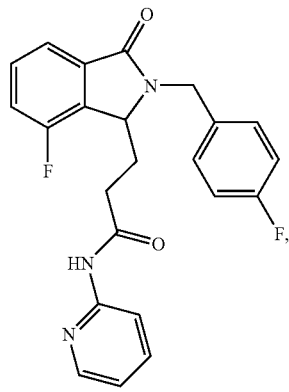

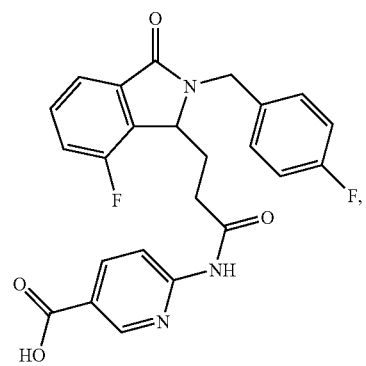

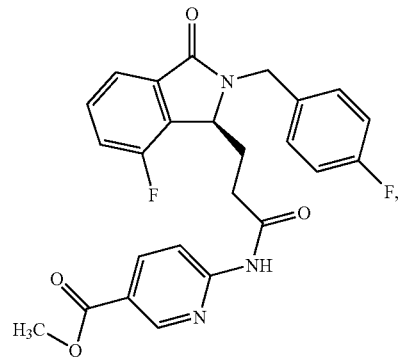

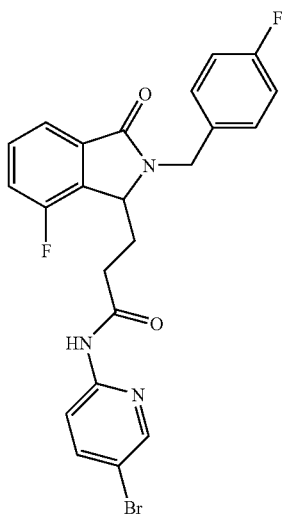

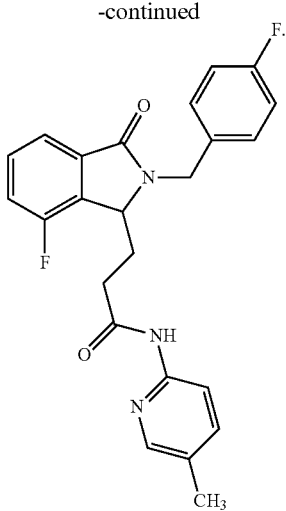

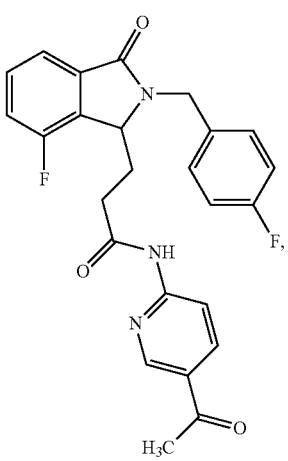

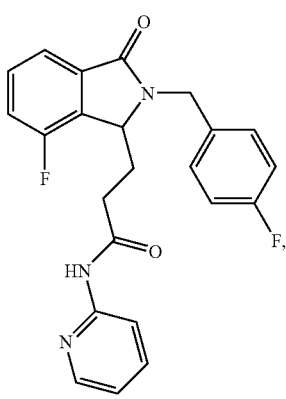

Another aspect of the present invention features a pharmaceutical composition comprising at least one compound of Formula (I) and at least one pharmaceutically acceptable carrier. In another aspect of the invention, the pharmaceutical composition further comprises at least one additional agent, drug, medicament, antibody and/or inhibitor for treating, ameliorating and/or preventing a glucokinase-mediated condition. In one embodiment of the pharmaceutical composition of the present invention, at least one compound of Formula (I) is selected from

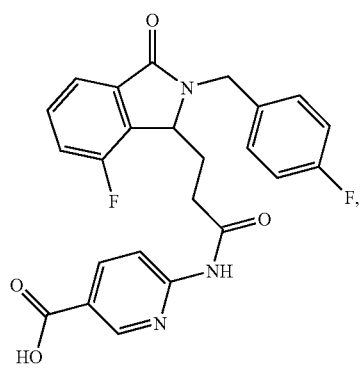

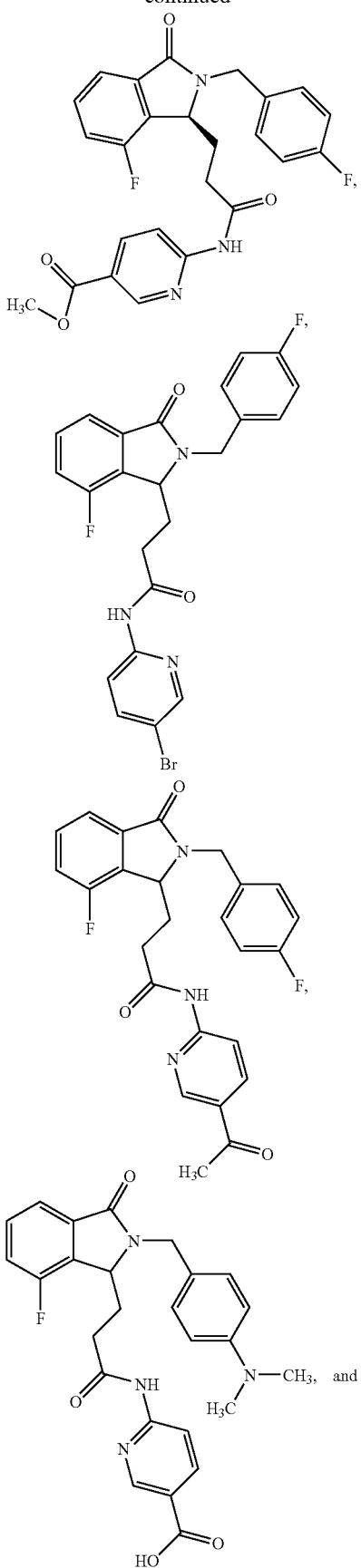

In another embodiment, at least one compound of Formula (I) is selected from (S)-6-{3-[7-fluoro-2-(4-fluoro-benzyl)-3-oxo-2,3-dihydro-1H-isoindol-1-yl]-propionylamino}-nicotinic acid methyl ester;

(S)-6-{3-[7-fluoro-2-(4-fluoro-benzyl)-3-oxo-2,3-dihydro-1H-isoindol-1-yl]-propionylamino}-nicotinic acid;

6-{3-[2-(4-dimethylamino-benzyl)-7-fluoro-3-oxo-2,3-dihydro-1H-isoindol-1-yl]-propionylamino}-nicotinic acid;

6-{3-[4,7-difluoro-2-(4-fluoro-benzyl)-3-oxo-2,3-dihydro-1H-isoindol-1-yl]-propionylamino}-nicotinic acid;

6-{3-[4-fluoro-2-(4-fluoro-benzyl)-3-oxo-2,3-dihydro-1H-isoindol-1-yl]-propionylamino}-nicotinic acid;

3-[7-fluoro-2-(4-fluoro-benzyl)-3-oxo-2,3-dihydro-1H-isoindol-1-yl]-N-(5-fluoro-pyridin-2-yl)-propionamide;

3-[7-fluoro-2-(4-fluoro-benzyl)-3-oxo-2,3-dihydro-1H-isoindol-1-yl]-N-pyridin-2-yl-propionamide;

3-[7-fluoro-2-(4-fluoro-benzyl)-3-oxo-2,3-dihydro-1H-isoindol-1-yl]-N-pyrazin-2-yl-propionamide;

3-[7-fluoro-2-(4-fluoro-benzyl)-3-oxo-2,3-dihydro-1H-isoindol-1-yl]-N-isoquinolin-3-yl-propionamide;

3-[7-fluoro-2-(4-fluoro-benzyl)-3-oxo-2,3-dihydro-1H-isoindol-1-yl]-N-quinolin-2-yl-propionamide;

N-(5-acetyl-pyridin-2-yl)-3-[7-fluoro-2-(4-fluoro-benzyl)-3-oxo-2,3-dihydro-1H-isoindol-1-yl]-propionamide;

6-{3-[2-(4-methoxy-benzyl)-3-oxo-2,3-dihydro-1H-isoindol-1-yl]-propionylamino}-nicotinic acid;

6-{3-[2-(4-fluoro-benzyl)-3-oxo-2,3-dihydro-1H-isoindol-1-yl]-propionylamino}-nicotinic acid;

3-[7-fluoro-2-(4-fluoro-benzyl)-3-oxo-2,3-dihydro-1H-isoindol-1-yl]-N-(5methoxymethoxymethyl-pyridin-2-yl)-propionamide;

3-[7-chloro-2-(4-fluoro-benzyl)-3-oxo-2,3-dihydro-1H-isoindol-1-yl]-N-pyridin-2-yl-propionamide; and 3-[7-fluoro-2-(4-fluoro-benzyl)-3-oxo-2,3-dihydro-1H-isoindol-1-yl]-N-[5-(4-fluoro-phenyl)-pyridin-2-yl]-propionamide.

In another embodiment of the invention a method is disclosed for treating, preventing or ameliorating a glucokinase-mediated condition in a subject in need thereof comprising administering to the subject a therapeutically effective amount of at least one compound of Formula (I). An embodiment of the invention includes a method for treating, preventing or ameliorating a glucokinase modulator-mediated condition selected from diabetes, obesity, and associated symptoms or complications thereof in a subject in need thereof, comprising administering to said subject a therapeutically effective amount of at least one compound of Formula (I).

A further embodiment of the invention is a method for treating, preventing or ameliorating a glucokinase modulator-mediated condition selected from IDDM, NIDDM, IGT (Impaired Glucose Tolerance), IFG (Impaired Fasting Glucose), Syndrome X (or Metabolic Syndrome), obesity, hyperglycemia, elevated blood glucose level, and insulin resistance in a subject in need thereof, comprising administering to said subject a therapeutically effective amount of at least one compound of Formula (I).

One embodiment of the invention is a method of treating diabetes, obesity, and associated symptoms or complications thereof.

Furthermore, glucokinase modulators can be co-administered with a second agent other than a glucokinase modulator; such second agent can be, for example, an anti-diabetic agent, a lipid lowering agent, a blood pressure lowering agent, direct thrombin inhibitor (DTI), and an anti-thrombotic agent (e.g., aspirin, heparins, glycoprotein IIb-IIIa inhibitors, or Factor Xa inhibitors).

Particularly, it is an embodiment of the invention to provide a method for treating or ameliorating a condition selected from diabetes, obesity, and associated symptoms or complications thereof in a subject in need thereof, comprising administering to said subject a therapeutically effective amount of (a) at least one compound of Formula (I); and (b) at least one additional agent selected from a second glucokinase modulator, an anti-diabetic agent, a lipid lowering agent, an anti-thrombotic agent, and a blood pressure lowering agent, said administration being in any order. In one embodiment, the additional agent is a second glucokinase modulator. In a further embodiment, the additional agent is an anti-diabetic agent. In another embodiment, the additional agent is a lipid lowering agent. In still another embodiment, the additional agent is an anti-thrombotic agent. In yet another embodiment, the additional agent is a blood pressure lowering agent.

Another embodiment of the invention is a method for preventing or inhibiting the onset of a glucokinase modulator mediated condition in a subject in need thereof, comprising administering to said subject a therapeutically effective amount of at least one compound of Formula (I). Another embodiment of the invention is a method for preventing or inhibiting the onset of a condition selected from diabetes, obesity, and associated symptoms or complications thereof in a subject in need thereof, comprising administering to said subject an effective amount of (a) at least one compound of Formula (I); and (b) at least one compound selected from the group consisting of a glucokinase modulator, an anti-diabetic agent, a lipid lowering agent, an anti-thrombotic agent, and a blood pressure lowering agent, said co-administration being in any order and the combined amounts providing the desired prophylactic effect.

A further embodiment of the invention is a method for preventing or inhibiting the onset of a condition selected from diabetes such as IDDM and NIDDM, IGT (Impaired Glucose Tolerance), IFG (Impaired Fasting Glucose), Syndrome X (or Metabolic Syndrome), hyperglycemia, elevated blood glucose, and insulin resistance in a subject in need thereof, comprising administering to said subject a prophylactically effective amount of at least one compound of Formula (I). In one embodiment, the additional agent is a second glucokinase modulator. In a further embodiment, the additional agent is an anti-diabetic agent. In another embodiment, the additional agent is a lipid lowering agent. In still another embodiment, the additional agent is an anti-thrombotic agent. In yet another embodiment, the additional agent is a blood pressure lowering agent.

It is a further embodiment of the invention to provide a process for making a pharmaceutical composition comprising admixing any of the compounds according to Formula (I) and a pharmaceutically acceptable carrier.

In a further embodiment of the invention, a method for treating or ameliorating a glucokinase-mediated condition in a subject in need thereof comprising administering to the subject a therapeutically effective amount of at least one compound of Formula (I), wherein the therapeutically effective amount of the compound of Formula (I) is from about 0.001 mg/kg/day to about 10 mg/kg/day.

In a further embodiment of the invention, a method for preventing or inhibiting the onset of a glucokinase-mediated condition in a subject in need thereof comprising administering to the subject a therapeutically effective amount of at least one compound of Formula (I), wherein the therapeutically effective amount of the compound of Formula (I) is from about 0.001 mg/kg/day to about 10 mg/kg/day.

The invention is further described below.

A) Terms

Some terms are defined below and by their usage throughout this disclosure.

Unless otherwise noted, "alkyl" as used herein, whether used alone or as part of a substituent group, refers to a saturated or unsaturated, branched, straight-chain or cyclic monovalent hydrocarbon radical derived by the removal of one hydrogen atom from a single carbon atom of a parent alkane. Typical alkyl groups include, but are not limited to, methyl; ethyls such as ethanyl; propyls such as propan-1-yl, propan-2-yl, cyclopropan-1-yl; butyls such as butan-1-yl, butan-2-yl, 2-methyl-propan-1-yl, 2-methyl-propan-2-yl, cyclobutan-1-yl and the like. In preferred embodiments, the alkyl groups are $C_{1-6}$alkyl, with $C_{1-3}$ being particularly preferred. "Alkoxy" radicals are oxygen ethers formed from the previously described straight, branched, or cyclic chain alkyl groups. In some embodiments, the alkyl or alkoxy are independently substituted with one to five, preferably one to three groups including, but not limited to, oxo, amino, alkoxy, carboxy, nitro, hydroxyl, and halo (F, Cl, Br, or I).

The term "alkenyl" refers to an unsaturated branched, straight-chain or cyclic monovalent hydrocarbon radical, which has at least one carbon-carbon double bond, derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In some embodiments, the alkenyl is substituted with one to five, preferably one to three groups including, but not limited to, amino, alkoxy, carboxy, nitro, hydroxyl, and halo.

The term "alkynyl" refers to an unsaturated branched, straight-chain or cyclic monovalent hydrocarbon radical, which has at least one carbon-carbon triple bond, derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In some embodiments, the alkynyl is substituted with one to five, preferably one to three groups including, but not limited to, amino, alkoxy, carboxy, nitro, hydroxyl, and halo.

The term "alkylene" denotes straight chain $C_{1-3}$alkyl diradical. For the $C_{2-3}$alkyl diradical the valencies are located on the two termini. In some embodiments, the alkylene may be optionally substituted with one or two groups including, but not limited to, halo.

The term "cycloalkyl," as used herein, refers to a stable, saturated or partially saturated monocyclic or bicyclic ring system containing from 3 to 8 ring carbons and preferably 5 to 7 ring carbons. Examples of such cyclic alkyl rings include cyclopropyl, cyclobutyl, cyclopentyl, cyclohexyl or cycloheptyl. In some embodiments, the cycloalkyl is substituted with one to five, preferably one to three groups including, but not limited to, amino, carboxy, nitro, hydroxyl, and halo.

The term "oxo" whether used alone or as part of a substituent group refers to an O= to either a carbon or a sulfur atom. For example, phthalimide and saccharin are examples of compounds with oxo substituents.

The term "aryl," as used herein, refers to aromatic groups comprising a stable six-membered monocyclic, or ten-membered bicyclic or fourteen-membered tricyclic aromatic ring system which consists of carbon atoms. Examples of aryl groups include, but are not limited to, phenyl or naphthalenyl. In some embodiments, "aryl" is substituted. For instance, "aryl" can be substituted with, e.g., optionally substituted $C_{1-6}$alkyl, $C_{2-6}$alkenyl, $C_{2-6}$alkynyl, halo, nitro, hydroxyl, ethynyl, —CN, aryl, heteroaryl, heterocyclyl, —$SO_3H$, —C(O)OH, —C(O)O—$C_{1-4}$alkyl, —C(O)NR'R", —SR', —OR', —C(O)R', —N(R')(R"), —$S(O)_2$—R', and —$S(O)_2$—N(R')(R"), wherein R' and R" are independently selected from H, $C_{1-6}$-alkyl, aryl, heteroaryl, and/or heterocyclyl.

The term "heteroaryl" refers to a monovalent heteroaromatic radical derived by the removal of one hydrogen atom from a single atom of a parent heteroaromatic ring system. Typical heteroaryl groups include monocyclic and bicyclic systems where one or both rings is heteroaromatic Heteroaromatic rings may contain 1-4 heteroatoms selected from O, N, and S. Examples include but are not limited to, radicals derived from carbazole, imidazole, indazole, indole, indolizine, isoindole, isoquinoline, isothiazole, isoxazole, naphthyridine, oxadiazole, oxazole, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, "heteroaryl" is substituted. For instance, "heteroaryl" can be substituted with, e.g., optionally substituted $C_{1-6}$alkyl, $C_{2-6}$alkenyl, $C_{2-6}$alkynyl, halo, nitro, hydroxyl, ethynyl, —CN, aryl, heteroaryl, heterocyclyl, —$SO_3H$, —C(O)OH, —C(O)O—$C_{1-4}$alkyl, —C(O)NR'R"—OR', —SR'—C(O)R', —N(R')(R"), —$S(O)_2$—R', and —$S(O)_2$—N(R')(R"), wherein R' and R" are independently selected from H, $C_{1-6}$-alkyl, aryl, heteroaryl, and/or heterocyclyl.

The term "heterocyclyl" or "heterocycle" is a 3- to 8-member saturated, or partially saturated single or fused ring system which consists of carbon atoms and from 1 to 6 heteroatoms selected from N, O and S. The heterocyclyl group may be attached at any heteroatom or carbon atom which results in the creation of a stable structure. Example of heterocyclyl groups include, but are not limited to, 2-imidazoline, imidazolidine; morpholine, oxazoline, 2-pyrroline, 3-pyrroline, pyrrolidine, pyridone, pyrimidone, piperazine, piperidine, indoline, tetrahydrofuran, 2-pyrroline, 3-pyrroline, 2-imidazoline, 2-pyrazoline, indolinone. A "heterocyclyl" can be a partially unsaturated ring such as 2-pyrroline, 3-pyrroline, 2-imidazoline, 2-pyrazoline, indolinone, or. "Heterocyclyl" being connected to N(1), as shown in Formula (I), through a ring carbon atom that is double-bonded to a ring nitrogen can include, but is not limited to 4,5-dihydrothiazole, 3-psuedo-indolone, and pyrimidone. In some embodiments, "heterocyclyl" or "heterocycle" are independently substituted. For instance, "heterocyclyl" or "heterocycle" can be substituted with, e.g., optionally substituted $C_{1-6}$alkyl, $C_{2-6}$alkenyl, $C_{2-6}$alkynyl, halo, nitro, hydroxyl, ethynyl, —CN, aryl, heteroaryl, heterocyclyl, —$SO_3H$, —C(O)OH, —C(O)O—$C_{1-4}$alkyl, C(O)NR'R", —OR', —SR', —C(O)R', —N(R')(R"), —$S(O)_2$—R', and —$S(O)_2$—N(R')(R"), wherein R' and R" are independently selected from H, $C_{1-6}$-alkyl, aryl, heteroaryl, and/or heterocyclyl.

The term "substituted" refers to a radical in which one or more hydrogen atoms are each independently replaced with the same or different substituent(s).

With reference to substituents, the term "independently" means that when more than one of such substituent is possible, such substituents may be the same or different from each other.

The term "composition" is intended to encompass a product comprising the specified ingredients in the specified amounts, as well as any product which results, directly or indirectly, from combinations of the specified ingredients in the specified amounts.

The term "subject" as used herein, refers to an animal, preferably a mammal, most preferably a human, who is the object of treatment, observation or experiment.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "allosteric modulator" as used herein, refers to a molecule that stabilizes conformations or forms of the glucokinase protein, through binding to a site remote from the catalytic site on the protein. This effect may be manifested through alteration of the catalytic nature of the protein. Experimentally, the effect can be observed by examining the degree of activation, or by deriving the $K_m$ or $V_{max}$, for the phosphorylation of glucose by glucokinase in the presence of the modulator. Alternatively, the effect of the allosteric modulator may be manifested through stabilization of glucokinase toward regulatory mechanisms in cellular systems or animals.

Diabetes, obesity, and associated symptoms or complications include such conditions as IDDM, NIDDM, IGT (Impaired Glucose Tolerance), IFG (Impaired Fasting Glucose), Syndrome X (or Metabolic Syndrome), hyperglycemia, elevated blood glucose level, and insulin resistance. IGT and IFG are also known as "prediabetic state."

Methods are known in the art for determining effective doses for therapeutic and prophylactic purposes for the disclosed pharmaceutical compositions or the disclosed drug combinations, whether or not formulated in the same composition. For therapeutic purposes, the term "therapeutically effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "therapeutically effective amount" refers to that amount of each active compound or pharmaceutical agent, alone or in combination, that treats or inhibits in a subject the onset or progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together.

The term "pharmaceutically acceptable salt" refers to non-toxic pharmaceutically acceptable salts (Ref. International J. Pharm., 1986, 33, 201-217; J. Pharm. Sci., 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The term "protecting groups" refer to those moieties known in the art that are used to mask functional groups; protecting groups may be removed during subsequent synthetic transformations or by metabolic or other in vivo administration conditions. During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, Third Edition, John Wiley & Sons, 1999. The protecting groups may be removed at a convenient subsequent stage using methods known in the art.

B) Compounds

| STRUCTURE | COMPOUND # | NAME |
|---|---|---|
| 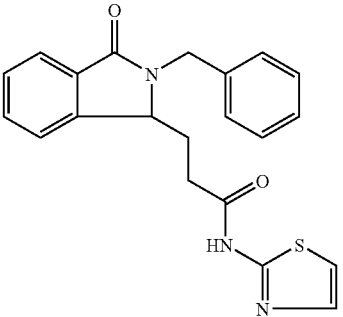 [SMILES: O=C(CCC1c2ccccc2C(=O)N1Cc1ccccc1)Nc1nccs1] | 1 | 3-(2-Benzyl-3-oxo-2,3-dihydro-1H-iso-indol-1-yl)-N-thiazol-2-yl-propionamide |
| 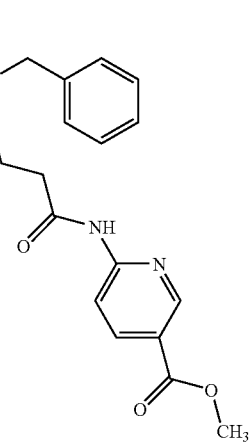 | 2 | 6-[3-(2-Benzyl-3-oxo-2,3-dihydro-1H-iso-indol-1-yl)-propionylamino]-nicotinic acid methyl ester |

-continued

| STRUCTURE | COMPOUND # | NAME |
|---|---|---|
| 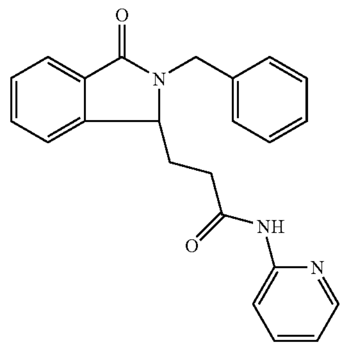 [SMILES: O=C(CCC1c2ccccc2C(=O)N1Cc1ccccc1)Nc1ccccn1] | 3 | 3-(2-Benzyl-3-oxo-2,3-dihydro-1H-iso-indol-1-yl)-N-pyridin-2-yl-propionamide |
| 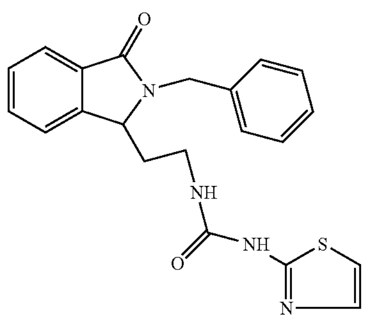 [SMILES: O=C(NCCC1c2ccccc2C(=O)N1Cc1ccccc1)Nc1nccs1] | 4 | 1-[2-(2-Benzyl-3-oxo-2,3-dihydro-1H-iso-indol-1-yl)-ethyl]-3-thiazol-2-yl-urea |
| 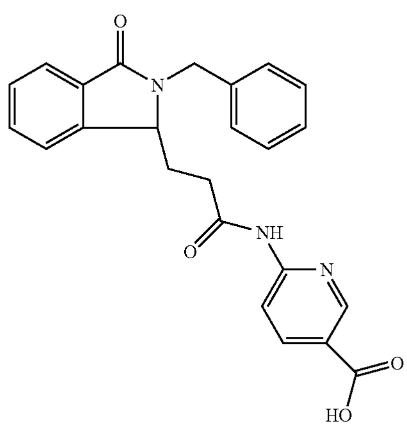 [SMILES: O=C(CCC1c2ccccc2C(=O)N1Cc1ccccc1)Nc1ccc(C(=O)O)cn1] | 5 | 6-[3-(2-Benzyl-3-oxo-2,3-dihydro-1H-iso-indol-1-yl)-propionylamino]-nicotinic acid |
| 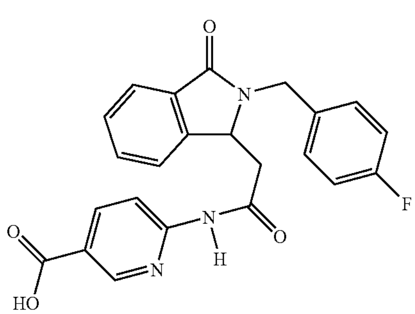 [SMILES: O=C(CC1c2ccccc2C(=O)N1Cc1ccc(F)cc1)Nc1ccc(C(=O)O)cn1] | 6 | 6-{2-[2-(4-Fluoro-benzyl)-3-oxo-2,3-dihydro-1H-isoindol-1-yl]-acetyl-amino}-nicotinic acid |

| STRUCTURE | COMPOUND # | NAME |
| --- | --- | --- |
| 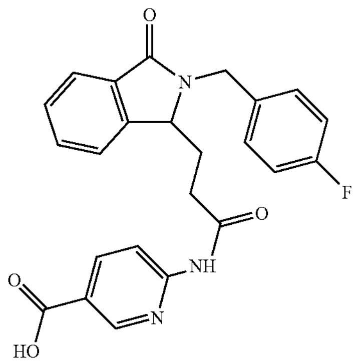 [SMILES: O=C(CCC1c2ccccc2C(=O)N1Cc1ccc(F)cc1)Nc1ccc(C(=O)O)cn1] | 7 | 6-{3-[2-(4-Fluoro-benzyl)-3-oxo-2,3-di-hydro-1H-isoindol-1-yl]-pro-pionylamino}-nicotinic acid |
| 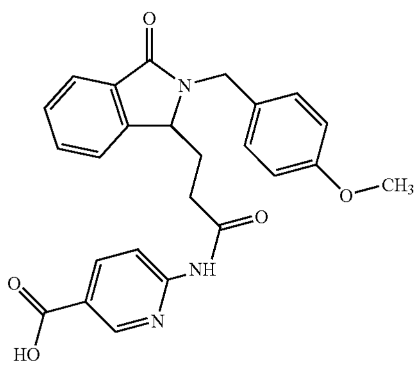 [SMILES: COc1ccc(CN2C(=O)c3ccccc3C2CCC(=O)Nc2ccc(C(=O)O)cn2)cc1] | 8 | 6-{3-[2-(4-Methoxy-benzyl)-3-oxo-2,3-di-hydro-1H-isoindol-1-yl]-pro-pionylamino}-nicotinic acid |
| 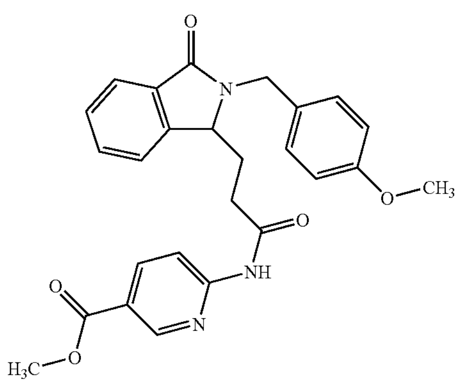 | 9 | 6-{3-[2-(4-Methoxy-benzyl)-3-oxo-2,3-di-hydro-1H-isoindol-1-yl]-pro-pionylamino}-nicotinic acid methyl ester |
| 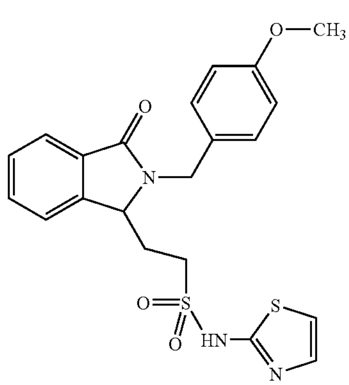 [SMILES: COc1ccc(CN2C(=O)c3ccccc3C2CCS(=O)(=O)Nc2nccs2)cc1] | 10 | 2-[2-(4-Methoxy-benzyl)-3-oxo-2,3-di-hydro-1H-isoindol-1-yl]-eth-anesulfonic acid thiazol-2-yl-amide |

-continued

| STRUCTURE | COMPOUND # | NAME |
|---|---|---|
| 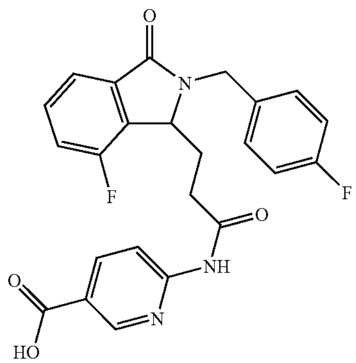 [SMILES: O=C(CCC1c2c(F)cccc2C(=O)N1Cc1ccc(F)cc1)Nc1ccc(C(=O)O)cn1] | 11 | 6-{3-[7-Fluoro-2-(4-fluoro-benzyl)-3-oxo-2,3-dihydro-1H-isoindol-1-yl]-propionylamino}-nicotinic acid |
| 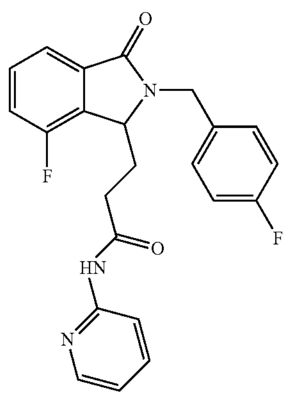 | 12 | 3-[7-Fluoro-2-(4-fluoro-benzyl)-3-oxo-2,3-dihydro-1H-isoindol-1-yl]-N-pyridin-2-yl-propionamide |
| 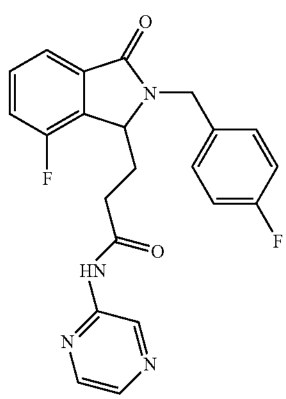 [SMILES: O=C(CCC1c2c(F)cccc2C(=O)N1Cc1ccc(F)cc1)Nc1cnccn1] | 13 | 3-[7-Fluoro-2-(4-fluoro-benzyl)-3-oxo-2,3-dihydro-1H-isoindol-1-yl]-N-pyrazin-2-yl-propionamide |
| 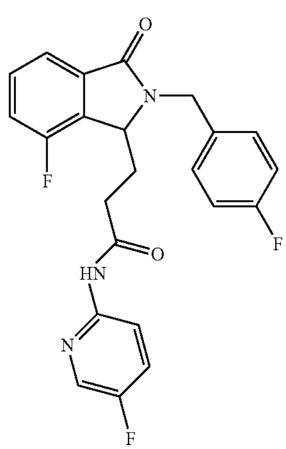 [SMILES: O=C(CCC1c2c(F)cccc2C(=O)N1Cc1ccc(F)cc1)Nc1ccc(F)cn1] | 14 | 3-[7-Fluoro-2-(4-fluoro-benzyl)-3-oxo-2,3-dihydro-1H-isoindol-1-yl]-N-(5-fluoro-pyridin-2-yl)-propionamide |

-continued

| STRUCTURE | COMPOUND # | NAME |
|---|---|---|
| 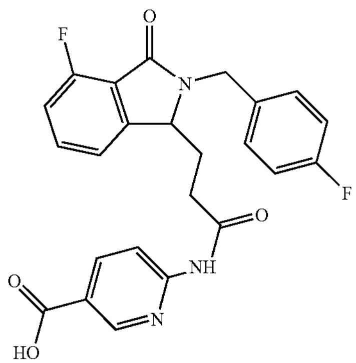 [SMILES: O=C(CCC1c2cccc(F)c2C(=O)N1Cc1ccc(F)cc1)Nc1ccc(C(=O)O)cn1] | 15 | 6-{3-[4-Fluoro-2-(4-fluoro-benzyl)-3-oxo-2,3-dihydro-1H-isoindol-1-yl]-propionylamino}-nicotinic acid |
| 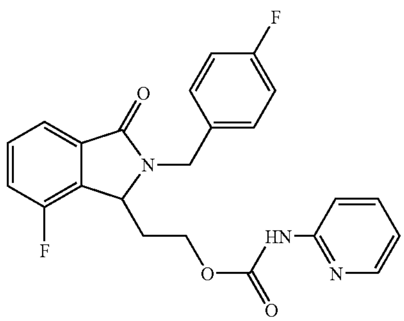 [SMILES: O=C(Nc1ccccn1)OCCC1c2c(F)cccc2C(=O)N1Cc1ccc(F)cc1] | 16 | Pyridin-2-yl-carbamic acid 2-[7-fluoro-2-(4-fluoro-benzyl)-3-oxo-2,3-dihydro-1H-isoindol-1-yl]-ethyl ester |
| 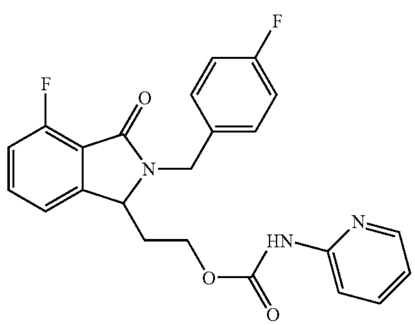 [SMILES: O=C(Nc1ccccn1)OCCC1c2cccc(F)c2C(=O)N1Cc1ccc(F)cc1] | 17 | Pyridin-2-yl-carbamic acid 2-[4-fluoro-2-(4-fluoro-benzyl)-3-oxo-2,3-dihydro-1H-isoindol-1-yl]-ethyl ester |
| 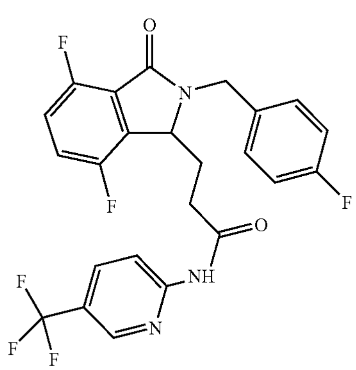 [SMILES: O=C(CCC1c2c(F)ccc(F)c2C(=O)N1Cc1ccc(F)cc1)Nc1ccc(C(F)(F)F)cn1] | 18 | 3-[4,7-Difluoro-2-(4-fluoro-benzyl)-3-oxo-2,3-dihydro-1H-isoindol-1-yl]-N-(5-trifluoromethyl-pyridin-2-yl)-propionamide |

-continued

| STRUCTURE | COMPOUND # | NAME |
|---|---|---|
| 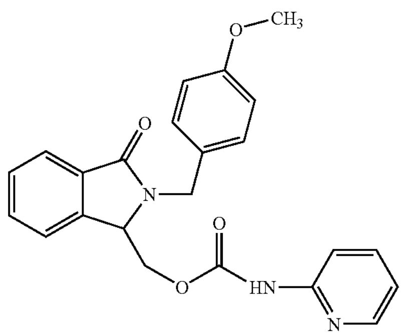 | 19 | Pyridin-2-yl-carbamic acid 2-(4-methoxy-benzyl)-3-oxo-2,3-dihydro-1H-isoindol-1-ylmethyl ester |
| 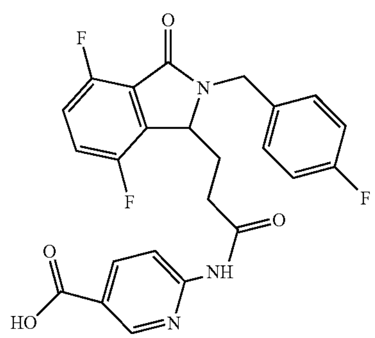 [SMILES: O=C(CCC1c2c(F)ccc(F)c2C(=O)N1Cc1ccc(F)cc1)Nc1ccc(C(=O)O)cn1] | 20 | 6-{3-[4,7-Difluoro-2-(4-fluoro-benzyl)-3-oxo-2,3-dihydro-1H-isoindol-1-yl]-propionylamino}-nicotinic acid |
| 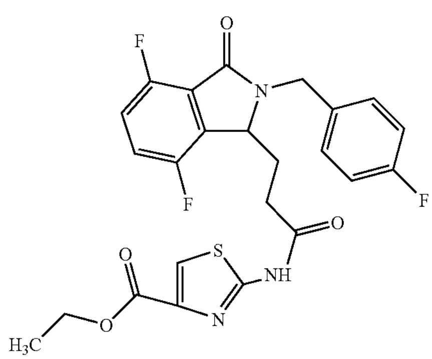 [SMILES: CCOC(=O)c1csc(NC(=O)CCC2c3c(F)ccc(F)c3C(=O)N2Cc2ccc(F)cc2)n1] | 21 | 2-{3-[4,7-Difluoro-2-(4-fluoro-benzyl)-3-oxo-2,3-dihydro-1H-isoindol-1-yl]-propionylamino}thiazole-4-carboxylic acid ethyl ester |
| 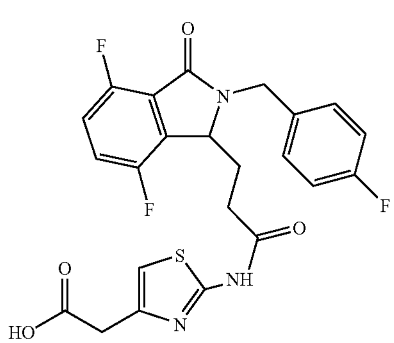 [SMILES: O=C(O)Cc1csc(NC(=O)CCC2c3c(F)ccc(F)c3C(=O)N2Cc2ccc(F)cc2)n1] | 22 | (2-{3-[4,7-Difluoro-2-(4-fluoro-benzyl)-3-oxo-2,3-dihydro-1H-isoindol-1-yl]-propionylamino}-thiazol-4-yl)-acetic acid |

-continued

| STRUCTURE | COMPOUND # | NAME |
|---|---|---|
| 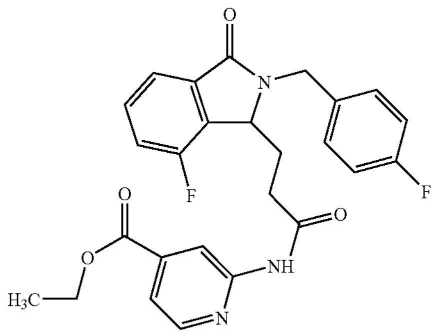 [SMILES: CCOC(=O)c1ccnc(NC(=O)CCC2c3c(F)cccc3C(=O)N2Cc2ccc(F)cc2)c1] | 23 | 2-{3-[7-Fluoro-2-(4-fluoro-benzyl)-3-oxo-2,3-dihydro-1H-isoindol-1-yl]-propionylamino}-isonicotinic acid ethyl ester |
| 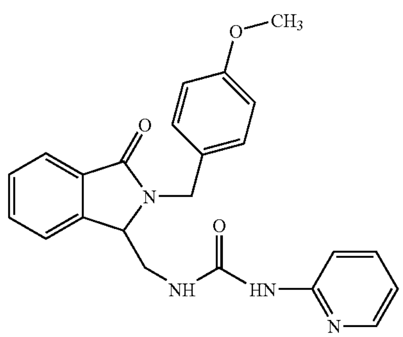 [SMILES: COc1ccc(CN2C(=O)c3ccccc3C2CNC(=O)Nc2ccccn2)cc1] | 24 | 1-[2-(4-Methoxy-benzyl)-3-oxo-2,3-dihydro-1H-isoindol-1-ylmethyl]-3-pyridin-2-yl-urea |
| 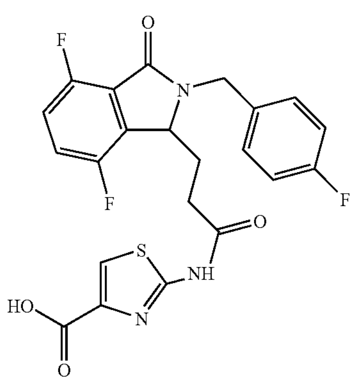 [SMILES: O=C(CCC1c2c(F)ccc(F)c2C(=O)N1Cc1ccc(F)cc1)Nc1nc(C(=O)O)cs1] | 25 | 2-{3-[4,7-Difluoro-2-(4-fluoro-benzyl)-3-oxo-2,3-dihydro-1H-isoindol-1-yl]-propionylamino}-thiazole-4-carboxylic acid |
| 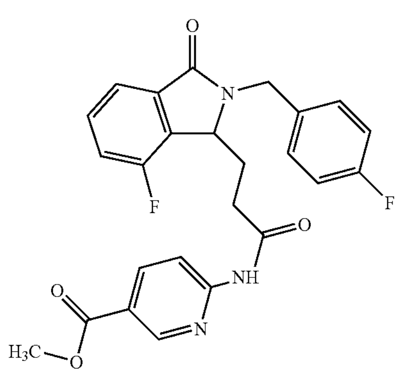 [SMILES: COC(=O)c1ccc(NC(=O)CCC2c3c(F)cccc3C(=O)N2Cc2ccc(F)cc2)nc1] | 26 | 6-{3-[7-Fluoro-2-(4-fluoro-benzyl)-3-oxo-2,3-dihydro-1H-isoindol-1-yl]-propionylamino}-nicotinic acid methyl ester |

-continued

| STRUCTURE | COMPOUND # | NAME |
|---|---|---|
| 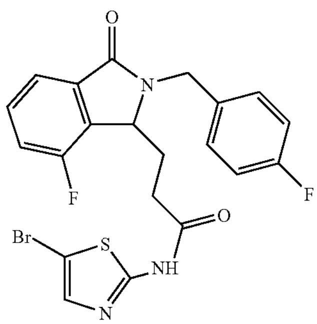 [SMILES: O=C(CCC1c2c(F)cccc2C(=O)N1Cc1ccc(F)cc1)Nc1ncc(Br)s1] | 27 | N-(5-Bromo-thiazol-2-yl)-3-[7-fluoro-2-(4-fluoro-benzyl)-3-oxo-2,3-dihydro-1H-isoindol-1-yl]-propionamide |
| 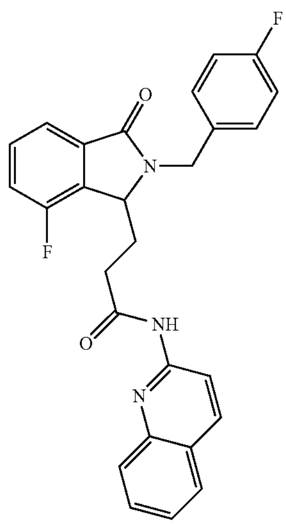 [SMILES: O=C(CCC1c2c(F)cccc2C(=O)N1Cc1ccc(F)cc1)Nc1ccc2ccccc2n1] | 28 | 3-[7-Fluoro-2-(4-fluoro-benzyl)-3-oxo-2,3-dihydro-1H-isoindol-1-yl]-N-quinolin-2-yl-propionamide |
| 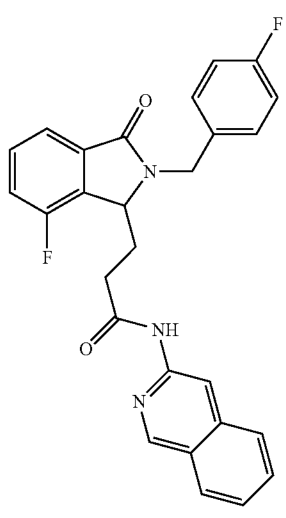 [SMILES: O=C(CCC1c2c(F)cccc2C(=O)N1Cc1ccc(F)cc1)Nc1cc2ccccc2cn1] | 29 | 3-[7-Fluoro-2-(4-fluoro-benzyl)-3-oxo-2,3-dihydro-1H-isoindol-1-yl]-N-isoquinolin-3-yl-propionamide |

| STRUCTURE | COMPOUND # | NAME |
|---|---|---|
| 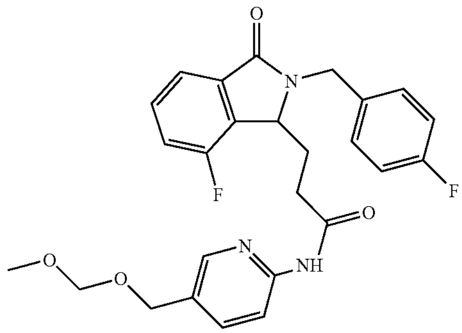 [SMILES: COCOCc1ccc(NC(=O)CCC2c3c(F)cccc3C(=O)N2Cc2ccc(F)cc2)nc1] | 30 | 3-[7-Fluoro-2-(4-fluoro-benzyl)-3-oxo-2,3-dihydro-1H-isoindol-1-yl]-N-(5methoxymethoxymethyl-pyridin-2-yl)-propionamide |
| 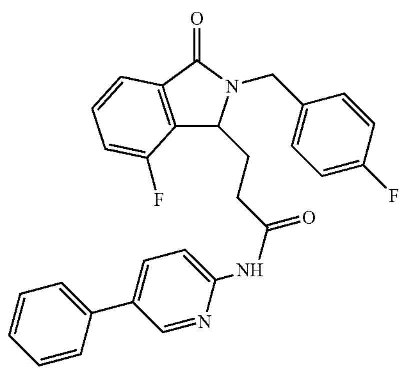 [SMILES: O=C(CCC1c2c(F)cccc2C(=O)N1Cc1ccc(F)cc1)Nc1ccc(-c2ccccc2)cn1] | 31 | 3-[7-Fluoro-2-(4-fluoro-benzyl)-3-oxo-2,3-dihydro-1H-isoindol-1-yl]-N-(5-phenyl-pyridin-2-yl)-propionamide |
| 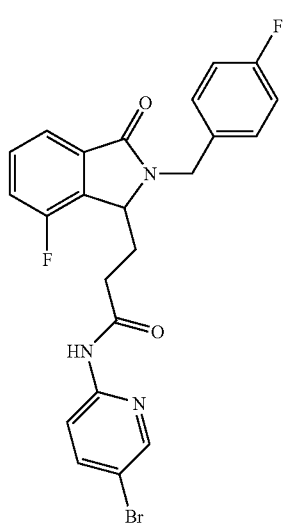 [SMILES: O=C(CCC1c2c(F)cccc2C(=O)N1Cc1ccc(F)cc1)Nc1ccc(Br)cn1] | 32 | N-(5-Bromo-pyridin-2-yl)-3-[7-fluoro-2-(4-fluoro-benzyl)-3-oxo-2,3-dihydro-1H-isoindol-1-yl]-propionamide |

| STRUCTURE | COMPOUND # | NAME |
|---|---|---|
| 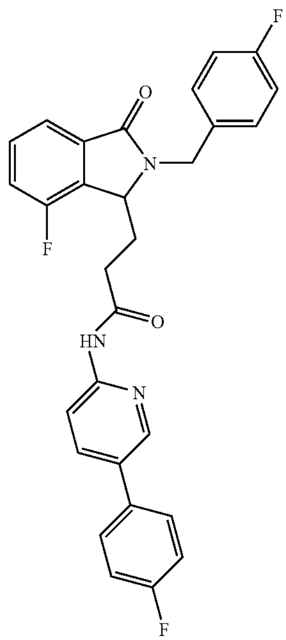 [SMILES: O=C(CCC1c2c(F)cccc2C(=O)N1Cc1ccc(F)cc1)Nc1ccc(-c2ccc(F)cc2)cn1] | 33 | 3-[7-Fluoro-2-(4-fluoro-benzyl)-3-oxo-2,3-dihydro-1H-isoindol-1-yl]-N-[5-(4-fluorophenyl)-pyridin-2-yl]-propionamide |
| 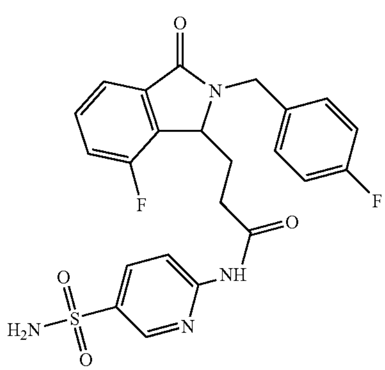 [SMILES: NS(=O)(=O)c1ccc(NC(=O)CCC2c3c(F)cccc3C(=O)N2Cc2ccc(F)cc2)nc1] | 34 | 3-[7-Fluoro-2-(4-fluoro-benzyl)-3-oxo-2,3-dihydro-1H-isoindol-1-yl]-N-(5-sulfamoyl-pyridin-2-yl)-propionamide |
| 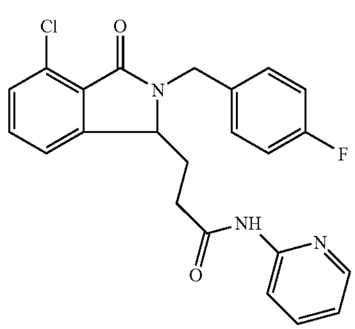 [SMILES: O=C(CCC1c2cccc(Cl)c2C(=O)N1Cc1ccc(F)cc1)Nc1ccccn1] | 35 | 3-[4-Chloro-2-(4-fluoro-benzyl)-3-oxo-2,3-dihydro-1H-isoindol-1-yl]-N-pyridin-2-yl-propionamide |

| STRUCTURE | COMPOUND # | NAME |
| --- | --- | --- |
| 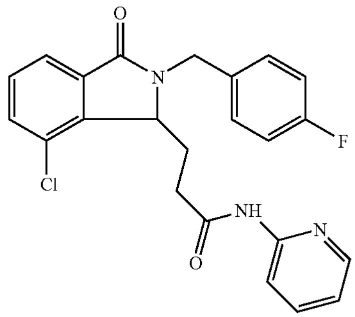 [SMILES: O=C(CCC1c2c(Cl)cccc2C(=O)N1Cc1ccc(F)cc1)Nc1ccccn1] | 36 | 3-[7-Chloro-2-(4-fluoro-benzyl)-3-oxo-2,3-dihydro-1H-isodinol-1-yl]-N-pyridin-2-yl-propionamide |
| 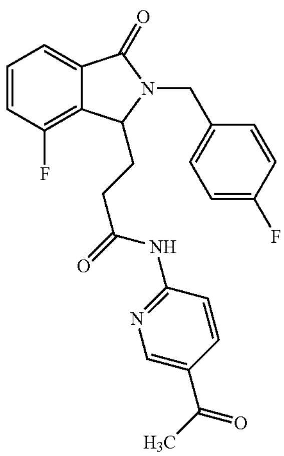 [SMILES: CC(=O)c1ccc(NC(=O)CCC2c3c(F)cccc3C(=O)N2Cc2ccc(F)cc2)nc1] | 37 | N-(5-Acetyl-pyridin-2-yl)-3-[7-fluoro-2-(4-fluoro-benzyl)-3-oxo-2,3-dihydro-1H-isoindol-1-yl]-propionamide |
| 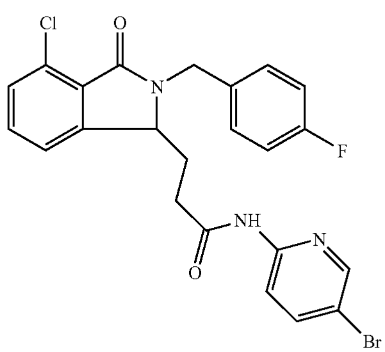 [SMILES: O=C(CCC1c2cccc(Cl)c2C(=O)N1Cc1ccc(F)cc1)Nc1ccc(Br)cn1] | 38 | N-(5-Bromo-pyridin-2-yl)-3-[4-chloro-2-(4-fluoro-benzyl)-3-oxo-2,3-dihydro-1H-isoindol-1-yl]-propionamide |
| 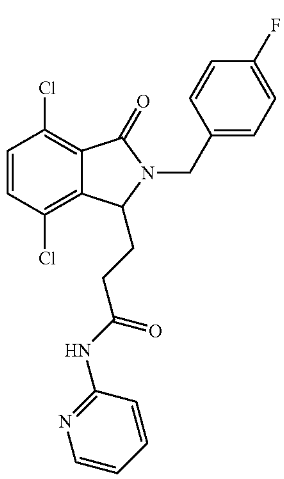 [SMILES: O=C(CCC1c2c(Cl)ccc(Cl)c2C(=O)N1Cc1ccc(F)cc1)Nc1ccccn1] | 39 | 3-[4,7-Dichloro-2-(4-fluoro-benzyl)-3-oxo-2,3-dihydro-1H-isoindol-1-yl]-N-pyridin-2-yl-propionamide |

-continued

| STRUCTURE | COMPOUND # | NAME |
|---|---|---|
| 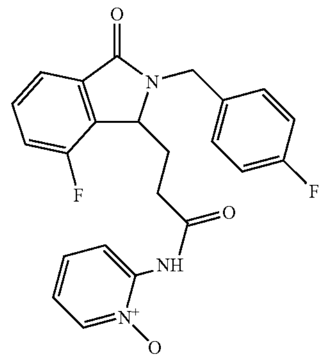 [SMILES: O=C(CCC1c2c(F)cccc2C(=O)N1Cc1ccc(F)cc1)Nc1cccc[n+]1O] | 40 | 3-[7-Fluoro-2-(4-fluoro-benzyl)-3-oxo-2,3-dihydro-1H-isoindol-1-yl]-N-(1-oxy-pyridin-2-yl)-propionamide |
| 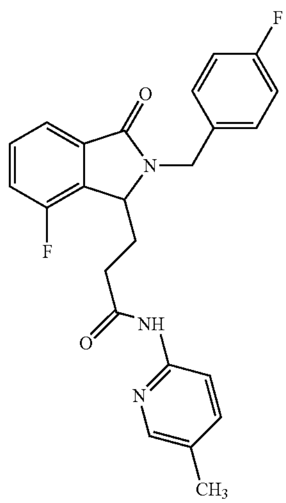 [SMILES: Cc1ccc(NC(=O)CCC2c3c(F)cccc3C(=O)N2Cc2ccc(F)cc2)nc1] | 41 | 3-[7-Fluoro-2-(4-fluoro-benzyl)-3-oxo-2,3-dihydro-1H-isoindol-1-yl]-N-(5-methyl-pyridin-2-yl)-propionamide |
| 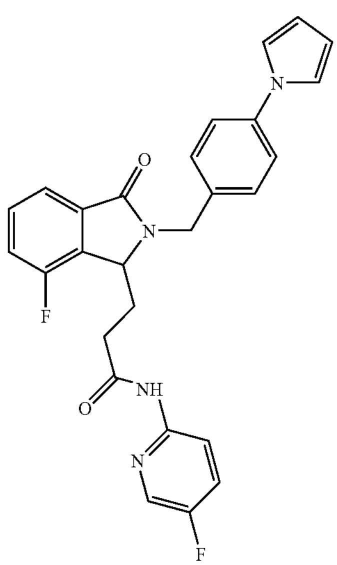 [SMILES: O=C(CCC1c2c(F)cccc2C(=O)N1Cc1ccc(-n2cccc2)cc1)Nc1ccc(F)cn1] | 42 | 3-[7-Fluoro-3-oxo-2-(4-pyrrol-1-yl-benzyl)-2,3-dihydro-1H-isoindol-1-yl]-N-(5-fluoro-pyridin-2-yl)-propionamide |

| STRUCTURE | COMPOUND # | NAME |
|---|---|---|
| 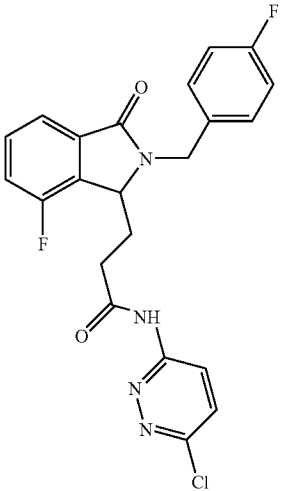 [SMILES: O=C(CCC1c2c(F)cccc2C(=O)N1Cc1ccc(F)cc1)Nc1ccc(Cl)cn1] | 43 | N-(6-Chloro-pyridazin-3-yl)-3-[7-fluoro-2-(4-fluoro-benzyl)-3-oxo-2,3-dihydro-1H-isoindol-1-yl]-Propionamide |
| 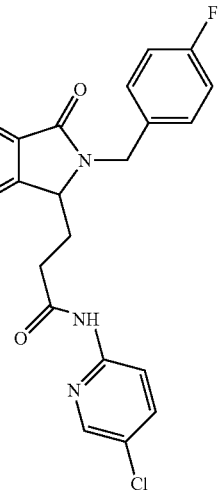 | 44 | N-(5-Chloro-pyridin-2-yl)-3-[7-fluoro-2-(4-fluoro-benzyl)-3-oxo-2,3-dihydro-1H-isoindol-1-yl]-propionamide |
| 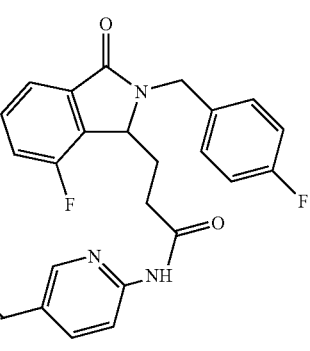 | 45 | 3-(6-{3-[7-Fluoro-2-(4-fluoro-benzyl)-3-oxo-2,3-dihydro-1H-isoindol-1-yl]-propionylamino}-pyridin-3-yl)-acrylic acid ethyl ester |

| STRUCTURE | COMPOUND # | NAME |
|---|---|---|
| 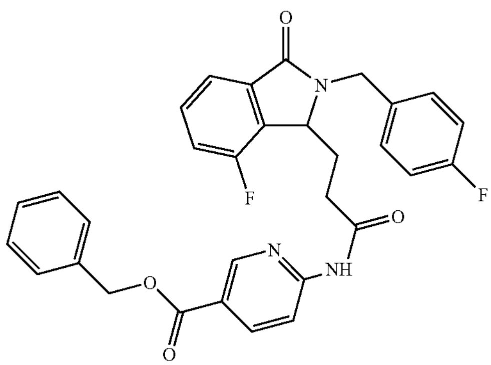 [SMILES: O=C(CCC1c2c(F)cccc2C(=O)N1Cc1ccc(F)cc1)Nc1ccc(C(=O)OCc2ccccc2)cn1] | 46 | 6-{3-[7-Fluoro-2-(4-fluoro-benzyl)-3-oxo-2,3-dihydro-1H-isoindol-1-yl]-propionylamino}-nicotinic acid benzyl ester |
| 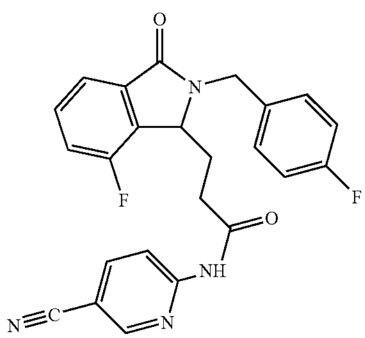 [SMILES: N#Cc1ccc(NC(=O)CCC2c3c(F)cccc3C(=O)N2Cc2ccc(F)cc2)nc1] | 47 | N-(5-Cyano-pyridin-2-yl)-3-[7-fluoro-2-(4-fluoro-benzyl)-3-oxo-2,3-dihydro-1H-isoindol-1-yl]-propionamide |
| 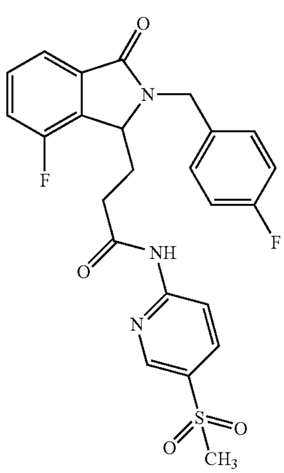 [SMILES: CS(=O)(=O)c1ccc(NC(=O)CCC2c3c(F)cccc3C(=O)N2Cc2ccc(F)cc2)nc1] | 48 | 3-[7-Fluoro-2-(4-fluoro-benzyl)-3-oxo-2,3-dihydro-1H-isoindol-1-yl]-N-(5-methanesulfonyl-pyridin-2-yl)-propionamide |

-continued

| STRUCTURE | COMPOUND # | NAME |
|---|---|---|
| (structure) | 49 | 6-{3-[2-(4-Dimethylamino-benzyl)-7-fluoro-3-oxo-2,3-dihydro-1H-isoindol-1-yl]-propionylamino}-nicotinic acid |
| (structure) | 50 | (R)-6-{3-[7-Fluoro-2-(4-fluoro-benzyl)-3-oxo-2,3-dihydro-1H-isoindol-1-yl]-propionylamino}-nicotinic acid methyl ester |
| (structure) | 51 | (S)-6-{3-[7-Fluoro-2-(4-fluoro-benzyl)-3-oxo-2,3-dihydro-1H-isoindol-1-yl]-propionylamino}-nicotinic acid methyl ester |

C) Synthesis

The invention provides methods of making the disclosed compounds according to traditional organic synthetic methods as well as matrix or combinatorial synthetic methods. Schemes I through IV describe suggested synthetic routes. Using these Schemes, the guidelines below, and the examples, a person of skill in the art may develop analogous or similar methods for a given compound that is within the invention. These methods are representative of the synthetic schemes, but are not to be construed as limiting the scope of the invention.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixtures of stereoisomers, these isomers may be separated by conventional techniques such as preparative chromatography. The compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers and enantiomers thereof are encompassed within the scope of the present invention.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Examples of the described synthetic routes include Examples 1 through 51 and Schemes I-IV. Compounds analogous to the target compounds of these examples can be made according to similar routes. The disclosed compounds are useful as pharmaceutical agents as described in the next section.

Abbreviations or acronyms useful herein include:
AIBN (2,2'-Azobisisobutyronitrile)
Boc (tert butyl carbamate)
BOP (Benzotriazol-1-yloxy)tris(dimethylamino)phosphonium hexfluorophosphate)
BuLi (butyllithium)
DIBAL-H (Diisobutylaluminum hydride)
DMAP (4-(dimethylamino)pyridine)
DME (Ethylene glycol dimethyl ether)
DMF (dimethylformamide)
DMPU (1,3-Dimethyl-3,4,5,6-tetrahydro-2(1H)-pyrimidinone)
DMSO (methyl sulfoxide)
EDC (N-(3-Dimethylaminopropyl)-N'-ethylcarbodiimide)
EDCI (1-(3-Dimethylaminopropyl)-3-ethylcarbodiimide hydrochloride)
EtOAc (ethyl acetate)
HATU (O-(7-Azabenzotriazol-1-yl)-N,N,N',N'-tetramethyluronium hexafluorophosphate)
HMPA (Hexamethylphosphoramide)
HOBt (1-Hydroxybenzotriazole monohydrate)
LCMS (high pressure liquid chromatography with mass spectrometer)
LDA (Lithium diisopropylamide)
LHMDS (lithium hexamethyl disilazide)
MOM (Methoxymethyl)
NaHMDS (sodium hexamethyl disilazide)
NaO$^t$Bu (sodium tert-butoxide)
NBS (N-Bromosuccinimide)
NMP (N-Methyl Pyrrolidinone)
SPE (solid phase extraction)
TBTU (O-Benzotriazol-1-yl-N,N,N',N'-tetramethyluronium hexafluorophosphate)
TEMPO (2,2,6,6-tetramethyl-1-piperdinyloxy, free radical)
TFA (trifluoroacetic acid);
THF (tetrahydrofuran)
TLC (thin layer chromatography)
General Guidance

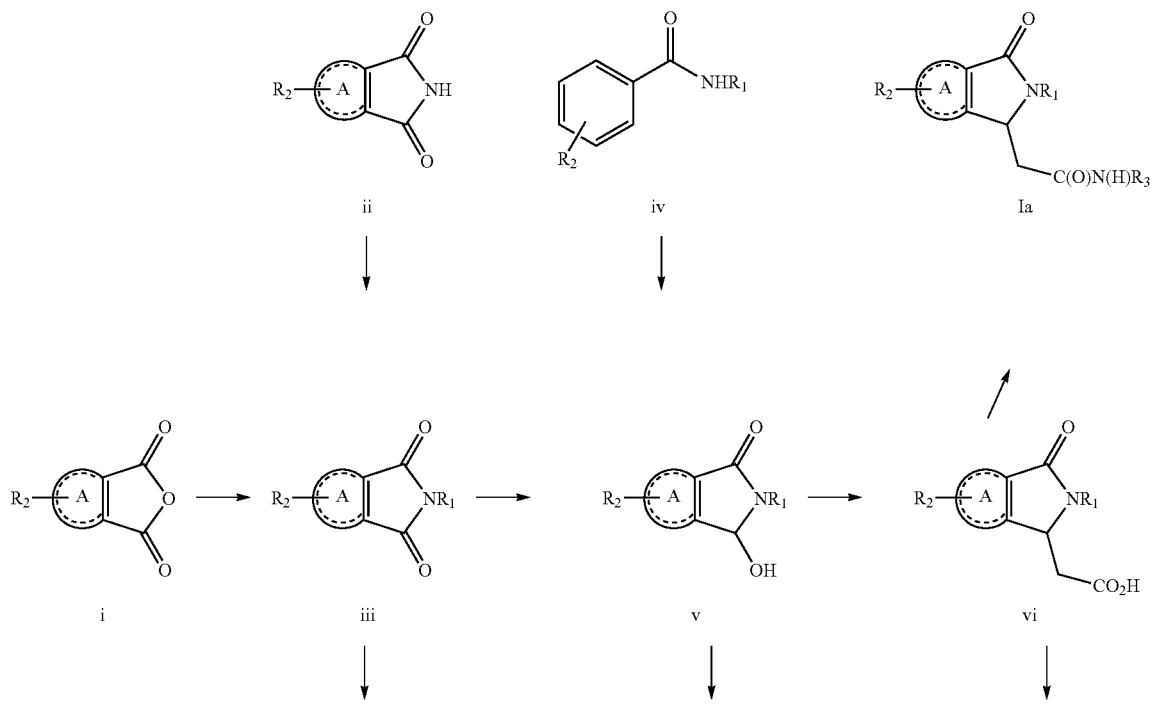

Scheme I

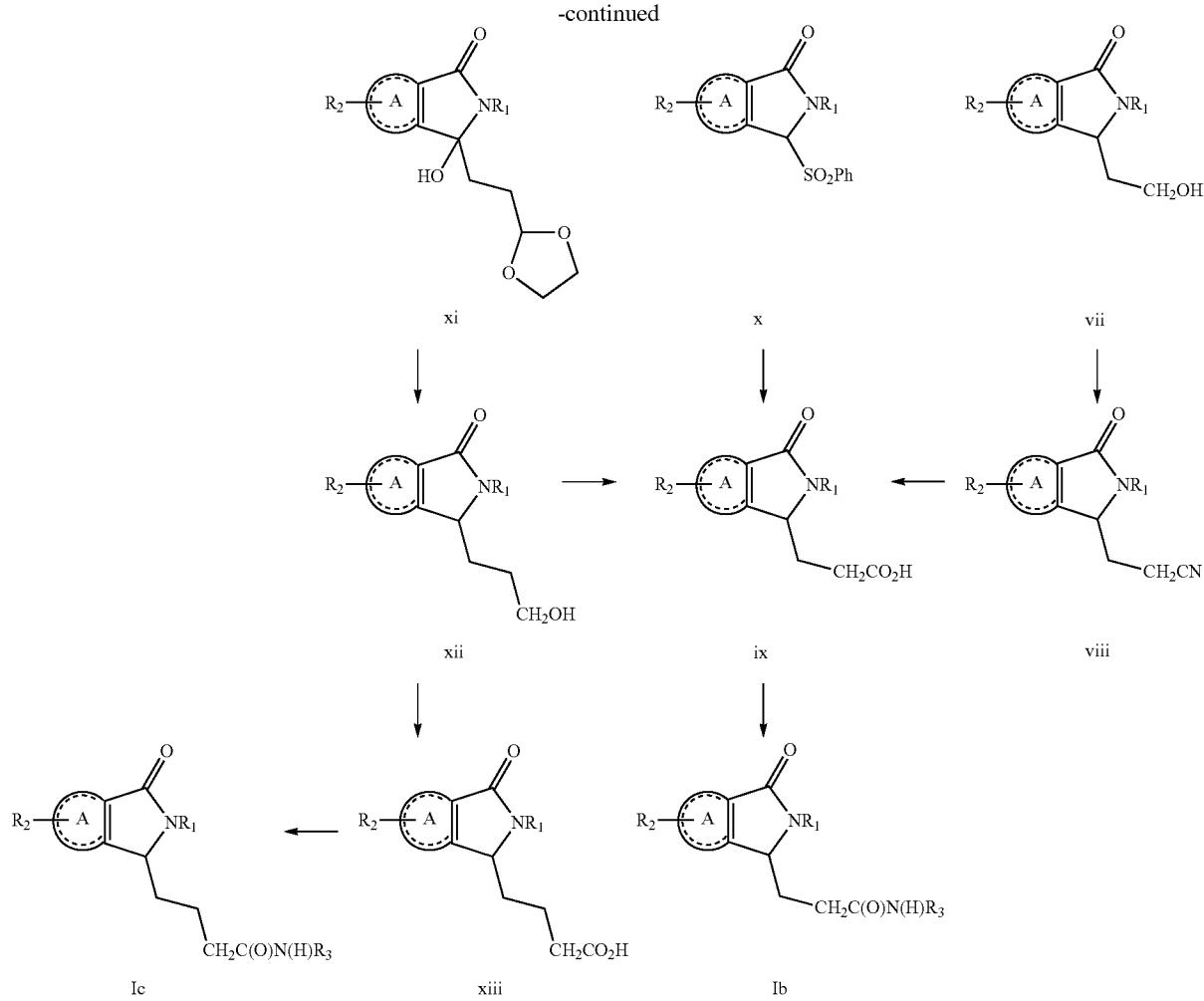

Compounds of Formulae Ia, Ib and Ic, wherein $R_3$ represents

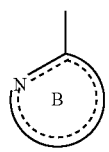

and A, B, $R_1$, and $R_2$ are as described above, can be prepared as shown in Scheme I. The appropriately substituted phthalimides of Formula iii can be obtained by alkylating commercially available phthalimides of Formula ii with an alkylating agent such as a substituted benzyl bromide and a base like potassium carbonate or sodium carbonate in a solvent such as dimethylformamide or acetone, at temperatures ranging for ambient to 80° C. The phthalimides of Formula iii can also be prepared by the addition of substituted primary amines to commercially available substituted phthalic anhydrides of Formula i using acetic acid as a solvent or with a co-solvent such as toluene and heating at temperatures between 80° C. and 100° C. The substituted phthalimides of Formula iii can then be reduced with sodium borohydride in an alcoholic solvent or with lithium borohydride in THF at temperatures between −30° C. and 0° C. in the presence of a Lewis acid such as cerium(III) chloride heptahydrate to provide compounds of Formula v. Alternatively, compounds of Formula v can be prepared by a regioselective lithiation (nBuLi)-electrophilic substitution (Me₂N—CHO) sequence of the benzanilines of Formula iv, which can be synthesized by coupling substituted primary amines to readily available substituted benzoic acid or acid chloride, as described by Epstajn, J. (Tetrahedron 1993, 929). A Wittig type condensation with ethoxycarbonylmethylidenetriphenylphosphorane followed by an alkaline hydrolysis then acidic treatment as described by A. Chihab-Eddine and B. Daich et. al. (*Heterocycles* 2002, 58,449-456) affords the acetic acid intermediate of Formula vi. Compounds of Formula vi can be converted to the acid chloride with reagents such as thionyl chloride or oxalyl chloride in a chlorinated solvent such as dichloromethane then treated with a base such as pyridine, 2,6-lutidine or diisopropylethylamine and the selected substituted amines of the formula $R_3NH_2$ at temperatures ranging from 0° C. to ambient to afford compounds of Formula Ia. Alternatively compounds of Formula vi can be treated with coupling agents such as 1-(3-dimethylaminopropyl)-3-ethylcarbodiimide hydrochloride (EDCI) or O-(7-Azabenzotriazol-1-yl)-N,N,N',N'-tetramethyluronium hexafluorophosphate (HATU) followed by the addition of substituted amines of the formula $R_3NH_2$ and a base such as triethylamine or diisopropylethylamine to provide compounds of Formula Ia.

Homologation of compounds of Formula vi can be accomplished by an initial diborane reduction of the carboxylic acid to the primary alcohol of Formula vii followed by treatment with methansulfonyl chloride in a chlorinated solvent (such as dichloromethane) in the presence of a base such as triethylamine to provide an intermediate mesylate. This intermediate can be subsequently heated at 60-70° C. with either potassium cyanide or sodium cyanide in a solvent such as DMF or hydrated ethanol to afford compounds of Formula viii. Hydrolysis of the nitrile of Formula viii under either basic conditions using 6N sodium hydroxide in an alcoholic solvent or under acidic conditions using 6N aqueous HCl produces compounds of Formula ix.

Alternatively compounds of Formula ix can be prepared by an initial Grignard addition of (1,3-dioxolan-2-ylethyl)magnesium bromide using standard conditions known in the art, to the substituted phthalimides of Formula iii to produce compounds of Formula xi. This procedure is then followed by a triethylsilane/borontriflouride diethyl etherate reduction affording compounds of Formula xii that can then be oxidized using either Jones reagent or a sodium chlorite/sodium hypochlorite solution containing a catalytic amount of TEMPO in a solvent such as acetonitrile to provide compounds of Formula ix.

Compounds of formula ix can also be prepared from compounds of Formula v by following the modified procedure established by Luzzio F. A. et al (Tetra. Lett. 1998, 2285). Hydroxylactam of Formula v can be treated with thiophenol in a solvent such as dichloromethane or a co-solvents system such as dichloromethane/dimethylformamide using a catalytic amount of p-toluenesulfonic or trifluoroacetic acid to provide the phenylthiolactam, which can then be oxidized to the corresponding benzylic sulfone of Formula x using m-chloroperbenzoic acid in dichloromethane. Compounds of Formula x can be deprotonated with a base such as NaH or LDA in THF/HMPA (4:1). Michael addition of the anion generated from compounds of Formula x with methyl acrylate followed by desulfonylation using Raney nickel in ethanol provides the methylester, which can then be hydrolyzed, to give the corresponding carboxylic acid of Formula ix. Addition of compounds of formula $NH_2R_3$ to compounds of Formula ix using the conditions described above provides compounds of Formula Ib. Furthermore, compounds of formula xii can be homologated as described above to afford compounds of formula xiii then be further treated with substituted amines of the formula $R_3NH_2$ to produce compounds of formula Ic.

Scheme II

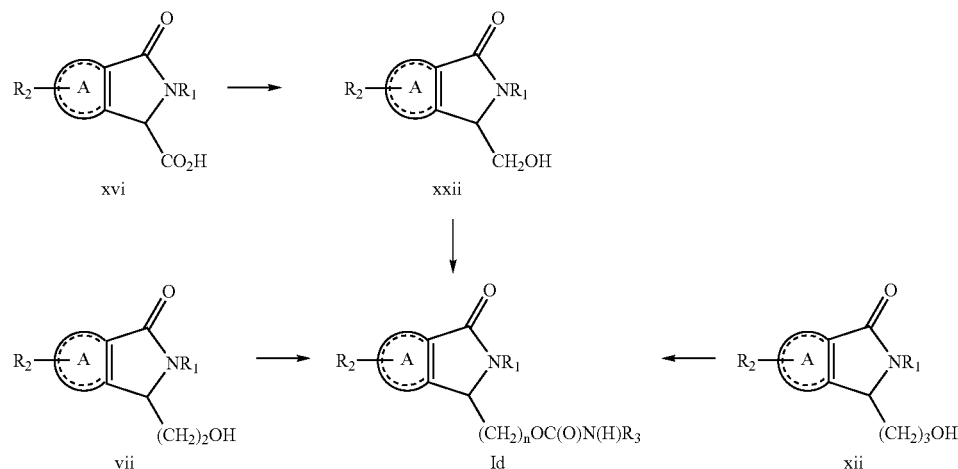

Compounds of formula Id wherein n is 1-3 and A, $R_1$, $R_2$ and $R_3$ are as described above can be prepared as shown in Scheme II. Reduction of compounds of Formula xvi using an appropriate base such as a borane in tetrahydrofuran complex solution at temperatures between 0° C. and ambient could provide compounds of formula xxii. Compounds of Formula vii, xii, or xxii can be treated directly with isocyanates of the formula $R_3NCO$ in a solvent such as toluene at refluxing temperature to provide compounds of formula Id.

Scheme III

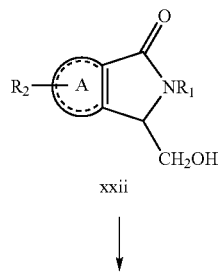

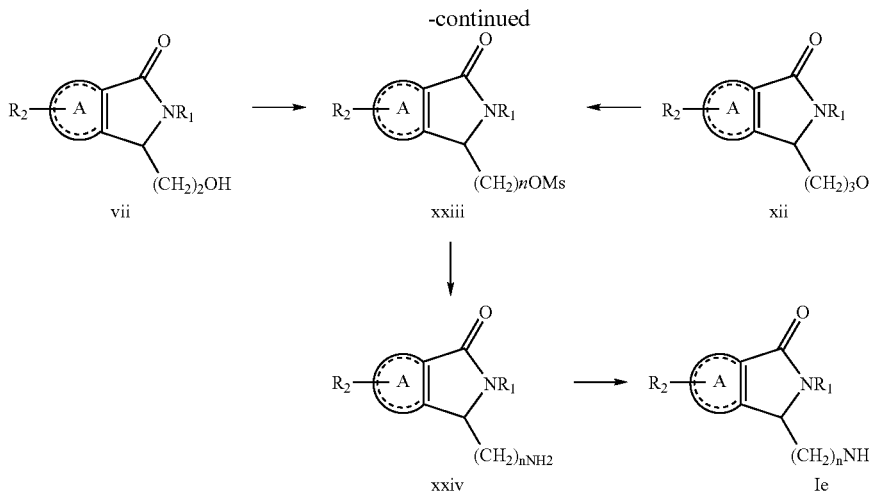

Compounds of Formula vii, xii, or xxii can also be converted to compounds of Formula Ie, wherein n is 1-3 and A, $R_1$, $R_2$ and $R_3$ are as described above, as shown in Scheme III. Compounds of Formula vii, xii, or xxii can be treated with methanesulfonyl chloride to form the mesylate of Formula xxiii using methods previously described. Compounds of Formula xxiii can then be converted to primary amines of Formula xxiv by formation of an intermediate azide using experimental procedures known in the art followed by a reduction step using palladium catalyzed hydrogenation. These primary amines of Formula xxiv can be treated with isocyanates of formula $R_3NCO$ as previously described or with amines of the formula $R_3NH_2$ in the presence of carbonyldiimidazole and a base such as DMAP at temperatures in the range of 60 to 100° C. to provide compounds of Formula Ie.

Scheme IV

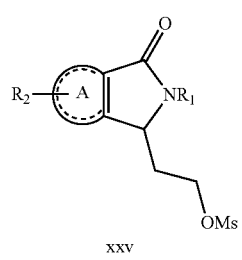
xxv

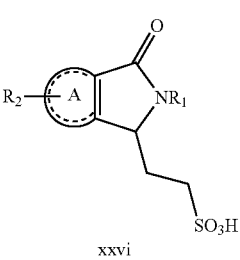
xxvi

-continued

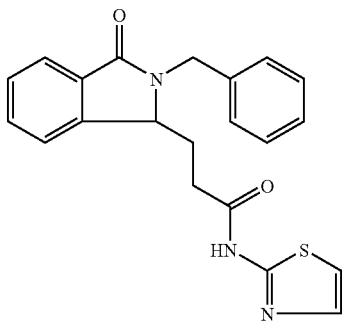 [SMILES: O=C(CCC1c2ccccc2C(=O)N1Cc1ccccc1)Nc1nccs1]
If

Compounds of Formula If wherein A, $R_1$, $R_2$ and $R_3$ are as described above can be prepared as shown in Scheme IV. The intermediate mesylate of Formula xxv prepared by treatment of compounds of Formula vii with methanesulfonyl chloride can be treated with sodium sulfite in hydrated ethanol at temperatures between ambient and 80° C. to provide the sulfonic acids of Formula xxvi. The compounds of Formula xxvi can be further treated with oxalyl chloride as previously described then reacted with substituted amines of formula $R_3NH_2$ to provide compounds of Formula If.

EXAMPLES

Example 1

3-(2-Benzyl-3-oxo-2,3-dihydro-1H-isoindol-1-yl)-N-thiazol-2-yl-propionamide

A. (2-Benzyl-3-oxo-2,3-dihydro-1H-isoindol-1-yl)-acetic acid benzyl ester (3-Oxo-2,3-dihydro-1H-isoindol-1-yl)-acetic acid (100 mg, 0.52 mmol) was dissolved in 2 mL dry DMF and stirred under $N_2$ at 0° C. NaH (44 mg, 1.1 mmol) was added and stirring continued for 0.5 h. Benzyl bromide (0.13 mL, 1.1 mmol) was added, the mixture was warmed to room temperature and stirred for 3 h. The mixture was diluted with EtOAc. The organic phase was washed with 2×10 mL aq LiCl and 10 mL brine, then dried ($MgSO_4$), filtered and evaporated. The title compound was purified by silica gel chromatography (102 mg, 53%).

B. 2-Benzyl-3-(2-hydroxyethyl)-2,3-dihydro-isoindol-1-one

The product from Part A (800 mg, 2.2 mmol) was dissolved in 6 mL methanol. 2M $LiBH_4$ in THF (6.5 mL) was added dropwise. The mixture was stirred at room temperature for 0.5 h, then at 70° C. for 16 h. The mixture was cooled to room temperature and diluted with 1 N HCl to pH 2. EtOAc was added, and the organic phase was washed with 1 N HCl, aq. $NaHCO_3$, and brine. The organic phase was dried ($MgSO_4$), filtered and evaporated. The title compound was purified by silica gel chromatography (510 mg, 87%).

C. Methanesulfonic acid 2-(2-benzyl-3-oxo-2,3-dihydro-1H-isoindol-1-yl)-ethyl ester The product from Part B (218 mg, 0.82 mmol) was dissolved in $CH_2Cl_2$ and cooled to 0° C. Triethylamine (0.45 mL, 3.26 mmol) and methanesulfonyl chloride (0.063 mL, 0.82 mmol) were added, the mixture was warmed to room temperature and stirring continued for 0.5 h. The mixture was diluted with $CH_2Cl_2$, then washed with 1 N HCl and aq $NaHCO_3$. The organic phase was dried ($MgSO_4$), filtered and evaporated. The title compound was isolated as a brown oil (288 mg, quant).

D. 3-(2-Benzyl-3-oxo-2,3-dihydro-1H-isoindol-1-yl)-propionitrile

The product from Part C (288 mg, 0.83 mmol) was dissolved in 2 mL DMF. KCN (81 mg, 1.25 mmol) and $K_2CO_3$ were added and the mixture was stirred at 50° C. for 16 h. The mixture was cooled to room temperature, diluted with EtOAc, then washed with water, 10% aq. LiCl, and brine. The organic phase was dried ($MgSO_4$), filtered and evaporated. The title compound was purified by silica gel chromatography (158 mg, 69%).

E. 3-(2-Benzyl-3-oxo-2,3-dihydro-1H-isoindol-1-yl)-propionic acid

The product from Part D (50 mg, 0.18 mmol) was dissolved in ethylene glycol. 6.6 N aq. NaOH (0.1 ml, 0.66 mmol) was added and the mixture was stirred at 100° C. for 7 h. The mixture was cooled to room temperature, diluted with EtOAc, then washed with 1 N HCl and brine. The organic phase was dried ($MgSO_4$), filtered and evaporated. The title compound was isolated as a brown oil (50 mg, 94%).

F. 3-(2-Benzyl-3-oxo-2,3-dihydro-1H-isoindol-1-yl)-N-thiazol-2-yl-propionamide The product from Part E (50 mg, 0.17 mmol) in 1.5 mL DMF was stirred with HOBt (52 mg, 0.34 mmol), EDCI (48 mg, 0.25 mmol) and 2-aminothiazole (25 mg, 0.25 mmol) at room temperature for 16 h. The mixture was diluted with EtOAc and washed with 10% aq LiCl, and brine. The organic phase was dried ($MgSO_4$), filtered and evaporated. The title compound was purified by silica gel chromatography (40 mg, 62%). $^1$H NMR (300 MHz, DMSO): δ 11.84 (s, 1H), 7.75 (d, J=9 Hz, 1H), 7.60 (s, 1H), 7.50 (m, 1H), 7.41 (d, J=4 Hz, 1H), 7.32 (m, 5H), 7.17 (d, J=4 Hz, 1H), 5.11 (d, J=15 Hz, 1H), 4.58 (m, 1H), 4.33 (d, J=15 Hz, 1H), 2.38 (m, 2H), 2.10 (m, 1H), 1.86 (m, 1H). MS: m/z (MH$^+$) 378.

Example 2

6-[3-(2-Benzyl-3-oxo-2,3-dihydro-1H-isoindol-1-yl)-propionylamino]-nicotinic acid methyl ester

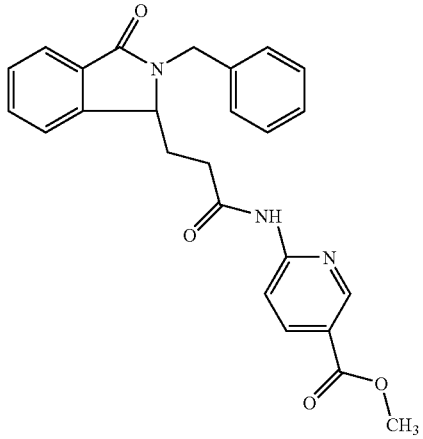 [SMILES: COC(=O)c1ccc(NC(=O)CCC2c3ccccc3C(=O)N2Cc2ccccc2)nc1]

The product from Example 1, Part E (200 mg, 0.68 mmol) was dissolved in 5 mL DMF. HOBt (312 mg, 2.04 mmol) and EDCI (340 mg, 2.04 mmol) were added and the mixture was stirred at room temperature for 0.5 h. 6-Aminonicotinic acid methyl ester (156 mg, 1.02 mmol) was added and the mixture was stirred for 16 h. The mixture was poured into 100 mL sat'd $NaHCO_3$ and extracted with EtOAc. The combined organic phase was washed with water and brine, then dried ($Na_2SO_4$), filtered and evaporated. The product was purified by silica gel chromatography (10 mg, 3%). $^1$H NMR (300 MHz, acetone-$d_6$) δ 9.64 (br s, 1H), 8.78 (s, 1H), 8.26 (s, 2H), 7.78 (d, J=7 Hz, 1H), 7.62 (m, 2H), 7.51 (m, 1H), 7.34 (m, 5H), 5.25 (d, J=15 Hz, 1H), 4.64 (m, 1H), 4.39 (d, J=15 Hz, 1H), 3.89 (s, 3H), 2.51 (m, 2H), 2.21 (m, 1H), 2.01 (m, 1H). MS: m/z (MH+) 430.

Example 3

3-(2-Benzyl-3-oxo-2,3-dihydro-1H-isoindol-1-yl)-N-pyridin-2-yl-propionamide

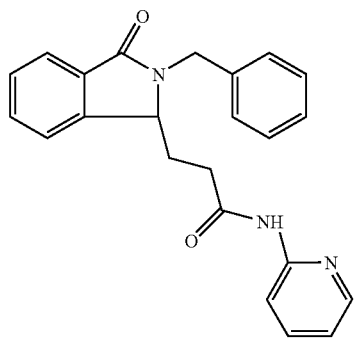 [SMILES: O=C(CCC1c2ccccc2C(=O)N1Cc1ccccc1)Nc1ccccn1]

The product from Example 1, Part E (200 mg, 0.68 mmol) and 2-aminopyridine (95 mg, 1.02 mmol) were converted to the title compound in a manner analogous to the method described in Example 2 (10 mg, 4%). $^1$H NMR (300 MHz, acetone-$d_6$) δ 9.13 (br s, 1H), 8.02 (m, 2H), 7.63 (m, 2H), 7.48 (m, 3H), 7.20 (m, 5H), 6.91 (m, 1H), 5.13 (d, J=15 Hz, 1H), 4.48 (m, 1H), 4.24 (d, J=15 Hz, 1H), 2.35 (m, 2H), 1.84 (m, 2H). MS: m/z (MH+) 372.

Example 4

1-[2-(2-Benzyl-3-oxo-2,3-dihydro-1H-isoindol-1-yl)-ethyl]-3-thiazol-2-yl-urea

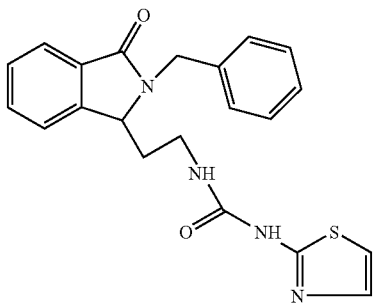 [SMILES: O=C(NCCC1c2ccccc2C(=O)N1Cc1ccccc1)Nc1nccs1]

A. 3-(2-Azidoethyl)-2-benzyl-2,3-dihydro-isoindol-1-one

The product from Example 1, Part B (2.0 g, 7.5 mmol), sodium azide (731 mg, 11.25 mmol), and $K_2CO_3$ (3.1 g, 225 mmol) were stirred in 20 mL DMF at 50° C. for 6 h. The mixture was poured into water and washed with EtOAc. The organic phase was washed with water and brine, then dried ($Na_2SO_4$), filtered and evaporated. The title compound was purified by silica gel chromatography (2.04 g, 93%).

B. 3-(2-Aminoethyl)-2-benzyl-2,3-dihydro-isoindol-1-one

The product from Part A (350 mg, 1.2 mmol), ammonium formate (525 mg), and 10% Pd/C (616 mg) in 5 mL MeOH was refluxed for 4 h. The mixture was filtered and evaporated. The title compound was purified by silica gel chromatography (250 mg, 78%).

C. 1-[2-(2-Benzyl-3-oxo-2,3-dihydro-1H-isoindol-1-yl)-ethyl]-3-thiazol-2-yl-urea The product from Part B (125 mg, 0.47 mmol) was dissolved in 4 mL dichloroethane. Carbonyl diimidazole (76 mg, 0.47 mmol) and DMAP (5 mg) were added and the mixture was heated to 80° C. for 2 h. The reaction was cooled to room temperature, and 2-aminothiazole was added (42 mg, 0.42 mmol) as a solution in 2 mL dichloroethane. The mixture was heated to 80° C. for 16 h, then cooled and evaporated. The title compound was purified by silica gel chromatography (44 mg, 24%). $^1$H NMR (300 MHz, CDCl$_3$) δ 10.34 (br s, 1H), 7.83 (d, J=7 Hz, 1H), 7.41 (m, 3H), 7.26 (m, 6H), 6.78 (dd, J=3 Hz, 1 Hz, 1H), 5.45 (d, J=15 Hz, 1H), 4.52 (m, 1H), 4.24 (d, J=15 Hz, 1H), 3.16 (m, 2H), 2.37 (m, 2H). MS: m/z (MH+) 393.

Example 5

6-[3-(2-Benzyl-3-oxo-2,3-dihydro-1H-isoindol-1-yl)-propionylamino]-nicotinic acid

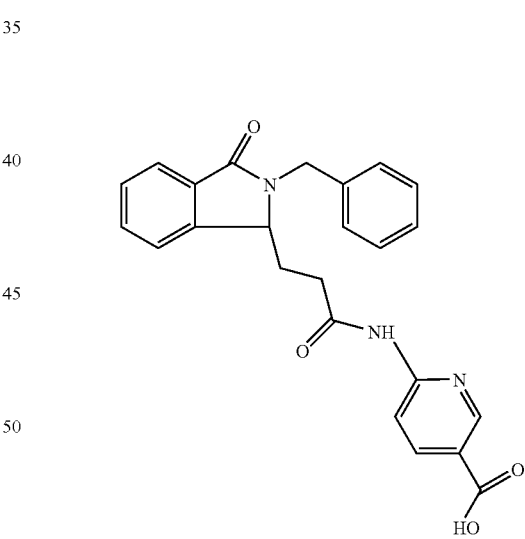

The product from Example 1, Part E (300 mg, 1.02 mmol) was taken up in 4 mL $CH_2Cl_2$ and cooled to 0° C. Oxalyl chloride (0.1 mL, 1.22 mmol) was added slowly and stirring continued for 0.5 h. A slurry of 6-aminonicotinic acid (211 mg, 1.53 mmol) and diisopropylethylamine (0.27 mL, 1.53 mmol) was added slowly and stirring continued at room temperature for 16 h. Three drops of conc. HCl was added and the organic phase was washed with brine. The organic phase was dried ($Na_2SO_4$), filtered and evaporated. The product was purified by silica gel chromatography (12 mg, 3%). $^1$H NMR (400 MHz, CDCl$_3$) δ 10.69 (s, 1H), 8.70 (m, 1H), 8.32 (m, 1H), 7.87 (m, 1H), 7.52 (m, 3H), 7.34 (m, 6H), 5.46 (m, 1H), 4.60 (br s, 1H), 4.31 (m, 1H), 2.54 (m, 2H), 2.09 (m, 2H). MS: m/z (MH+) 416.

Example 6

6-{2-[2-(4-Fluoro-benzyl)-3-oxo-2,3-dihydro-1H-isoindol-1-yl]-acetylamino}-nicotinic acid

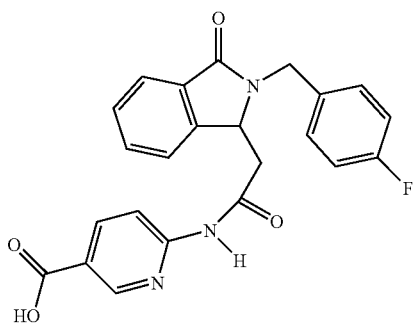 [SMILES: O=C(CC1c2ccccc2C(=O)N1Cc1ccc(F)cc1)Nc1ccc(C(=O)O)cn1]

A. (3-Oxo-2,3-dihydro-1H-isoindol-1-yl)-acetic acid methyl ester

To a solution of (3-oxo-2,3-dihydro-1H-isoindol-1-yl)-acetic acid (2.0 g, 10.4 mmol) in 100 mL methanol was added 2 mL conc. $H_2SO_4$ over 5 min. The mixture was stirred at room temperature for 16 h. Solvent was evaporated, the crude oil was dissolved in 200 mL EtOAc, then washed with 50 mL sat'd $NaHCO_3$ and 2×50 mL water. The organic phase was dried ($Na_2SO_4$), filtered, and solvent was evaporated. The title compound was isolated as a yellow oil (2.1 g, 98%).

B. [2-(4-Fluorobenzyl)-3-oxo-2,3-dihydro-1H-isoindol-1-yl]-acetic acid methyl ester The product from Part A (1.09 g, 4.9 mmol) was dissolved in 40 mL dry DMF and cooled to 0° C. under $N_2$. NaH (146 mg, 6.1 mmol) was added in one portion and stirring continued for 0.5 h. 4-Fluorobenzyl bromide (1.15 g, 6.1 mmol) was added and stirring continued for 16 h at room temperature. The reaction was cooled to 0° C., diluted with 200 mL EtOAc, and poured into 100 ml ice water. The organic phase was extracted with 3×100 mL water, dried ($Na_2SO_4$), filtered, and solvent was evaporated. The title compound was isolated as a white solid (1.77 g, impure).

C. [2-(4-Fluorobenzyl)-3-oxo-2,3-dihydro-1H-isoindol-1-yl]-acetic acid

The product from Part B (200 mg, 0.64 mmol) was dissolved in 10 mL THF. LiOH (200 mg, 8.3 mmol) in 5 mL water was added, and the mixture was stirred overnight at room temperature. The mixture was diluted with 1 N HCl and extracted with EtOAc. The organic phase was dried ($Na_2SO_4$), filtered, and solvent was evaporated. The title compound was isolated as an oil (160 mg, 84%).

D. 6-{2-[2-(4-Fluorobenzyl)-3-oxo-2,3-dihydro-1H-isoindol-1-yl]-acetylamino}-nicotinic acid The product from Part C (140 mg, 0.47 mmol) was dissolved in 15 mL dry THF. HATU (267 mg, 0.7 mmol) was added, followed by triethylamine (0.26 mL, 1.9 mmol). The mixture was stirred for 1 h and turned yellow. Trimethylsilyl 6-aminonicotinate (150 mg, 0.7 mmol) was added, followed by triethylamine (0.26 mL, 1.9 mmol), and the mixture was stirred at room temperature for 16 h. Solvent was evaporated, the residue was taken up in 100 mL EtOAc and washed with 2×15 mL 2N HCl and 2×50 mL water. The organic phase was dried ($Na_2SO_4$), filtered, and solvent was evaporated. The product was purified by silica gel chromatography (65 mg, 33%). 6-{2-[2-(4-Fluorobenzyl)-3-oxo-2,3-dihydro-1H-isoindol-1-yl]-acetylamino}-nicotinic acid: $^1$H NMR (400 MHz, DMSO) δ 10.89 (s, 1H), 8.79 (s, 1H), 8.25 (d, J=8 Hz, 1H), 8.15 (d, J=8 Hz, 1H), 7.75 (d, J=7 Hz, 1H), 7.57 (m, 3H), 7.28 (m, 2H), 7.07 (t, J=9 Hz, 2H), 4.93 (m, 2H), 4.50 (d, J=15 Hz, 1H), 3.09 (dd, J=6 Hz, 16 Hz, 1H), 2.91 (dd, J=6 Hz, 16 Hz, 1H). MS: m/z (MH$^+$) 420.

Example 7

6-{3-[2-(4-Fluoro-benzyl)-3-oxo-2,3-dihydro-1H-isoindol-1-yl]-propionylamino}-nicotinic acid

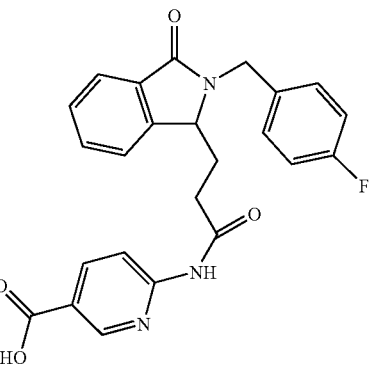

A. 2-(4-Fluorobenzyl)-isoindole-1,3-dione

4-Fluorobenzylamine (20 g, 160 mmol) in 10 mL $CH_2Cl_2$ was added to phthalic anhydride (5 g, 34 mmol) in 20 mL glacial acetic acid. The reaction was stirred at 100° C. for 4 h as water was collected with a Dean-Stark trap. Solvent was evaporated and the product was obtained by crystallization from ethanol (7.5 g, 87%).

B. 3-(3-[1,3]Dioxolan-2-ylethyl)-2-(4-fluorobenzyl)-3-hydroxy-2,3-dihydroisoindol-1-one Mg metal (800 mg, 0.033 g·atoms) and 1-(2-Bromoethyl)-[1,3]dioxolane (426 mg, 2.4 mmol) in 50 mL THF were heated to 70° C. in a dry flask until approximately half of the magnesium was consumed. The product from Part A (3.0 g, 11.8 mmol), as a solution in THF, was added dropwise over 40 min. Stirring continued for 2 h, then the reaction was stopped by addition of aqueous ammonium chloride. The product was purified by silica gel chromatography (3.1 g, 83%).

C. 2-(4-Fluorobenzyl)-3-(3-hydroxypropyl)-2,3-dihydroisoindol-1-one

The product from Part B (3.5 g, 10 mmol) was dissolved in 100 mL $CH_2Cl_2$ and cooled to 0° C. under $N_2$. $BF_3 \cdot Et_2O$ (3.1 mL, 19 mmol) was added dropwise, followed by triethylsilane (1.6 mL, 19 mmol). The reaction was stirred for 2.5 h. The reaction was poured into ice and extracted with 2×150 mL CH$_2$Cl$_2$. The combined organic phase was washed with 50 mL aq. bicarb, 150 mL water, and 100 mL brine. The organic phase was dried (Na$_2$SO$_4$), filtered, and solvent was evaporated. The crude reaction product (14 g) was used in the next step without purification.

D. 3-[2-(4-Fluorobenzyl)-3-oxo-2,3-dihydro-1H-isoindol-1-yl]-propionic acid

The crude product from Part C (560 mg, 1.9 mmol) was dissolved in 5 mL acetone and cooled to 0° C. 4 mL Jones Reagent was added and the mixture was stirred at room temperature for 1.5 h. Solvent was evaporated, the residue was taken up in 15 mL ether and poured into ice water. The mixture was extracted with 50 mL CH$_2$Cl$_2$. The organics were combined, washed with 3×50 mL water, dried (Na$_2$SO$_4$), filtered, and evaporated to yield a brown oil (530 mg, 90%).

E. 6-{3-[2-(4-Fluorobenzyl)-3-oxo-2,3-dihydro-1H-isoindol-1-yl]-propionylamino}-nicotinic acid A solution of the product from Part D (300 mg, 0.96 mmol) was dissolved in 15 mL THF and stirred under N$_2$. HATU (728 mg, 1.9 mmol) was added and stirring continued for 0.5 h. Trimethylsilyl 6-aminonicotinate (150 mg, 0.77 mmol) was added, followed by triethylamine (0.53 mL, 3.8 mmol), and the mixture was stirred at room temperature for 16 h. Solvent was evaporated, the residue was taken up in 150 mL EtOAc and washed with 35 mL 2N HCl and 2×50 mL water. The organic phase was dried (Na$_2$SO$_4$), filtered, and solvent was evaporated. The final product was isolated by silica gel chromatography and crystallization from ethanol (100 mg, 24%). $^1$H NMR (300 MHz, DMSO) δ 10.65 (s, 1H), 8.76 (m, 1H), 8.09 (d, J=9 Hz, 1H), 7.72 (m, 1H), 7.59 (m, 2H), 7.49 (m, 2H), 7.35 (m, 2H), 7.14 (m, 2H), 5.05 (d, J=15 Hz, 1H), 4.57 (s, 1H), 4.37 (d, J=15 Hz, 1H), 2.35 (m, 2H), 2.10 (m, 1H), 1.86 (m, 1H). MS: m/z (MH$^+$) 434.

Example 8

6-{3-[2-(4-Methoxy-benzyl)-3-oxo-2,3-dihydro-1H-isoindol-1-yl]-propionylamino}-nicotinic acid

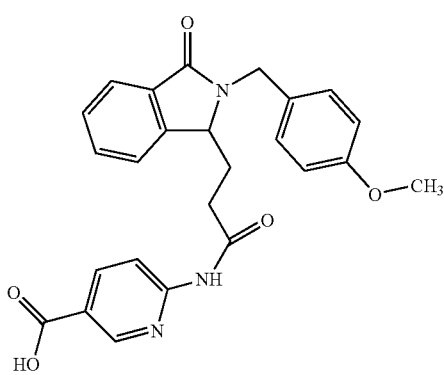 [SMILES: COc1ccc(CN2C(=O)c3ccccc3C2CCC(=O)Nc2ccc(C(=O)O)cn2)cc1]

A. 2-(4-Methoxybenzyl)-isoindole-1,3-dione

4-Methoxybenzylamine (4.9 g, 36 mmol) was added to phthalic anhydride (4.5 g, 30 mmol) in 15 mL glacial acetic acid. The reaction was stirred at 100° C. for 4 h as water was collected with a Dean-Stark trap. Solvent was evaporated and the product was obtained by crystallization from ethanol (7 g, 87%).

B. 3-(2-[1,3]Dioxolan-2-yl-ethyl)-3-hydroxy-2-(4-methoxybenzyl)-2,3-dihydroisoindol-1-one The product from part A (4.6 g, 17.2 mmol) was converted to the title compound by the method described in Example 7, Part B (6.0 g crude).

C. 3-(3-Hydroxypropyl)-2-(4-methoxybenzyl)-2,3-dihydroisoindol-1-one

The product from Part B (4 g, 10.8 mmol) was converted to the title compound by the method described in Example 7, Part C (700 mg, 23%).

D. 3-[2-(4-Methoxybenzyl)-3-oxo-2,3-dihydro-1H-isoindol-1-yl]-propionic acid The product from Part C (700 mg, 2.3 mmol) was converted to the title compound by the method described in Example 7, Part D (600 mg, 82%).

E. 6-{3-[2-(4-Methoxybenzyl)-3-oxo-2,3-dihydro-1H-isoindol-1-yl]-propionylamino}-nicotinic acid The product from Part D (300 mg, 0.92 mmol) was converted to the title compound by the method described in Example 6, Part D (100 mg, 24%). %). $^1$H NMR (300 MHz, DMSO) δ 10.66 (s, 1H), 8.76 (m, 1H), 8.50 (d, J=9 Hz, 1H), 8.20 (m, 1H), 7.73-7.46 (m, 5H), 7.25 (m, 2H), 6.89 (m, 2H), 5.06 (d, J=15 Hz, 1H), 4.50 (m, 1H), 4.26 (d, J=15 Hz, 1H), 3.68 (s, 3H), 2.32 (m, 2H), 1.81-1.39 (m, 2H). MS: m/z (MH$^+$) 446.

Example 9

6-{(3-[2-(4-Methoxy-benzyl)-3-oxo-2,3-dihydro-1H-isoindol-1-yl]-propionylamino}-nicotinic acid methyl ester

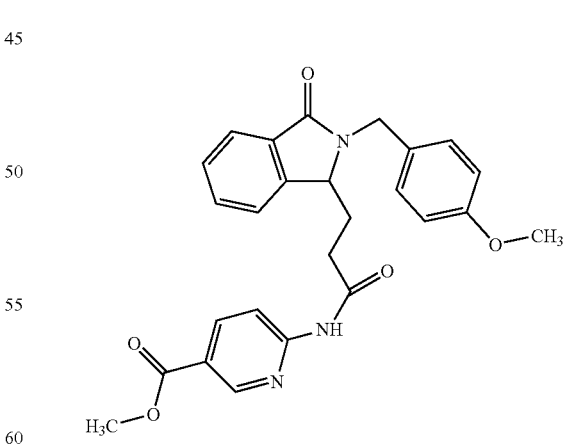

A. N-(4-methoxybenzyl)phthalimide

A mixture of phthalic anhydride (10 g, 0.067 mmol) and 4-methoxybenzylamine (9.7 ml, 0.074) in glacial acetic acid (60 ml) was stirred in a 90° C. oil bath for 2½ hr, cooled to room temperature and the excess acetic acid removed under reduced pressure. The residual mixture was diluted with water (50 ml) and poured slowly into a saturated NaHCO$_3$ solution (150 ml). The mixture was stirred at room temperature overnight and the precipitate collected by filtration, rinsing further with water. The precipitate was then dried under reduced pressure to provide a white solid product (15.7 g) 87%.

B. 3-Hydroxy-2-(4-methoxybenzyl)-2,3-dihydro-isoindol-1-one

A mixture of the phthalimide prepared in Part A (11.7 g, 0.044 mmol) and cerium(III) chloride heptahydrate in dry tetrahydrofuran (THF) (100 mL) was cooled to −30° C. (CO$_2$/acetonitrile bath) and lithium borohydride (22 ml, 2M solution in THF) was added dropwise maintaining internal reaction temperate at −30° C. After complete addition the reaction mixture was warmed to 0° C. and stirred at 0° C. for 4 hr. The reaction mixture was quenched with ice H$_2$O (150 mL), most of the THF was removed in-vacuo and stirring was continued overnight. The white solid precipitate was collected and dried under reduced pressure to afford the desired product (10 g) 85%.

C. [2-(4-Methoxy-benzyl)-3-oxo-2,3-dihydro-1H-isoindol-1-yl]-acetic acid

A mixture of the hydroxy isoindolone prepared in Part B (6.3 g, 0.023 mmol) and (carbethoxymethylene)-triphenylphosphorane (9.8 g, 28.1 mmol) in toluene (100 mL) was stirred at reflux for 24 hr, cooled to room temperature and evaporated in vacuo. The resulting oil was diluted with EtOH/H$_2$O (90/30 mL) and potassium carbonate (4.2 g, 30.4 mmol) was added. The reaction mixture was stirred at reflux for 16 hr, evaporated in vacuo, diluted with water (150 mL) and acidified with 6N HCl to pH 3. The aqueous mixture was stirred at RT for 16 hr and the solid precipitates collected and dried under reduced pressure to provide a white sold product (5.95 g) 82%.

D. 3-(2-Hydroxy-ethyl)-2-(4-methoxy-benzyl)-2,3-dihydro-isoindol-1-one

A borane tetrahydrofuran complex solution (9.5 ml, 1 M solution in THF) was added to a cold (0° C.) solution of the carboxylic acid prepared in Part C (1.98 g, 6.4 mmol) in dry tetrahydrofuran. The resulting reaction mixture was stirred a 0° C. for 2 hr and quenched with ice H$_2$O (60 ml). Stirring was continued for 30 minutes and the aqueous mixture extracted with ethyl acetate (1×60 mL). The ethyl acetate extract was washed with brine and dried over MgSO$_4$. The solvent was removed after filtration to provide the desired product as a pale yellow oil. (1.65 g) 87%.

E. Methanesulfonic acid 2-[2-(4-methoxy-benzyl)-3-oxo-2,3-dihydro-1H-isoindol-1-yl]-ethyl ester Methanesulfonyl chloride was slowly added to a cold (0° C.) solution of the hydroxylethyl isoindolone prepared in Part D (1.36 g, 4.6 mmol) and triethylamine (1.27 mL, 9.1 mmol) in dichloromethane (10 mL). The resulting solution was stirred at 0° C. for 2½ hr and ice water was added (40 mL). Dichloromethane (40 mL) was added and layers were separated. The CH$_2$Cl$_2$ layer was washed was washed with H$_2$O, brine, dried over MgSO$_4$ and evaporated in vacuo to afford the desired product (1.69 g) 98%.

F. 3-[2-(4-Methoxy-benzyl)-3-oxo-2,3-dihydro-1H-isoindol-1-yl]-propionitrile A mixture of the mesylate prepared in Part E (1.09 g, 2.9 mmol) and sodium cyanide (0.28 g, 5.8 mmol) in DMF (10 mL) was stirred in a 70° C. oil bath for 4 hr, poured into ice water (80 mL) and the product extracted out with ethyl acetate (2×80 mL). The combined ethyl acetate extracts were washed with brine, dried over MgSO$_4$ and filtered. Removal of solvent under reduced pressure provided the desired product as an amber oil (0.828 g) 93%.

G. 3-[2-(4-Methoxy-benzyl)-3-oxo-2,3-dihydro-1H-isoindol-1-yl]-propionic acid A 6N sodium hydroxide solution (1.3 mL) was added to the nitrile prepared in Part F (0.203 mg, 0.66 mmol) in methanol (10 mL). The resulting solution was stirred at reflux overnight, cooled to room temperature and the methanol removed under reduced pressure. Water (60 mL) was added and the mixture extracted with ethyl acetate (1×60 mL) to remove impurities. The aqueous layer was acidified with 6N HCl then extracted with EtOAc (1×60 mL). The EtOAc extract was washed with brine, dried over MgSO4, filtered and evaporated in vacuo to yield the desired product (0.2 g) 93%.

H. 6-{3-[2-(4-Methoxy-benzyl)-3-oxo-2,3-dihydro-1H-isoindol-1-yl]-propionylamino}-nicotinic acid methyl ester The title compound was prepared by the addition of O-(7-azabenzotriazol-1-yl)-N,N,N',N'-tetramethyluronium hexafluorophosphate (HATU) (0.326 g, 0.86 mmol) to a mixture of the carboxylic acid prepared in Part G (0.186 g, 0.57 mmol) in dichloromethane (4 mL). The mixture was stirred at room temperature for 15 minutes and 6-aminonicotinic acid methyl ester (0.087 g, 0.57 mmol) and triethylamine (0.24 mL, 1.7 mmol) were added. The resulting mixture was stirred at room temperature for 24 hr, evaporated in vacuo to remove dichloromethane. Ethyl acetate was added and the mixture extracted with H$_2$O (3×25 mL). The EtOAc extract was washed with brine, dried over MgSO$_4$, filtered and evaporated in vacuo to give a crude semi-solid. Purification by chromatography (hexane/ethyl acetate) afforded the desired product (0.086 g) 32%. $^1$HNMR (400 MHz, CDCL$_3$) δ 8.82 (s, 1H); 8.28 (d, J=8 Hz, 1H); 8.19 (d, J=8 Hz, 1H), 8.04 (broad s, 1H); 7.87 (d, J=7.6 Hz, 1H); 7.54-7.38 (m, 3H); 7.29 (d, J=8.8 Hz, 2H); 6.84 (d, J=8.4 Hz, 2H); 5.20 (d, J=14.8 Hz, 1H), 4.59 (m, 1H); 4.30 (d, J=15.2 Hz, 1H); 3.95 (s, 3H); 3.77 (s, 3H); 2.54-2.48 (m, 1H), 2.45-2.39 (m, 1H); 1.99-1.92 (m, 1H), 1.83-1.77 (m, 1H). MS: m/z (MH$^+$) 460.

Example 10

2-[2-(4-Methoxy-benzyl)-3-oxo-2,3-dihydro-1H-isoindol-1-yl]-ethanesulfonic acid thiazol-2-ylamide

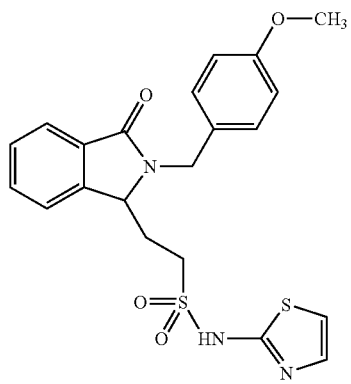 [SMILES: COc1ccc(CN2C(=O)c3ccccc3C2CCS(=O)(=O)Nc2nccs2)cc1]

A. 2-[2-(4-Methoxy-benzyl)-3-oxo-2,3-dihydro-1H-isoindol-1-yl]-ethanesulfonic acid A solution of sodium sulfite (1.2 g, 9.6 mmol) dissolved in water (14 mL) was added to a mixture of the mesylate prepared in Part E of Example 9 (0.8 g, 2.1 mmol) in ethanol (6 mL). The resulting mixture was stirred at reflux for 2 hr, cooled to room temperature and evaporated in vacuo to remove EtOH. The aqueous mixture was acidified to pH 3 and extracted with THF/EtOAc (9:1) several times. The combined organic extracts was dried over $MgSO_4$, filtered and evaporated in vacuo to provide the desired product as an off-white solid (0.48 g) 62.5%.

B. 2-[2-(4-Methoxy-benzyl)-3-oxo-2,3-dihydro-1H-isoindol-1-yl]-ethanesulfonic acid thiazol-2-ylamide Oxalyl chloride (0.3 mL, 0.6 mmol, 2M solution in $CH_2Cl_2$) was slowly added to a cold solution of the sulfonic acid prepared in Part A (0.15 g, 0.42 mmol) in dichloromethane (6 mL) containing two drops of dry DMF. The reaction mixture was warmed and stirred at room temperature for 4 hr. A mixture of 2-aminothiazole (0.046 g, 0.45 mmol) and triethylamine (0.17 mL, 1.2 mmol) in dichloromethane (2 mL) was then added dropwise and the resulting mixture stirred at room temperature overnight. Once quenched with $H_2O$ (30 mL), dichloromethane (25 mL) was added and the layers separated. The dichloromethane layer was dried over $MgSO_4$, filtered, and evaporated in vacuo to afford a crude semi-solid. Purification by chromatography provided the title compound as an off-white solid (0.068 g) 37%. $^1$HNMR (400 MHz, $CDCL_3$) δ 7.86 (d, J=7.7 Hz, 1H); 7.54-7.44 (m, 2H); 7.35 (d, J=7.6 Hz, 1H); 7.22 (d, J=8.6 Hz, 2H); 6.94 (d, J=4.8 Hz, 1H); 6.84 (d, J=8.5 Hz, 2H); 6.46 (d, J=4.9 Hz, 1H); 5.26 (d, J=14.5 Hz, 1H); 4.56 (m, 1H), 4.13 (d, J=15.22 Hz, 1H); 3.77 (s, 3H); 2.65-2.55 (m, 2H); 2.46-2.39 (m, 2H). MS: m/z ($MH^+$) 444.

Example 11

6-{3-[7-Fluoro-2-(4-fluoro-benzyl)-3-oxo-2,3-dihydro-1H-isoindol-1-yl]-propionylamino}-nicotinic acid

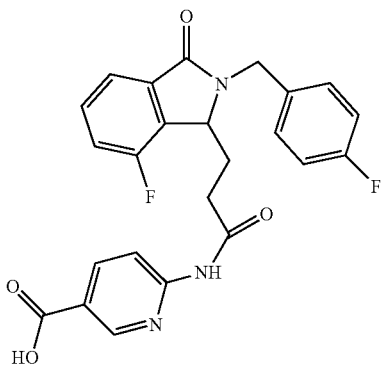 [SMILES: O=C(CCC1c2c(F)cccc2C(=O)N1Cc1ccc(F)cc1)Nc1ccc(C(=O)O)cn1]

A. 4-Fluoro-2-(4-fluoro-benzyl)-isoindole-1,3-dione

A mixture of 3-fluorophthalic anhydride (20 g, 120 mmol) and 4-fluorobenzylamine (20 g, 160 mmol) was stirred in 150 mL toluene. Glacial acetic acid (4 mL) was added dropwise, and the reaction was stirred at 110° C. Water was trapped with a Dean-Stark trap for 16 h. The reaction was cooled to 0° C. Product was isolated by filtration as an off-white solid, after washing with hexane. Obtain the title compound (34.3 g, quant.).

B. 3-(2-[1,3]Dioxolan-2-yl-ethyl)-4-fluoro-2-(4-fluorobenzyl)-3-hydroxy-2,3-dihydroisoindol-1-one Mg metal (1.0 g, 0.041 g·atoms) in 50 mL THF was heated to reflux in a dry flask for 10 min. 1-(2-Bromoethyl)-[1,3]dioxolane (1 mL, 5.5 mmol) was added and the mixture was stirred until Grignard formation began (warm solution). Additional 1-(2-bromoethyl)-[1,3]dioxolane (9 g, 50 mmol) in 50 mL THF was added dropwise over 40 min and stirred for 2 h. The product from Part A was added dropwise as a solution in 25 mL $CH_2Cl_2$. Stirring continued for 2 h, then the reaction was stopped by addition of aqueous ammonium chloride. Regioisomers were separated by silica gel chromatography. Obtained title compound (3.1 g, 41%) and 3-(2-[1,3]Dioxolan-2-yl-ethyl)-7-fluoro-2-(4-fluorobenzyl)-3-hydroxy-2,3-dihydroisoindol-1-one (500 mg, 6.5%).

C. 4-Fluoro-2-(4-fluorobenzyl)-3-(3-hydroxypropyl)-2,3-dihydroisoindol-1-one The product from Part B (13.2 g, 35 mmol) was dissolved in 350 mL $CH_2Cl_2$ and cooled to −78° C. Triethylsilane (11.9 mL, 140 mmol) was added dropwise, followed by $BF_3·Et_2O$ (5.65 mL, 35 mmol). The mixture was warmed to 0° C. and stirred for 3 h. The reaction was poured into ice and extracted with 3×100 mL $CH_2Cl_2$. The combined organic phase was washed with 200 mL aq. bicarb, 2×200 mL water, and 200 mL brine. The organic phase was dried ($Na_2SO_4$), filtered, and solvent was evaporated. The crude reaction product (14 g) was used in the next step without purification.

D. 3-[7-Fluoro-2-(4-fluorobenzyl)-3-oxo-2,3-dihydro-1H-isoindol-1-yl]-propionic acid The crude product from Part C (317 mg, 1 mmol) was dissolved in 5 mL acetone and added to 2 mL Jones Reagent at 0° C. The mixture was stirred at room temperature for 2.5 h, cooled to 0, and isopropanol was added dropwise until a blue/green color persisted. The mixture was diluted with 50 mL water and extracted with 2×60 mL EtOAc. The organics were combined, washed with 2×30 mL water, dried ($Na_2SO_4$), filtered, and evaporated to yield a yellow solid. The product was obtained as a white solid by crystallization from $CH_2Cl_2$ and ether (180 mg, 54%).

E. 6-{3-[7-Fluoro-2-(4-fluorobenzyl)-3-oxo-2,3-dihydro-1H-isoindol-1-yl]-propionylamino}-nicotinic acid The product from Part D (130 mg, 0.4 mmol) was dissolved in 15 mL $CH_2Cl_2$ and 15 mL THF. HOBt (60 mg, 0.4 mmol), HATU (224 mg, 0.6 mmol), and triethylamine (0.22 mL, 1.6 mmol) were added and the mixture was stirred for 1.5 h. Trimethylsilyl 6-aminonicotinate (200 mg, 0.95 mmol) was added and stirring continued for 16 h. The mixture was diluted with 10 mL 1 N HCl and extracted with 150 mL EtOAc. The organic phase was washed with 2×30 mL water and 2×30 mL brine, then dried ($Na_2SO_4$), filtered, and evaporated. Product was purified by silica gel chromatography (40 mg, 22%). $^1$H NMR (400 MHz, DMSO) δ 13.0 (broad s, 1H); 10.58 (s, 1H), 8.73 (d, J=2 Hz, 1H), 8.17 (dd, J=9 Hz, 2 Hz, 1H), 8.0 (d, J=9 Hz, 1H), 7.55 (m, 2H), 7.39 (m, 3H), 7.15 (t, J=9 Hz, 1H), 5.00 (d, J=15 Hz, 1H), 4.81 (s, 1H), 4.39 (d, J=15 Hz, 1H), 2.4 (m, 2H), 2.1 (m, 1H), 1.9 (m, 1H). MS: m/z (MH$^+$) 452.

Example 12

3-[7-Fluoro-2-(4-fluoro-benzyl)-3-oxo-2,3-dihydro-1H-isoindol-1-yl]-N-pyridin-2-vi-propionamide

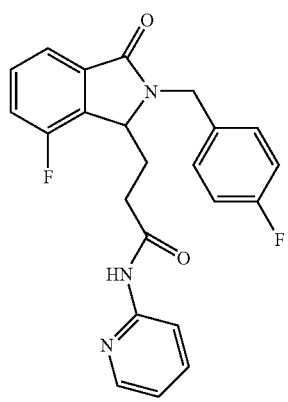 [SMILES: O=C(CCC1c2c(F)cccc2C(=O)N1Cc1ccc(F)cc1)Nc1ccccn1]

The product from Example 11, Part D (100 mg, 0.3 mmol) and 2-aminopyridine (43 mg, 0.45 mmol) were converted to the title compound in a manner analogous to the method described in Example 7, Part E, using $CH_2Cl_2$ in place of THF in the reaction and EtOAc in the workup, and without crystallization (39 mg, 32%). $^1$H NMR (300 MHz, CDCl$_3$) δ 8.11 (m, 3H), 7.67 (m, 2H), 7.44 (m, 1H), 7.31 (m, 2H), 7.19 (t, J=8 Hz, 1H), 7.00 (t, J=7 Hz, 3H), 5.28 (d, J=15 Hz, 1H), 4.69 (m, 1H), 4.22 (d, J=15 Hz, 1H), 2.54 (m, 2H), 1.96 (m, 2H). MS: m/z (MH$^+$) 408.

Example 13

3-[7-Fluoro-2-(4-fluoro-benzyl)-3-oxo-2,3-dihydro-1H-isoindol-1-yl]-N-pyrazin-2-yl-propionamide

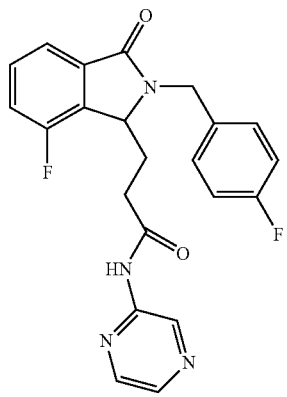 [SMILES: O=C(CCC1c2c(F)cccc2C(=O)N1Cc1ccc(F)cc1)Nc1cnccn1]

The product from Example 11, Part D (100 mg, 0.3 mmol) and pyrazin-2-ylamine (43 mg, 0.45 mmol) were converted to the title compound in a manner analogous to the method described in Example 7, Part E, using $CH_2Cl_2$ in place of THF in the reaction and EtOAc in the workup, and without crystallization (8 mg, 7%). $^1$H NMR (300 MHz, CDCl$_3$) δ 9.42 (s, 1H), 8.31 (d, J=3 Hz, 1H), 8.15 (m, 1H), 7.83 (s, 1H), 7.68 (d, J=8 Hz, 1H), 7.46 (m, 1H), 7.32 (m, 2H), 7.20 (t, J=9, 1H), 7.02 (t, J=7 Hz, 2H), 5.25 (d, J=15 Hz, 1H), 4.71 (m, 1H), 4.25 (d, J=15 Hz, 1H), 2.61 (m, 1H), 2.52 (m, 1H), 2.00 (m, 2H). MS: m/z (MH$^+$) 409.

Example 14

3-[7-Fluoro-2-(4-fluorobenzyl)-3-oxo-2,3-dihydro-1H-isoindol-1-yl]-N-(5-fluoro-pyridin-2-yl)-propionamide

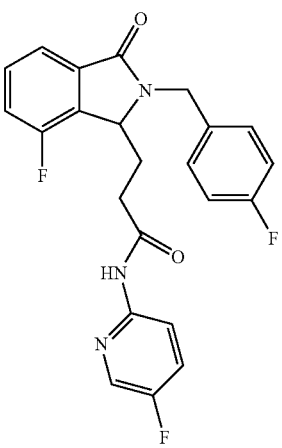 [SMILES: O=C(CCC1c2c(F)cccc2C(=O)N1Cc1ccc(F)cc1)Nc1ccc(F)cn1]

The product from Example 11, Part D (100 mg, 0.3 mmol) and 2-amino-5-fluoropyridine (110 mg, 0.45 mmol) were converted to the title compound in a manner analogous to the method described in Example 7, Part E, using 2; 1 THF/CH$_2$Cl$_2$ in place of THF in the reaction and EtOAc in the workup, and without crystallization (120 mg, 93%). $^1$H NMR (400 MHz, CDCl$_3$) δ 8.43 (s, 1H), 8.13 (m, 1H), 7.92 (d, J=3 Hz, 1H), 7.65 (d, J=8, 1H), 7.43 (m, 2H), 7.30 (m, 2H), 7.17 (t, J=9 Hz, 1H), 7.00 (t, J=9 Hz, 2H), 5.25 (d, J=15 Hz, 1H), 4.69 (m, 1H), 4.23 (d, J=15 Hz, 1H), 2.57 (m, 2H), 1.97 (m, 2H). MS: m/z (MH$^+$) 426.

Example 15

6-{3-[4-Fluoro-2-(4-fluoro-benzyl)-3-oxo-2,3-dihydro-1H-isoindol-1-yl]-propionylamino}-nicotinic acid

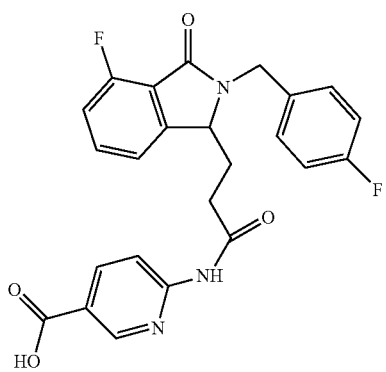 [SMILES: O=C(CCC1c2cccc(F)c2C(=O)N1Cc1ccc(F)cc1)Nc1ccc(C(=O)O)cn1]

A. 3-[4-Fluoro-2-(4-fluorobenzyl)-3-oxo-2,3-dihydro-1H-isoindol-1-yl]-propionic acid The title compound was obtained from 3-(2-[1,3]Dioxolan-2-yl-ethyl)-7-fluoro-2-(4-fluorobenzyl)-3-hydroxy-2,3-dihydroisoindol-1-one (Example 11, Part B) in a manner analogous to the method described in Example 11, Parts C and D.

B. 6-{3-[7-Fluoro-2-(4-fluorobenzyl)-3-oxo-2,3-dihydro-1H-isoindol-1-yl]-propionylamino}-nicotinic acid The product from Part A (90 mg, 0.27 mmol) was converted to the title compound in a manner analogous to the method described in Example 11, Part E (42 mg, 35%). $^1$H NMR (400 MHz, CD$_3$OD) δ 8.85 (s, 1H), 8.29 (d, J=9 Hz, 1H), 8.16 (d, J=9 Hz, 1H), 7.56 (m, 2H), 7.48 (m, 1H), 7.34 (m, 2H), 7.27 (d, J=8 Hz, 1H), 7.12 (t, J=9 Hz, 1H), 7.04 (m, 2H), 5.27 (d, J=15 Hz, 1H), 4.61 (s, 1H), 2.49 (m, 2H), 2.12 (m, 1H), 1.94 (m, 1H). MS: m/z (MH$^+$) 452.

Example 16

Pyridin-2-yl-carbamic acid 2-[7-fluoro-2-(4-fluorobenzyl)-3-oxo-2,3-dihydro-1H-isoindol-1-yl]-ethyl ester

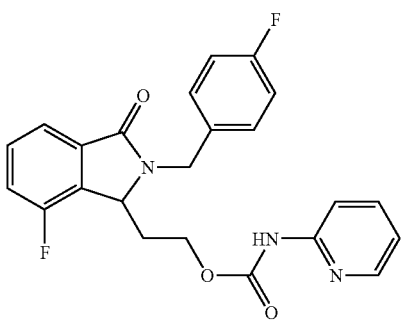 [SMILES: O=C(Nc1ccccn1)OCCC1c2c(F)cccc2C(=O)N1Cc1ccc(F)cc1]

A. 4-Fluoro-2-(4-fluoro-benzyl)-3-(2-hydroxyethyl)-2,3-dihydro-isoindol-1-one and 7-Fluoro-2-(4-fluoro-benzyl)-3-(2-hydroxy-ethyl)-2,3-dihydroisoindol-1-one The 3-Fluorophthalic anhydride and 4-fluorobenzylamine were substituted for phthalic anhydride and 4-methoxybenzylamine in Part A of Example 9 then subjected to the reaction conditions described in Part A through Part D to afford the desired product as a mixture of regioisomers.

B. Pyridine-2-carbonyl azide

Commercially available picolinoyl chloride hydrochloride (1 g, 5.6 mmol) was added to a cold (0° C.) solution of sodium azide (0.55 g, 8.4 mmol) in H$_2$O (2 mL). The mixture was stirred at 0° C. for 15 minutes then at room temperature for 2 hr. Saturated NaHCO$_3$ (20 mL) was added and the mixture extracted with ethyl acetate (1×25 mL). The ethyl acetate extract was washed with brine, dried over MgSO$_4$, filtered and evaporated in vacuo to afford a white solid acyl azide (0.26 g) 25%.

C. Pyridin-2-yl-carbamic acid 2-[7-fluoro-2-(4-fluoro-benzyl)-3-oxo-2,3-dihydro-1H-isoindol-1-yl]-ethyl ester The acyl azide prepared in Part B was dissolved in dry THF (20 mL) and heated to reflux for 1 hr. then cooled to room temperature. The mixture of regioisomers prepared in Part A (0.120 g, 0.396 mmol) dissolved in dry THF (5 mL) was then added. Toluene (10 mL) was added and the mixture stirred at reflux overnight. The resulting reaction mixture was cooled to room temperature and evaporated in vacuo to yield a crude mixture of regioisomers. Chromatography (EtOAc/hexane) provided the two regioisomers, the title compound and the title compound of Example 17. $^1$HNMR (400 MHz, CDCL$_3$) δ 8.22 (m 1H); 7.87 (d, J=8.3 Hz, 1H); 7.72-7.67 (m, 2H); 7.49-7.44 (m, 1H); 7.31-7.19 (m, 4H); 7.04-6.99 (m, 3H); 5.34 (d, J=15.2 Hz, 1H); 4.66 (m, 1H); 4.21 (d, J=15.4 Hz, 1H); 4.00-3.96 (m, 1H); 3.92-3.88 (m, 1H); 2.58-2.56 (m, 1H); 2.41-2.36 (m, 1H). MS: m/z (MH+) 423.

Example 17

Pyridin-2-yl-carbamic acid 2-[4-fluoro-2-(4-fluoro-benzyl)-3-oxo-2,3-dihydro-1H-isoindol-1-yl]-ethyl ester

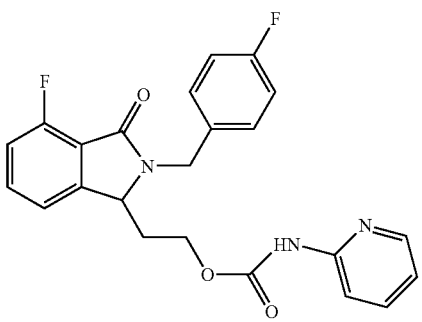 [SMILES: O=C(Nc1ccccn1)OCCC1c2cccc(F)c2C(=O)N1Cc1ccc(F)cc1]

Purification by chromatography (EtOAc/Hexane) of the crude mixture prepared in Example 16 provided the title compound together with the title compound of Example 16. ¹HNMR (400 MHz, CDCL₃) δ 8.22 (m, 1H); 7.89 (d, J=8.3 Hz, 1H); 7.70 (t, J=7.3 Hz, 1H); 7.53-7.46 (m, 1H); 7.44 (s, 1H), 7.32-7.28 (m, 2H); 7.21 (d, J=7.6 Hz, 1H); 7.09 (t, J=8.5 Hz, 1H), 7.03-6.97 (m, 3H), 5.35 (d, J=15.2 Hz, 1H); 4.66 (m, 1H); 4.25 (d, J=15.2 Hz, 1H); 4.00-3.96 (m, 1H); 3.92-3.88 (m, 1H); 2.58-2.56 (m, 1H); 2.41-2.36 (m, 1H). MS: m/z (MH+) 423.

Example 18

3-[4,7-Difluoro-2-(4-fluoro-benzyl)-3-oxo-2,3-dihydro-1H-isoindol-1-yl]-N-(5-trifluoromethyl-pyridin-2-yl)-propionamide

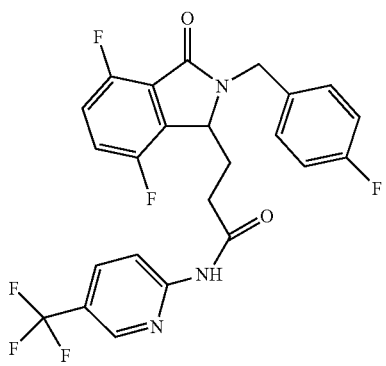 [SMILES: O=C(CCC1c2c(F)ccc(F)c2C(=O)N1Cc1ccc(F)cc1)Nc1ccc(C(F)(F)F)cn1]

A. 3-[4,7-Difluoro-2-(4-fluorobenzyl)-3-oxo-2,3-dihydro-1H-isoindol-1-yl]-propionic acid The title compound was synthesized from 4,7-difluorophthalic anhydride in a manner analogous to the method described in Example 11, Parts A-D.

B. 3-[4,7-Difluoro-2-(4-fluoro-benzyl)-3-oxo-2,3-dihydro-1H-isoindol-1-yl]-N-(5-trifluoromethyl-pyridin-2-yl)-propionamide The product from Part A (100 mg, 0.29 mmol) was converted to the title compound in a manner analogous to the method described in Example 11, Part E (70 mg, 49%). ¹H NMR (400 MHz, CDCl₃) δ 8.45 (s, 1H), 8.28 (d, J=9 Hz, 1H), 7.91 (dd, J=9 Hz, 2 Hz, 1H), 7.33 (m, 3H), 7.16 (m, 1H), 7.02 (m, 3H), 5.24 (d, J=15 Hz, 1H), 4.68 (s, 1H), 4.22 (d, J=15 Hz, 1H), 2.51 (m, 2H), 2.02 (m, 2H). MS: m/z (MH+) 494.

Example 19

Pyridin-2-yl-carbamic acid 2-(4-methoxy-benzyl)-3-oxo-2,3-dihydro-1H-isoindol-1-ylmethyl ester

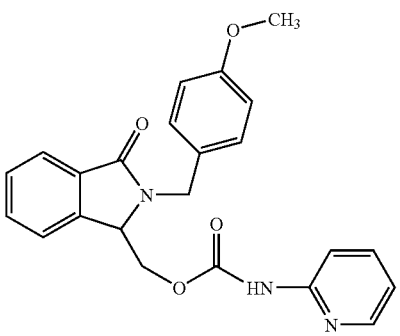 [SMILES: COc1ccc(CN2C(=O)c3ccccc3C2COC(=O)Nc2ccccn2)cc1]

A. 2-Ethoxycarbonylmethyl-benzoic acid ethyl ester

To a solution of homophthalic acid (5.07 g, 28.1 mmol) in DMF (30 mL) was added potassium carbonate (13.6 g, 98.5 mmol) and ethyl iodide (4.5 mL). The resulting mixture was stirred at room temperature overnight and poured into ice water (100 mL). After fifteen minutes of stirring the aqueous mixture was extracted with diethyl ether (2×). The combined ether extract was washed with brine, dried over MgSO₄ and concentrated under reduced pressure to provide the desired diethyl ester (3.7 g).

B. 2-(Bromo-ethoxycarbonyl-methyl)-benzoic acid ethyl ester

N-Bromosuccinamide (3.9 g, 22.2 mmol) was added to a solution of the compound prepared in Part A in carbon tetrachloride (20 mL). A catalytic amount of AIBN was added and the reaction mixture stirred at room temperature for 1 hr then at 70° C. for 16 hr. The mixture was cooled to room temperature, evaporated in vacuo and chromatographed (CH₂Cl₂/hexane) to provide pure product (3.8 g).

C. 2-(4-Methoxy-benzyl)-3-oxo-2,3-dihydro-1H-isoindole-1-carboxylic acid

The 4-methoxybenzyl amine (2.9 mL, 22.3 mmol) was slowly added to a cold (0° C.) solution of the compound prepared in Part B (3.5 g, 11.1 mmol) in acetonitrile ((40 mL). The mixture was stirred with slow warming to room temperature over a 16 hr. time period. The solid precipitates were removed by filtration and the mother liquor containing product evaporated under reduced pressure. The residual semisolid was diluted with EtOAc (60 ml), extracted with 1 N HCl (1×), saturated NaHCO₃ (1×) then brine and dried over MgSO₄. The solvent was removed under reduced pressure to provide the desired ester. Further hydrolyzes by the addition of an aqueous solution of NaOH (2 equiv.) to a solution of the ester in EtOH (50 mL). After 3 hr. of stirring at room temperature the ethanol was removed under reduced pressure. The residual semisolid was diluted with water and extracted with EtOAc. The aqueous extract containing product was acidified with hydrochloric acid and extracted with EtOAc (2×). The combined EtOAc extracts was dried over MgSO₄, filtered and evaporated in vacuo to afford the desired product (2.76 g).

D. 3-Hydroxymethyl-2-(4-methoxy-benzyl)-2,3-dihydro-isoindol-1-one

A borane tetrahydrofuran complex solution (18 ml, 1 M solution in THF) was added to a cold (0° C.) solution of the carboxylic acid prepared in Part C (2.7 g, 9.1 mmol) in dry tetrahydrofuran (40 mL). The resulting reaction mixture was stirred a 0° C. for 2 hr and quenched with ice H₂O (60 ml). Stirring was continued for 30 minutes and the aqueous mixture extracted with ethyl acetate (1×80 mL). The ethyl acetate extract was washed with brine and dried over MgSO₄. The solvent was removed after filtration and purified by chromatography to provide the desired product. (1.75 g) 68%.

E. Pyridin-2-yl-carbamic acid 2-(4-methoxy-benzyl)-3-oxo-2,3-dihydro-1H-isoindol-1-ylmethyl ester The acyl azide (263 g, 1.77 mmol) prepared in Part B of Example 16 was dissolved in dry tetrahydrofuran, heated with stirring at reflux for 1½ hr. Once cooled, a solution of the compound prepared in Part D (0. g, 0.396 mmol) dissolved in dry THF (5 mL) was then added. The resulting reaction mixture was stirred at reflux for 2 hr., cooled to room temperature, evaporated in vacuo and chromatographed (EtOAc/hexane) to provide the title compound (90 mg) 66%. ¹H NMR (400 MHz, CDCl₃) δ 8.14 (m, 1H); 7.91 (m, 2H); 7.82 (broad s, 1H); 7.69 (t, 7.1 Hz, 1H); 7.57-7.45 (m, 3H); 7.25 (d, J=8.5 Hz, 2H); 6.99-6.96 (m, 1H); 6.82 (d, J=8.7 Hz, 2H); 5.30 (d, J=15.3 Hz, 1H); 4.64-4.59 (m, 2H); 4.48-4.44 (m, 1H); 4.39 (d, J=15.1 Hz, 1H); 3.73 (s, 3H). MS: m/z (MH⁺) 404.

Example 20

6-{3-[4,7-Difluoro-2-(4-fluoro-benzyl)-3-oxo-2,3-dihydro-1H-isoindol-1-yl]-propionylamino}-nicotinic acid

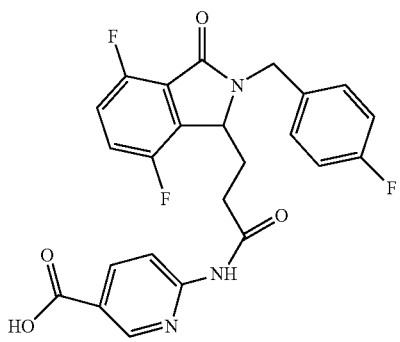 [SMILES: O=C(CCC1c2c(F)ccc(F)c2C(=O)N1Cc1ccc(F)cc1)Nc1ccc(C(=O)O)cn1]

The product from Example 18, Part A (100 mg, 0.29 mmol) was converted to the title compound in a manner analogous to the method described in Example 11, Part E (59 mg, 43%). ¹H NMR (300 MHz, DMSO) δ 8.73 (d, J=2 Hz, 1H), 8.17 (dd, J=9 Hz, 2 Hz, 1H), 7.99 (d, J=9 Hz, 1H), 7.38 (m, 5H), 7.15 (t, J=9 Hz, 2H), 4.95 (d, J=15 Hz, 1H), 4.82 (m, 1H), 4.36 (d, J=15 Hz, 1H), 2.38 (m, 2H), 1.91 (m, 2H). MS: m/z (MH⁺) 470.

Example 21

2-{3-[4,7-Difluoro-2-(4-fluoro-benzyl)-3-oxo-2,3-dihydro-1H-isoindol-1-yl]-propionylamino}thiazole-4-carboxylic acid ethyl ester

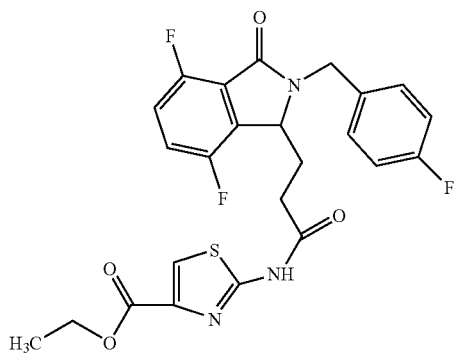 [SMILES: CCOC(=O)c1csc(NC(=O)CCC2c3c(F)ccc(F)c3C(=O)N2Cc2ccc(F)cc2)n1]

The product from Example 18, Part A (100 mg, 0.29 mmol) and ethyl 2-amino-1,3-thiazole-4-carboxylate were converted to the title compound in a manner analogous to the method described in Example 7, Part E without crystallization (80 mg, 55%). ¹H (300 MHz, CDCl₃) δ 10.31 (s, 1H), 7.77 (s, 1H), 7.28 (m, 2H), 7.12 (m, 1H), 6.99 (m, 3H), 5.21 (d, J=15 Hz, 1H), 4.65 (m, 1H), 4.32 (q, J=7 Hz, 2H), 4.12 (d, J=15 Hz, 1H), 2.57 (m, 2H), 2.14 (m, 1H), 2.08 (m, 1H), 1.35 (t, J=7 Hz, 3H). MS: m/z (MH⁺) 504.

Example 22

(2-{3-[4,7-Difluoro-2-(4-fluoro-benzyl)-3-oxo-2,3-dihydro-1H-isoindol-1-yl]-propionylamino}-thiazol-4-yl)-acetic acid

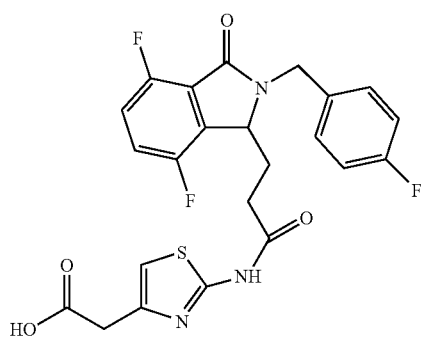 [SMILES: O=C(O)Cc1csc(NC(=O)CCC2c3c(F)ccc(F)c3C(=O)N2Cc2ccc(F)cc2)n1]

A. (2-{3-[4,7-Difluoro-2-(4-fluoro-benzyl)-3-oxo-2,3-dihydro-1H-isoindol-1-yl]-propionylamino}-thiazol-4-yl)-acetic acid ethyl ester The product from Example 18, Part A (100 mg, 0.29 mmol) and (2-amino-4-thiazolyl)acetic acid ethyl ester was converted to the title compound in a manner analogous to the method described in Example 7, Part E without crystallization (70 mg, 47%).

B. (2-{3-[4,7-Difluoro-2-(4-fluoro-benzyl)-3-oxo-2,3-dihydro-1H-isoindol-1-yl]-propionylamino}-thiazol-4-yl)-acetic acid The product from Part A (30 mg, 0.058 mmol) was dissolved in 10 mL THF. LiOH (7 mg, 0.18 mmol) in 5 mL water was added, and the mixture was stirred overnight at room temperature. The mixture was diluted with 1 N HCl and extracted with EtOAc. The organic phase was dried ($Na_2SO_4$), filtered, and solvent was evaporated. The title compound was isolated as an oil (20 mg, 70%). $^1$H NMR (300 MHz, DMSO) δ 12.27 (s, 1H), 11.91 (s, 1H), 7.38 (m, 4H), 7.15 (t, J=9 Hz, 2H), 6.89 (s, 1H), 4.94 (d, J=15 Hz, 1H), 4.82 (m, 1H), 4.33 (d, J=15 Hz, 1H), 3.56 (s, 2H), 2.40 (m, 2H), 2.03 (m, 1H), 1.91 (m, 1H). MS: m/z (MH$^+$) 490.

Example 23

2-{3-[7-Fluoro-2-(4-fluoro-benzyl)-3-oxo-2,3-dihydro-1H-isoindol-1-yl]-propionylamino}-isonicotinic acid ethyl ester

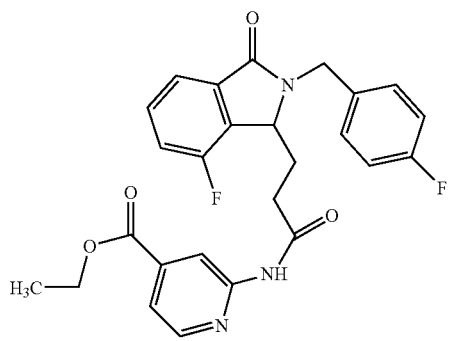 [SMILES: CCOC(=O)c1ccnc(NC(=O)CCC2c3c(F)cccc3C(=O)N2Cc2ccc(F)cc2)c1]

The product from Example 11, Part D (100 mg, 0.30 mmol) and 2-aminoisonicotinic acid ethyl ester (75 mg, 0.45 mmol) were converted to the title compound in a manner analogous to the method described in Example 7, Part E without crystallization (120 mg, 83%). $^1$H NMR (300 MHz, CDCl$_3$) δ 8.61 (s, 1H), 8.31 (d, J=5 Hz, 1H), 7.81 (s, 1H), 7.70 (d, J=8 Hz, 1H), 7.58 (dd, J=5 Hz, 1 Hz, 1H), 7.47 (m, 1H), 7.32 (m, 2H), 7.20 (t, J=9 Hz, 1H), 7.02 (t, J=9 Hz, 2H), 5.27 (d, J=15 Hz, 1H), 4.71 (m, 1H), 4.41 (q, J=7 Hz, 2H), 4.24 (d, J=15 Hz, 1H), 2.55 (m, 2H), 1.97 (m, 2H), 1.41 (t, J=7 Hz, 3H). MS: m/z (MH$^+$) 480.

Example 24

1-[2-(4-Methoxy-benzyl)-3-oxo-2,3-dihydro-1H-isoindol-1-ylmethyl]-3-pyridin-2-yl-urea

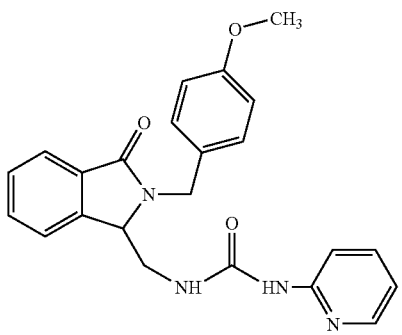 [SMILES: COc1ccc(CN2C(=O)c3ccccc3C2CNC(=O)Nc2ccccn2)cc1]

A. Methanesulfonic acid 2-(4-methoxy-benzyl)-3-oxo-2,3-dihydro-1H-isoindol-1-ylmethyl ester Methanesulfonyl chloride (0.52 ml, 6.7 mmol) was slowly added to a cold (0° C.) solution of the compound prepared in Part D of Example 19 (1.75 g, 6.2 mmol) and triethylamine (1.7 mL, 12.4 mmol) in dichloromethane (20 mL). The resulting solution was stirred at 0° C. for 2½ hr and ice water was added (60 mL). Dichloromethane (60 mL) was added and layers were separated. The CH$_2$Cl$_2$ layer was washed with H$_2$O, brine, dried over MgSO$_4$ and evaporated in vacuo to afford the desired product (2.2 g) 99%.

B. 3-Azidomethyl-2-(4-methoxy-benzyl)-2,3-dihydro-isoindol-1-one

A mixture of the compound prepared in Part A (2.3 g, 6.3 mmol) and sodium azide (0.83 g, 12.7 mmol) in DMF (8 mL) was stirred in a 80° C. oil bath for 2 hr., poured into ice water (50 mL) and extracted with ethyl acetate (2×50 ml). The combined EtOAc extracts were dried over MgSO$_4$, filtered, evaporated in vacuo and chromatographed (EtOAc/hexane) to yield the desired azide (0.98 g) 50%.

C. 3-Aminomethyl-2-(4-methoxy-benzyl)-2,3-dihydro-isoindol-1-one

The azide prepared in Part B (0.102 g, 0.33 mmol) was hydrogenated over 10% Pd/C in an H-cube apparatus to provide the desired amine (0.060 g) 64%.

D. 1-[2-(4-Methoxy-benzyl)-3-oxo-2,3-dihydro-1H-isoindol-1-yl methyl]-3-pyridin-2-yl-urea The acyl azide prepared in Part B of Example 16 was dissolved in dry tetrahydrofuran, heated with stirring at reflux for 1½ hr. Once cooled, a solution of the compound prepared in Part C (0.060 g, 0.21 mmol) dissolved in dry THF (5 mL) was then added. The resulting reaction mixture was stirred at reflux for 2 hr., cooled to room temperature, evaporated in vacuo and chromatographed (EtOAc/Hexane) to provide the title compound (9 mg) 10%. ¹HNMR (400 MHz, CDCl₃) δ 9.37 (s, 1H); 7.87 (d, J=7.5 Hz, 1H); 7.77-7.75 (m, 1H); 7.56-7.47 (m, 4H); 7.28 (m, 2H); 6.84-6.77 (m, 3H); 6.60 (d, J=8.3 Hz, 1H); 5.37 (d, J=14.9 Hz, 1H); 4.57 (m, 1H); 4.31 (d, J=15 Hz, 1H); 4.03 (m, 1H); 3.87 (m, 1H); 3.79 (s, 3H). MS: m/z (MH⁺) 403.

Example 25

2-{3-[4,7-Difluoro-2-(4-fluoro-benzyl)-3-oxo-2,3-dihydro-1H-isoindol-1-yl]-propionylamino}-thiazole-4-carboxylic acid

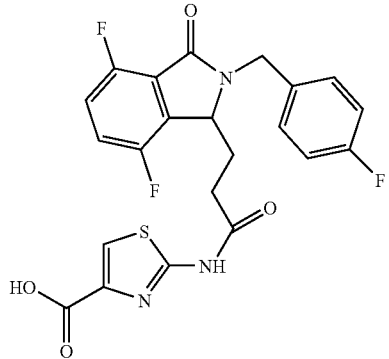 [SMILES: O=C(CCC1c2c(F)ccc(F)c2C(=O)N1Cc1ccc(F)cc1)Nc1nc(C(=O)O)cs1]

The product from Example 21 (30 mg, 0.059 mmol) was converted to the title compound in a manner analogous to the method described in Part B of Example 22 (15 mg, 53%). ¹H NMR (300 MHz, DMSO) δ 12.21 (br s, 1H), 7.92 (s, 1H), 7.40 (m, 4H), 7.15 (t, J=9 Hz, 2H), 4.93 (d, J=15 Hz, 1H), 4.83 (brs, 1H), 4.35 (d, J=15 Hz, 1H), 2.44 (m, 2H), 2.05 (m, 1H), 1.97 (m, 1H). MS: m/z (MH⁺) 476.

Example 26

6-{3-[7-Fluoro-2-(4-fluoro-benzyl)-3-oxo-2,3-dihydro-1H-isoindol-1-yl]-propionylamino}-nicotinic acid methyl ester

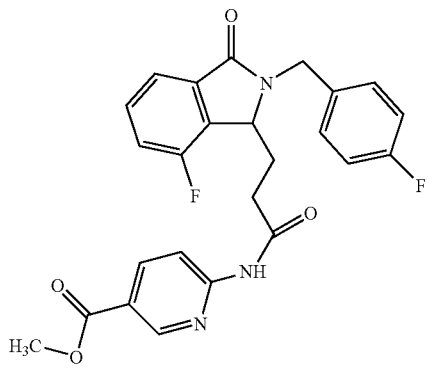 [SMILES: COC(=O)c1ccc(NC(=O)CCC2c3c(F)cccc3C(=O)N2Cc2ccc(F)cc2)nc1]

The product from Example 11, Part D (331 mg, 1 mmol) and 2-aminonicotinic acid methyl ester (316 mg, 2.1 mmol) were converted to the title compound in a manner analogous to the method described in Example 7, Part E without crystallization (269 mg, 58%). ¹H NMR (300 MHz, CDCl₃) δ 8.83 (d, J=2 Hz, 1H), 8.27 (dd, J=8 Hz, 2 Hz, 1H), 8.16 (d, J=9 Hz, 1H), 7.87 (br s, 1H), 7.69 (d, J=7 Hz, 1H), 7.46 (m, 1H), 7.31 (m, 2H), 7.20 (t, J=9 Hz, 1H), 7.02 (t, J=9 Hz, 2H), 5.25 (d, J=15 Hz, 1H), 4.70 (m, 1H), 4.25 (d, J=15 Hz, 1H), 3.92 (s, 3H), 2.52 (m, 2H), 1.98 (m, 2H). MS: m/z (MH⁺) 466.

Example 27

N-(5-Bromo-thiazol-2-yl)-3-[7-fluoro-2-(4-fluoro-benzyl)-3-oxo-2,3-dihydro-1H-isoindol-1-yl]-propionamide

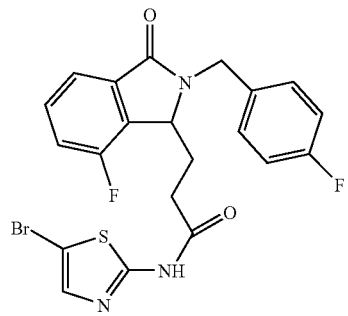 [SMILES: O=C(CCC1c2c(F)cccc2C(=O)N1Cc1ccc(F)cc1)Nc1ncc(Br)s1]

The title compound was prepared by slow addition of a 2M solution of oxalyl chloride to a cold solution of the intermediate carboxylic acid prepared in Part D of Example 11 (0.1 g, 0.302 mmol) in a solution of dry dichloromethane (4 mL) containing two drops of DMF. Stirring was continued at 0° C. for 1½ hr. The solvent was removed under reduced pressure and tetrahydrofuran (3 mL) was added while maintaining reaction temperature at 0° C. A solution of 2-amino-5-bromothiazole (0.054 g, 0.302 mmol) and pyridine (0.1 mL) in dry tetrahydrofuran (2 mL) was then slowly added and the reaction mixture allowed to warm to RT. Stirring was continued for an additional 3 hr and quenched with ice water (20 mL). A 1 N HCl solution (2 mL) was added and the aqueous mix extracted with ethyl acetate (2×25 mL). The combined ethyl acetate extracts was washed with brine, dried over MgSO₄, filtered and evaporated in vacuo. The crude product was purified by chromatography (EtOAc/hexane) to provide the title compound as a white solid (0.123 g) 83%. ¹HNMR (400 MHz, CDCl₃) δ 7.70 (d, J=7.74 Hz, 1H); 7.49 (m, 2H); 7.31-7.21 (m, 3H); 7.02-6.97 (m, 2H); 6.91 (s, 1H); 5.24 (d, J=14.9 Hz, 1H); 4.71 (m, 1H); 4.19 (d, J=15.08, 1H); 2.67-2.52 (m, 2H), 2.03-1.99 (m, 2H). MS: m/z (MH⁺) 492.

Example 28

3-[7-Fluoro-2-(4-fluoro-benzyl)-3-oxo-2,3-dihydro-1H-isoindol-1-yl]-N-quinolin-2-yl-propionamide

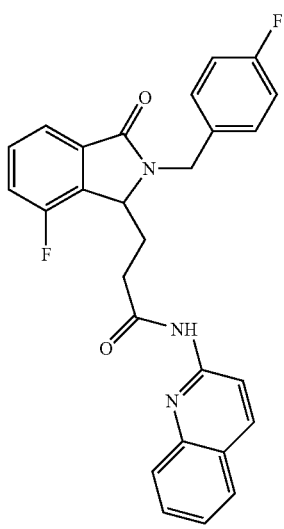 [SMILES: O=C(CCC1c2c(F)cccc2C(=O)N1Cc1ccc(F)cc1)Nc1ccc2ccccc2n1]

The product from Example 11, Part D (200 mg, 0.6 mmol) and quinolin-2-ylamine (131 mg, 0.91 mmol) were converted to the title compound in a manner analogous to the method described in Example 7, Part E, using CH$_2$Cl$_2$ in place of THF in the reaction and EtOAc in the workup, and without crystallization (220 mg, 80%). $^1$HNMR (400 MHz, CDCl$_3$) δ 8.87 (s, 1H), 8.46 (s, 1H), 8.09 (s, 1H), 7.87 (d, J=8 Hz, 1H), 7.80 (d, J=8 Hz, 1H), 7.66 (m, 2H), 7.48 (t, J=7 Hz, 1H), 7.41 (m, 1H), 7.32 (m, 2H), 7.16 (t, J=9 Hz, 1H), 7.01 (t, J=7 Hz, 2H), 5.30 (d, J=15 Hz, 1H), 4.71 (m, 1H), 4.25 (d, J=15 Hz, 1H), 2.59 (m, 2H), 1.98 (m, 2H). MS: m/z (MH$^+$) 458.

Example 29

3-[7-Fluoro-2-(4-fluoro-benzyl)-3-oxo-2,3-dihydro-1H-isoindol-1-yl]-N-isoquinolin-3-yl-propionamide

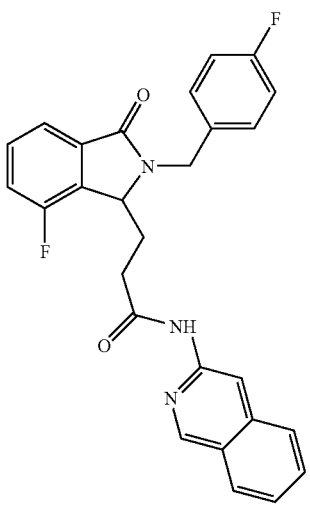 [SMILES: O=C(CCC1c2c(F)cccc2C(=O)N1Cc1ccc(F)cc1)Nc1cc2ccccc2cn1]

The product from Example 11, Part D (200 mg, 0.6 mmol) and isoquinolin-3-amine (131 mg, 0.91 mmol) were converted to the title compound in a manner analogous to the method described in Example 7, Part E, using CH$_2$Cl$_2$ in place of THF in the reaction and EtOAc in the workup, and without crystallization (95 mg, 35%). $^1$HNMR (300 MHz, CDCl$_3$) δ 8.28 (d, J=9 Hz, 1H), 8.15 (d, J=9 Hz, 1H), 7.91 (s, 1H), 7.75 (m, 2H), 7.70 (d, J=8 Hz, 1H), 7.64 (m, 1H), 7.45 (m, 2H), 7.32 (m, 2H), 7.20 (t, J=9 Hz, 1H), 7.02 (m, 2H), 5.29 (d, J=15 Hz, 1H), 4.71 (m, 1H), 4.26 (d, J=15 Hz, 1H), 2.55 (m, 2H), 2.00 (m, 2H). MS: m/z (MH$^+$) 458.

Example 30

3-[7-Fluoro-2-(4-fluoro-benzyl)-3-oxo-2,3-dihydro-1H-isoindol-1-yl]-N-(5methoxymethoxymethyl-pyridin-2-yl)-propionamide

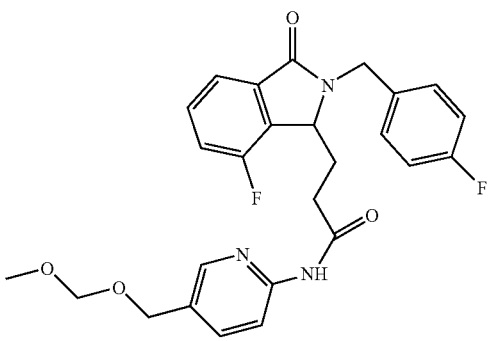 [SMILES: COCOCc1ccc(NC(=O)CCC2c3c(F)cccc3C(=O)N2Cc2ccc(F)cc2)nc1]

A. (6-Amino-pyridin-3-yl)-methanol

To a cold (0° C.) mixture of 6-Aminonicotinic acid methyl ester (0.511 g, 3.36 mmol) and Cerium(III) chloride heptahydrate (1.25 g, 3.36) in dry THF was slowly added lithium borohydride (8.4 mL, 1 M in THF) over a 30 minute period. The mixture was allowed to warm to room temperature overnight then slowly quenched by the addition of ice water (20 mL). After stirring for 1 hr the mixture was filtered through Celite diluted with EtOAc (30 mL) and layers were separated. The aqueous layer was further extracted with EtOAc (1×). The combined EtOAc extracts were washed with brine, dried over MgSO$_4$, evaporated in vacuo and provide a crude semi-solid. The white solid product was triturated with diethyl ether, filtered and dried under reduced pressure.

B. 5-Methoxymethoxymethyl-pyridin-2-ylamine

Bromomethyl methyl ether (0.25 mL, 3.06 mmol) was added dropwise to a cold (0° C.) solution of the compound prepared in Part A (0.222 g, 1.79 mmol) and N,N-diisopropylethylamine (0.47 mL, 2.68 mmol) in CH$_2$Cl$_2$ (10 mL). The resulting mixture stirred at 0° C. for 2½ hr, water was added and layers separated. The CH$_2$Cl$_2$ layer was dried over MgSO$_4$, filtered and evaporated in vacuo to give the desired MOM protected amino pyridine product.

C. 3-[7-Fluoro-2-(4-fluoro-benzyl)-3-oxo-2,3-dihydro-1H-isoindol-1-yl]-N-(5-methoxymethoxymethyl-pyridin-2-yl)-propionamide The title compound was prepared from the carboxylic acid prepared in Part D of Example 11 and the MOM protected amino pyridine prepared in Part B using the same procedure described in Example 28. ¹HNMR (400 MHz, CDCl₃) δ 8.19 (s, 1H); 8.11 (d, J=8.4 Hz, 1H); 7.75-7.67 (m, 2H); 7.47 (m, 1H); 7.34-7.29 (m, 2H); 7.24-7.18 (m 1H); 7.01 (t, J=8.6 Hz, 2H); 5.29 (d, J=15 Hz, 1H); 4.71 (s, 3H); 4.54 (s, 2H); 4.26 (d, J=15 Hz, 1H); 3.40 (s, 3H); 2.54 (m, 2H); 1.92 (m, 2H). MS: m/z (MH⁺) 482.

Example 31

3-[7-Fluoro-2-(4-fluoro-benzyl)-3-oxo-2,3-dihydro-1H-isoindol-1-yl]-N-(5-phenyl-pyridin-2-yl)-propionamide

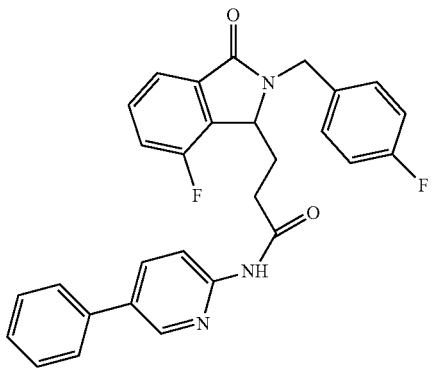 [SMILES: O=C(CCC1c2c(F)cccc2C(=O)N1Cc1ccc(F)cc1)Nc1ccc(-c2ccccc2)cn1]

The product from Example 11, Part D (331 mg, 1 mmol) and 5-phenylpyridin-2-ylamine (230 mg, 0.6 mmol) were converted to the title compound in a manner analogous to the method described in Example 7, Part E, using 1:1 THF/CH₃CN in place of THF, and without crystallization (108 mg, 74%). ¹H NMR (300 MHz, DMSO) δ 10.37 (s, 1H), 8.58 (s, 1H), 8.04 (s, 2H), 7.70 (m, 2H), 7.59 (m, 2H), 7.47 (m, 6H), 7.15 (t, J=9 Hz, 2H), 5.03 (d, J=15 Hz, 1H), 4.83 (m, 1H), 4.40 (d, J=15 Hz, 1H), 2.41 (m, 2H), 2.1 (m, 1H), 1.9 (m, 1H). MS: m/z (MH⁺) 484.

Example 32

N-(5-Bromo-pyridin-2-yl)-3-[7-fluoro-2-(4-fluoro-benzyl)-3-oxo-2,3-dihydro-1H-isoindol-1-yl]-propionamide

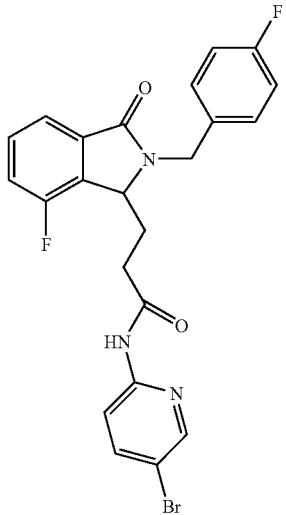 [SMILES: O=C(CCC1c2c(F)cccc2C(=O)N1Cc1ccc(F)cc1)Nc1ccc(Br)cn1]

The product from Example 11, Part D (150 mg, 0.45 mmol) and 5-bromopyridin-2-ylamine (78 mg, 0.45 mmol) were converted to the title compound in a manner analogous to the method described in Example 27 (151 mg, 69%). ¹H NMR (300 MHz, DMSO) δ 8.18 (d, J=2 Hz, 1H), 8.05 (m, 2H), 7.76 (dd, J=9 Hz, 3 Hz, 1H), 7.66 (d, J=7 Hz, 1H), 7.44 (m, 1H), 7.30 (m, 2H), 7.18 (t, J=9, 1H), 7.01 (t, J=7 Hz, 2H), 5.26 (d, J=15 Hz, 1H), 4.69 (m, 1H), 4.23 (d, J=15 Hz, 1H), 2.54 (m, 2H), 1.95 (m, 2H). MS: m/z (MH⁺) 486 (MH⁺ 2) 488.

Example 33

3-[7-Fluoro-2-(4-fluoro-benzyl)-3-oxo-2,3-dihydro-1H-isoindol-1-yl]-N-[5-(4-fluoro-Phenyl)-pyridin-2-yl]-propionamide

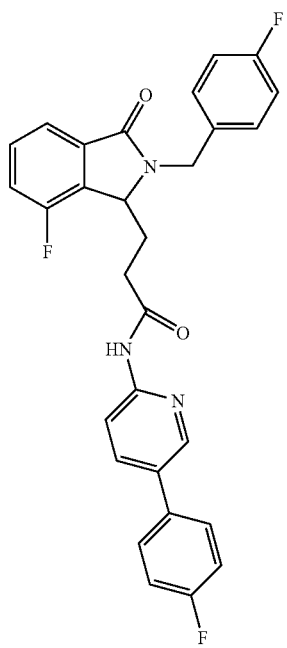 [SMILES: O=C(CCC1c2c(F)cccc2C(=O)N1Cc1ccc(F)cc1)Nc1ccc(-c2ccc(F)cc2)cn1]

The product from Example 50 (50 mg, 0.10 mmol) was dissolved in 10 mL DME. Pd(PPh₃)₄ (12 mg, 0.01 mmol) was added, followed by 4-fluorophenylboronic acid (29 mg, 0.2 mmol) and 2 M Na₂CO₃ (1 mL). The mixture was heated to 50 C for 4 h. The title compound was obtained from silica gel chromatography followed by crystallization from ether (21 mg, 41%). ¹H NMR (400 MHz, DMSO) δ8.37 (d, J=2 Hz, 1H), 8.16 (d, J=8 Hz, 1H), 7.85 (m, 2H), 7.68 (d, J=7, 1H), 7.49 (m, 3H), 7.33 (m, 2H), 7.15 (m, 3H), 7.02 (t, J=7 Hz, 2H), 5.28 (d, J=15 Hz, 1H), 4.71 (m, 1H), 4.25 (d, J=15 Hz, 1H), 2.56 (m, 2H), 1.99 (m, 2H). MS: m/z (MH⁺) 502.

Example 34

3-[7-Fluoro-2-(4-fluoro-benzyl)-3-oxo-2,3-dihydro-1H-isoindol-1-yl]-N-(5-sulfamoyl-pyridin-2-yl)-propionamide

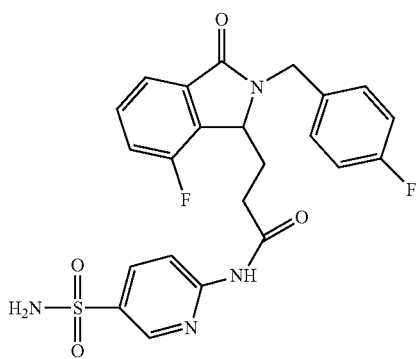 [SMILES: NS(=O)(=O)c1ccc(NC(=O)CCC2c3c(F)cccc3C(=O)N2Cc2ccc(F)cc2)nc1]

A. 6-Aminopyridine-3-sulfonic acid amide

6-Chloropyridine-3-sulfonic acid amide (200 mg, 1 mmol) was placed in a sealed tube with 2 mL 28% aq. NH₄OH and heated to 110° C. for 4 h. The mixture was diluted with brine and the title compound was collected as a solid (120 mg, 67%).

B. 3-[7-Fluoro-2-(4-fluoro-benzyl)-3-oxo-2,3-dihydro-1H-isoindol-1-yl]-N-(5-sulfamoyl-pyridin-2-yl)-propionamide The product from Part A (110 mg, 0.636 mmol) and the product from Example 11, Part D (211 mg, 0.64 mmol) were converted to the title compound in a manner analogous to the method described in Example 7, Part E, using 1:1 $CH_2Cl_2$/$CH_3CN$ in place of THF, and without crystallization (30 mg, 10%). ¹H NMR (300 MHz, CDCl₃) δ 8.47 (d, J=2 Hz, 1H), 7.99 (dd, J=9 Hz, 2 Hz, 1H), 7.57 (d, J=8 Hz, 1H), 7.42 (m, 1H), 7.21 (m, 4H), 6.97 (t, J=9 Hz, 2H), 6.50 (d, J=9 Hz, 1H), 5.33 (br s, 2H), 5.210 (d, J=15 Hz, 1H), 4.63 (m, 1H), 4.05 (d, J=15 Hz, 1H), 2.49 (m, 1H), 2.35 (m, 1H), 1.84 (m, 2H). MS: m/z (MH⁺) 487.

Example 35

3-[4-chloro-2-(4-fluoro-benzyl)-3-oxo-2,3-dihydro-1H-isoindol-1-yl]-N-pyridin-2-yl-propionamide

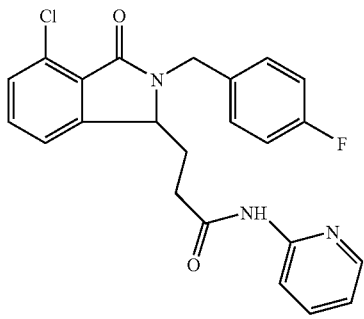 [SMILES: O=C(CCC1c2cccc(Cl)c2C(=O)N1Cc1ccc(F)cc1)Nc1ccccn1]

A. 4-Chloro-2-(4-fluoro-benzyl)-isoindole-1,3-dione

A mixture of 4-chloro-isoindole-1,3-dione (2.75 g, 15 mmol) and 4-fluorobenzylamine (1.88 g, 15 mmol) in glacial acetic acid (10 mL) was heated at 150° C. in microwave for 30 mins. After cooled to room temperature, the reaction mixture was poured into ice water and the white precipitates were collected. Recrystallization with EtOH provided the title compound (3.86 g, 89%).

B. Methanesulfonic acid 2-[4-chloro-2-(4-fluoro-benzyl)-3-oxo-2,3-dihydro-1H-isoindol-1-yl]-ethyl ester and Methanesulfonic acid 2-[7-chloro-2-(4-fluoro-benzyl)-3-oxo-2,3-dihydro-1H-isoindol-1-yl]-ethyl ester The product from Part A was converted to the title compounds as a mixture of regioisomers in a manner analogous to the method described in Example 9, part B-E.

C. 3-[4-Chloro-2-(4-fluoro-benzyl)-3-oxo-2,3-dihydro-1H-isoindol-1-yl]-propionitrile A mixture of the mesylate prepared in Part B (0.33 g, 0.83 mmol) and sodium cyanide (0.20 g, 4.15 mmol) in DMF (2 mL) with 2 drop of 15-crown-6 ether was heated at 70° C. in microwave for 30 mins, cooled to room temperature and water/ethyl acetate were added. The organic extracts were washed with brine, dried over Na₂SO₄ and concentrated to give a crude oil. Purification by chromatography (hexane/ethyl acetate) afforded the title compound (120 mg) and a mixture of two regio-isomers (77 mg) with a total of 56% yield.

D. 3-[4-Chloro-2-(4-fluoro-benzyl)-3-oxo-2,3-dihydro-1H-isoindol-1-yl]-propionic acid The product from Part C (120 mg) was suspended in 6N HCl (1 mL) and heated at 180° C. in microwave for 30 mins, cooled to room temperature and extracted with ethyl acetate. The organics were washed with brine, dried over Na₂SO₄, concentrated and triturated with diethyl ether to provided the title compound (80 mg) 63%.

E. 3-[4-Chloro-2-(4-fluoro-benzyl)-3-oxo-2,3-dihydro-1H-isoindol-1-yl]-N-pyridin-2-yl-propionamide The product from Part D (60 mg, 0.17 mmol) was converted to the title compound by the method described in Example 27, using $CH_2Cl_2$ in place of THF, and purified by chromatography (EtOAc/hexane) to afford the title compound (60 mg, 82%). ¹H NMR (300 MHz, d-DMSO) δ 10.26 (s, 1H), 8.26-8.24 (m, 1H), 7.97 (d, J=8.6 Hz, 1H), 7.75-7.70 (m, 1H), 7.60-7.56 (m, 2H), 7.48-7.47 (m, 1H), 7.39-7.35 (m, 2H), 7.17-7.12 (m, 2H), 7.06-7.03 (m, 1H), 5.02 (d, J=15 Hz, 1H), 4.58-4.55 (m, 1H), 4.35 (d, J=15 Hz, 1H), 2.37-2.32 (m, 2H), 2.09-2.01 (m, 1H), 1.84-1.07 (m, 1H). MS: m/z (MH⁺) 424.

Example 36

3-[7-Chloro-2-(4-fluoro-benzyl)-3-oxo-2,3-dihydro-1H-isoindol-1-yl]-N-pyridin-2-yl-propionamide

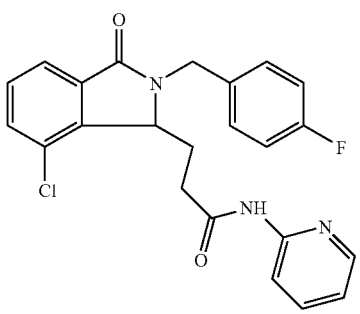 [SMILES: O=C(CCC1c2c(Cl)cccc2C(=O)N1Cc1ccc(F)cc1)Nc1ccccn1]

A. 3-[4-Chloro-2-(4-fluoro-benzyl)-3-oxo-2,3-dihydro-1H-isoindol-1-yl]-propionitrile and 3-[7-chloro-2-(4-fluoro-benzyl)-3-oxo-2,3-dihydro-1H-isoindol-1-yl]-propionitrile A mixture of the mesylate prepared in Example 35, Part B (0.40 g, 1.0 mmol) and potassium cyanide (0.33 g, 5.0 mmol) in EtOH (2 mL)/H$_2$O (0.5 mL) was heated at 100° C. in microwave for 15 mins, cooled to room temperature and evaporated in vacuo. The crude mixture was partitioned between water and ethyl acetate. The organic extracts were washed with brine, dried over Na$_2$SO$_4$ and concentrated to give a crude oil. Purification by chromatography (hexane/ethyl acetate) afforded two regio-isomers, 3-[4-Chloro-2-(4-fluoro-benzyl)-3-oxo-2,3-dihydro-1H-isoindol-1-yl]-propionitrile (130 mg) and 3-[7-chloro-2-(4-fluoro-benzyl)-3-oxo-2,3-dihydro-1H-isoindol-1-yl]-propionitrile (70 mg), with a total yield of 61%.

B. 3-[7-Chloro-2-(4-fluoro-benzyl)-3-oxo-2,3-dihydro-1H-isoindol-1-yl]-propionic acid The product from Part A (70 mg, 0.21 mmol) was converted to the title compound in a manner analogous to the method described in Example 35, Part D without chromatography (70 mg, 95%).

C. 3-[7-Chloro-2-(4-fluoro-benzyl)-3-oxo-2,3-dihydro-1H-isoindol-1-yl]-N-pyridin-2-yl-propionamide The product from Part B (50 mg, 0.14 mmol) was converted to the title compound in a manner analogous to the method described in Example 27, using CH$_2$Cl$_2$ in place of THF, and purified by chromatography (EtOAc/hexane) to afford the title compound (27 mg, 44%). $^1$H NMR (300 MHz, d-DMSO) δ 10.23 (s, 1H), 8.25-8.23 (m, 1H), 7.93 (d, J=8.4 Hz, 1H), 7.73-7.65 (m, 3H), 7.53 (t, J=7.79 Hz, 1H), 7.40-7.36 (m, 2H), 7.17-7.12 (m, 2H), 7.05-7.02 (m, 1H), 5.05 (d, J=15.6 Hz, 1H), 4.71-4.69 (m, 1H), 4.39 (d, J=15.6 Hz, 1H), 2.67-2.60 (m, 1H), 2.33-2.47 (m, 1H), 1.99-1.92 (m, 1H), 1.72-1.64 (m, 1H). MS: m/z (MH$^+$) 424.

Example 37

N-(5-Acetyl-pyridin-2-yl)-3-[7-fluoro-2-(4-fluoro-benzyl)-3-oxo-2,3-dihydro-1H-isoindol-1-yl]-propionamide

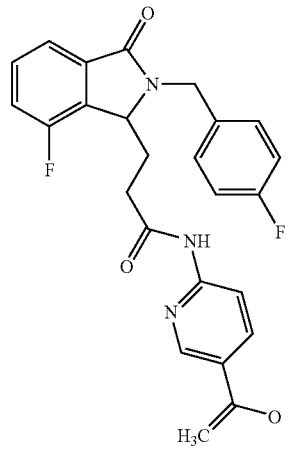 [SMILES: C=C(O)c1ccc(NC(=O)CCC2c3c(F)cccc3C(=O)N2Cc2ccc(F)cc2)nc1]

A. 1-(6-Aminopyridin-3-yl)-ethanone 1-(6-Chloropyridin-3-yl)-ethanone (230 mg, 1.5 mmol), 1 mL 28% aq NH$_4$OH, and catalytic CuSO$_4$.5H$_2$O were heated to 130° C. in a sealed tube for 5 h. The mixture was cooled, diluted with 20 mL water, and washed with 2×25 mL EtOAc. The combined organics were washed with brine, dried (MgSO$_4$), filtered, and evaporated. The title compound was obtained by silica gel chromatography (163 mg, 80%).

B. N-(5-Acetylpyridin-2-yl)-3-[7-fluoro-2-(4-fluorobenzyl)-3-oxo-2,3-dihydro-1H-isoindol-1-yl]-propionamide The product from Part A (70 mg, 0.5 mmol) and from Example 11, Part D (172 mg, 0.5 mmol) were converted to the title compound in a manner analogous to the method described in Example 27 (96 mg, 21%). $^1$H NMR (300 MHz, CDCl$_3$) δ 8.76 (s, 1H), 8.21 (m, 2H), 8.0 (m, 1H), 7.68 (d, J=7 Hz, 1H), 7.46 (m, 1H), 7.31 (m, 2H), 7.19 (t, J=8 Hz, 1H), 7.01 (t, J=9, 2H), 5.25 (d, J=15, 1H), 4.71 (m, 1H), 4.25 (d, J=15 Hz, 1H), 2.58 (s, 3H), 2.52 (m, 2H), 1.98 (m, 2H). MS: m/z (MH$^+$) 450.

Example 38

N-(5-Bromo-pyridin-2-yl)-3-[4-chloro-2-(4-fluoro-benzyl)-3-oxo-2,3-dihydro-1H-isoindol-1-yl]-propionamide

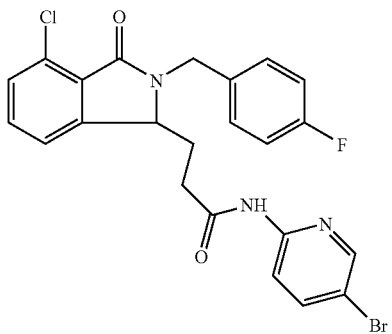 [SMILES: O=C(CCC1c2cccc(Cl)c2C(=O)N1Cc1ccc(F)cc1)Nc1ccc(Br)cn1]

The product from Example 35, Part D (65 mg, 0.19 mmol) was converted to the title compound in a manner analogous to the method described in Example 27 using CH$_2$Cl$_2$ in place of THF, and purified by chromatography (EtOAc/hexane) to afford the title compound (7 mg, 7%). $^1$H NMR (300 MHz, CDCl$_3$) δ 8.25 (d, J=2.18, 1H), 8.02 (d, J=8.67, 1H), 7.82-7.74 (m, 2H), 7.53-7.42 (m, 3H), 7.33-7.26 (m, 2H), 7.06-7.01 (m, 2H), 5.28 (d, J=15 Hz, 1H), 4.65-4.63 (m, 1H), 4.22 (d, J=15 Hz, 1H), 2.89-2.81 (m, 1H), 2.57-2.50 (m, 1H), 1.85-1.72 (m, 2H). MS: m/z (MH$^+$) 502.

Example 39

3-[4,7-Dichloro-2-(4-fluoro-benzyl)-3-oxo-2,3-dihydro-1H-isoindol-1-yl]-N-pyridin-2-yl-propionamide

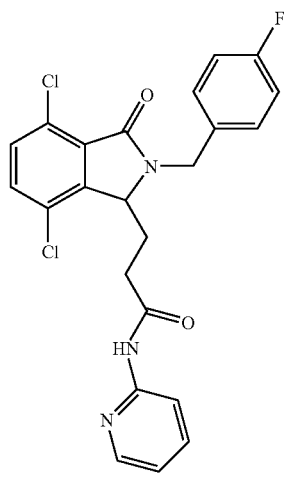 [SMILES: O=C(CCC1c2c(Cl)ccc(Cl)c2C(=O)N1Cc1ccc(F)cc1)Nc1ccccn1]

The title compound was prepared from 4,7-dichloro-isoindole-1,3-dione and 4-fluorobenzylamine using a analogous to the procedure described in Example 35, Part A-E. $^1$HNMR (300 MHz, CDCl$_3$) δ 8.20 (d, J=4.4 Hz, 1H); 8.07 (d, J=8.3 Hz, 1H); 7.70-7.65 (m, 2H); 7.39-7.313 (m, 4H); 7.06-7.00 (m, 3H); 5.30 (d, J=14.9 Hz, 1H); 4.59 (t, J=3.5 Hz, 1H); 4.21 (d, J=15 Hz, 1H); 2.92-2.81 (m, 1H); 2.59-2.48 (m, 1H); 1.96-1.86 (m, 1H); 1.79-1.67 (m, 1H). MS: m/z (MH$^+$) 458.

Example 40

3-[7-Fluoro-2-(4-fluoro-benzyl)-3-oxo-2,3-dihydro-1H-isoindol-1-yl]-N-(1-oxy-pyridin-2-yl)-propionamide

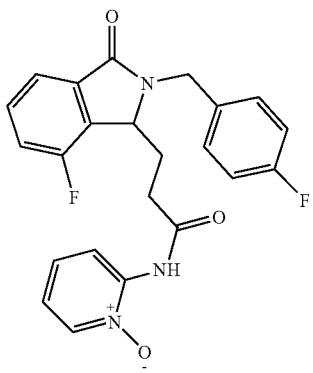

The title compound was prepared from the carboxylic acid prepared in Part D of Example 11 and 1-oxy-pyridin-2-ylamine using a procedure analogous to the procedure described in Example 27. $^1$HNMR (400 MHz, CDCl$_3$) δ 9.77 (s, 1H), 8.36 (d, J=7.2 Hz, 1H); 8.21 (d, J=6.58 Hz, 1H); 7.72 (d, J=7.7 Hz, 1H), (tt, J=7.8 Hz, 1H), 7.33-7.21 (m, 4H); (m, 3H); 5.26 (d, J=15.0 Hz, 1H); 4.70 (m, 1H); (d, J=15.1 Hz, 1H); 2.56-2.51 (m, 2H); 2.10-2.03 (m, 2H). MS: m/z (MH$^+$) 424

Example 41

3-[7-Fluoro-2-(4-fluoro-benzyl)-3-oxo-2,3-dihydro-1H-isoindol-1-yl]-N-(5-methyl-pyridin-2-yl)-propionamide

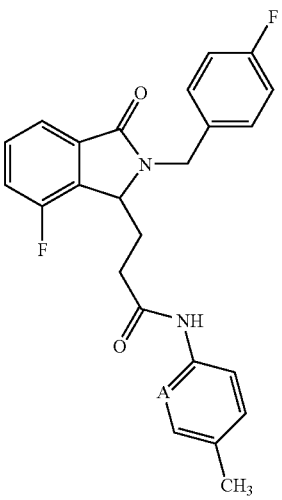

The product from Example 11, Part D (120 mg, 0.36 mmol) and 5-methylpyridin-2-ylamine (39 mg, 0.36 mmol) were converted to the title compound in a manner analogous to the method described in Example 27 (78 mg, 50%). $^1$H NMR (400 MHz, CDCl$_3$) δ 8.27 (s, 1H), 7.99 (d, J=8 Hz, 1H), 7.94 (s, 1H), 7.66 (d, J=7 Hz, 1H), 7.49 (dd, J=8 Hz, 2 Hz, 1H), 7.43 (m, 1H), 7.30 (m, 2H), 7.17 (t, J=9 Hz, 1H), 7.00 (t, J=7 Hz, 2H), 5.26 (d, J=15 Hz, 1H), 4.68 (m, 1H), 4.21 (d, J=15 Hz, 1H), 2.55 (m, 2H), 2.27 (s, 3H), 1.92 (m, 2H). MS: m/z (MH$^+$) 422.

Example 42

3-[7-Fluoro-3-oxo-2-(4-pyrol-1-yl-benzyl)-2,3-dihydro-1H-isoindol-1-yl]-N-(5-fluoro-pyridin-2-yl)-propionamide

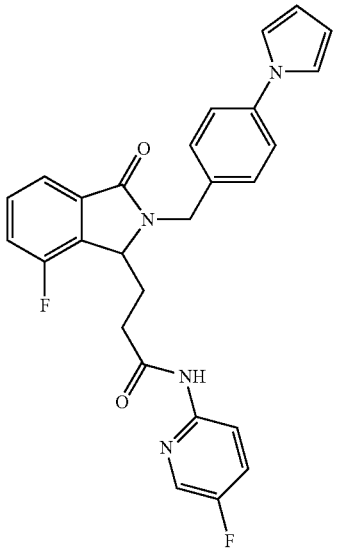 [SMILES: O=C(CCC1c2c(F)cccc2C(=O)N1Cc1ccc(-n2cccc2)cc1)Nc1ccc(F)cn1]

A. 3-[7-Fluoro-2-(4-nitrobenzyl)-3-oxo-2,3-dihydro-1H-isoindol-1-yl]-propionitrile The title compound was obtained from 4-fluorophthalic anhydride and 4-nitrobenzyl amine as described in Example 9, Parts A through F.

B. 3-[2-(4-Aminobenzyl)-7-fluoro-3-oxo-2,3-dihydro-1H-isoindol-1-yl]-propionitrile The product from Part A (510 mg, 1.7 mmol) was dissolved in 40 mL EtOAc and reduced to the title compound by catalytic hydrogenation with Pd. The compound was used without further purification (510 mg, quant).

C. 3-[7-Fluoro-3-oxo-2-(4-pyrol-1-yl-benzyl)-2,3-dihydro-1H-isoindol-1-yl]-propionitrile The product from Part B (300 mg, 0.97 mmol) and 2,5-dimethoxytetrahydrofuran (0.13 mL, 0.97 mmol) were heated to reflux in 3 mL toluene and 3 mL glacial acetic acid for 2.5 h. The mixture was cooled to room temperature, diluted with water and washed with EtOAc. The organic phase was washed with water, aq. NaHCO$_3$, and brine, then dried (MgSO$_4$), filtered and evaporated. The compound was used without further purification (260 mg, 75%).

D. 3-[7-Fluoro-3-oxo-2-(4-pyrol-1-yl-benzyl)-2,3-dihydro-1H-isoindol-1-yl]-propionic acid The product from Part C (260 mg, 0.72 mmol) was converted to the title compound in a manner analogous to the method described in Example 9, Part G (150 mg, 55%).

E. 3-[7-Fluoro-3-oxo-2-(4-pyrol-1-yl-benzyl)-2,3-dihydro-1H-isoindol-1-yl]-N-(5-fluoropyridin-2-yl)-propionamide The product from Part D (75 mg, 0.2 mmol) and 5-fluoropyridin-2-ylamine (22 mg, 0.2 mmol) were converted to the title compound in a manner analogous to the method described in Example 27 (14 mg, 15%). $^1$H NMR (400 MHz, CDCl$_3$) δ 8.08 (m, 1H), 8.01 (d, J=3 Hz, 1H), 7.71 (d, J=8 Hz, 1H), 7.56 (s, 1H), 7.48 (m, 1H), 7.40 (m, 3H), 7.36 (m, 2H), 7.22 (t, J=9 Hz, 1H), 7.03 (m, 2H), 6.32 (m, 2H), 5.25 (d, J=15 Hz, 1H), 4.76 (m, 1H), 4.35 (d, J=15 Hz, 1H), 2.59 (m, 2H), 1.93 (m, 2H). MS: m/z (MH$^+$) 473.

Example 43

N-(6-Chloro-pyridazin-3-yl)-3-[7-fluoro-2-(4-fluoro-benzyl)-3-oxo-2,3-dihydro-1H-isoindol-1-yl]-Propionamide

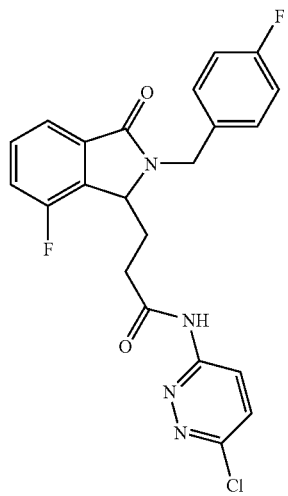 [SMILES: O=C(CCC1c2c(F)cccc2C(=O)N1Cc1ccc(F)cc1)Nc1ccc(Cl)nn1]

The product of Example 11, Part D (150 mg, 0.453 mmol) and 3-amino-6-chloropyridazine (57.3 mg, 0.453 mmol) were converted to the title compound in a manner analogous to the method described in Example 27 (112 mg, 18%). $^1$H NMR (400 MHz, CDCl$_3$) δ 9.71 (s, 1H), 8.45 (d, J=9 Hz, 1H), 7.61 (d, J=8 Hz, 1H); 7.49 (d, J=9 Hz, 1H); 7.39 (m, 1H); 7.30 (m, 2H), 7.17 (t, J=9 Hz, 1H); 7.01 (t, J=8.5 Hz, 2H); 5.29 (d, J=15 Hz, 1H), 4.69 (m, 1H), 4.25 (d, J=15 Hz, 1H), 2.63-2.52 (m, 2H); 2.29-2.17 (m, 2H). MS: m/z (MH$^+$) 443.

Example 44

N-(5-Chloro-pyridin-2-yl)-3-[7-fluoro-2-(4-fluoro-benzyl)-3-oxo-2,3-dihydro-1H-isoindol-1-yl]-propionamide

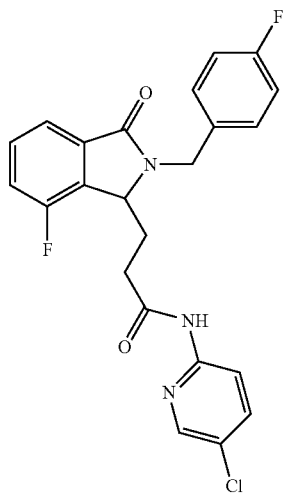 [SMILES: O=C(CCC1c2c(F)cccc2C(=O)N1Cc1ccc(F)cc1)Nc1ccc(Cl)cn1]

The product of Example 11, Part D (120 mg, 0.45 mmol) and 2-amino-5-chloropyridine (58 mg, 0.45 mmol) were converted to the title compound in a manner analogous to the method described in Example 27 (85 mg, 49%). $^1$H NMR (400 MHz, CDCl$_3$) δ 8.12 (s, 1H), 8.09 (d, J=8.7 Hz, 1H), 7.81 (s, 1H); 7.69-7.61 (m, 3H); 7.48-7.43 (m, 1H); 7.35 (m, 2H), 7.26 (t, J=8.8 Hz, 1H); 7.17 (t, J=8.5 Hz, 2H); 5.28 (d, J=15 Hz, 1H), 4.69 (s, 1H), 4.26 (d, J=15 Hz, 1H), 2.59-2.48 (m, 2H); 1.98-1.90 (m, 2H). MS: m/z (MH$^+$) 443.

Example 45

3-(6-{3-[7-Fluoro-2-(4-fluoro-benzyl)-3-oxo-2,3-dihydro-1H-isoindol-1-yl]-propionylamino}-pyridin-3-yl)-acrylic acid ethyl ester

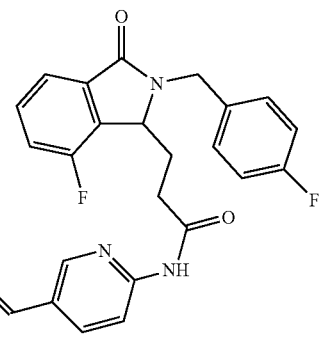

The product of Example 11, Part D (137 mg, 0.41 mmol) and 3-(6-amino-pyridin-3-yl)-acrylic acid ethyl ester (80 mg, 0.41 mmol) were converted to the title compound in a manner analogous to the method described in Example 27 (90.8 mg, 43%). $^1$H NMR (400 MHz, CDCl$_3$) δ 8.3 (s, 1H), 8.18 (d, J=8.7 Hz, 1H), 8.03 (s, 1H); 7.89-7.86 (d, J=8.6 Hz, 1H); 7.71 (d, J=7 Hz, 1H); 7.62 (d, J=16 Hz, 1H), 7.49-7.44 (m, 1H); 7.34 (m, 2H); 7.23 (t, J=8.75 Hz, 1H); 7.04 (t, J=8.8 Hz, 2H); 6.44 (d, J=16 Hz, 1H); 5.28 (d, J=15 Hz, 1H), 4.70 (m, 1H), 4.29-4.23 (m, 3H); 2.57-2.50 (m, 2H); 2.04-1.93 (m, 2H); 1.36 (t, J=7.4 Hz, 3H) MS: m/z (MH$^+$) 506.

Example 46

6-{3-[7-Fluoro-2-(4-fluoro-benzyl)-3-oxo-2,3-dihydro-1H-isoindol-1-yl]-propionylamino}-nicotinic acid benzyl ester

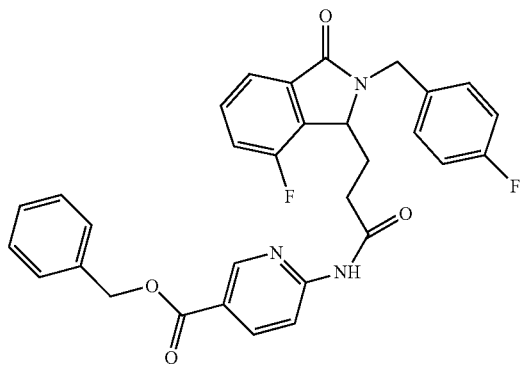 [SMILES: O=C(CCC1c2c(F)cccc2C(=O)N1Cc1ccc(F)cc1)Nc1ccc(C(=O)OCc2ccccc2)cn1]

A. 6-Amino-nicotinic acid benzyl ester

Benzyl bromide (0.86 ml, 7.9 mmol) was added to a mixture of 6-aminonicotinic acid (1.0 g, 7.2 mmol) and potassium carbonate (1.5 g, 10.8 mmol) in DMF (4 mL). The mixture was stirred at room temperature for 16 hr and diluted with water (50 mL). The aqueous mixture was extracted with ethyl acetate (1×). The EtOAc layer was washed with brine, dried over MgSO$_4$ and concentrated to provide crude solid product. Recrystallization from diethyl ether provided the title compound as a pale yellow solid (0.88 g, 53%).

B. 6-{3-[7-Fluoro-2-(4-fluoro-benzyl)-3-oxo-2,3-dihydro-1H-isoindol-1-yl]-propionylamino}-nicotinic acid benzyl ester The product of Example 11, Part D (94 mg, 0.28 mmol) and the benzyl ester of Part A (65 mg, 0.28 mmol) were converted to the title compound in a manner analogous to the method described in Example 27 (81 mg, 53%). $^1$H NMR (400 MHz, CDCl$_3$) δ 8.87 (broad s, 1H); 8.32 (d, J=8.6 Hz, 1H), 8.17 (d, J=8.6 Hz, 1H), 7.79 (broad s, 1H), 7.70 (d, J=7.4 Hz, 1H); 7.48-7.29 (m, 9H); 7.23 (t, J=8.8 Hz, 1H), 7.04 (t, J=8.5 Hz, 2H); 5.27 (d, J=15 Hz, 1H), 4.72 (m, 1H), 4.27 (d, J=15 Hz, 1H), 2.61-2.45 (m, 2H), 2.04-1.92 (m, 2H). MS: m/z (MH$^+$) 542.

Example 47

N-(5-Cyano-pyridin-2-yl)-3-[7-fluoro-2-(4-fluoro-benzyl)-3-oxo-2,3-dihydro-1H-isoindol-1-yl]-propionamide

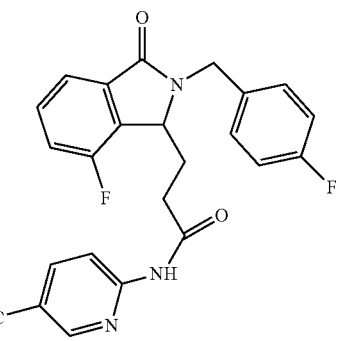

The product of Example 11, Part D (113 mg, 0.34 mmol) and 2-amino-5-cyanopyridine (41 mg, 0.34 mmol) were converted to the title compound in a manner analogous to the method described in Example 27 (61 mg, 41%). $^1$H NMR (400 MHz, CDCl$_3$) δ 8.48 (broad s, 1H); 8.24 (d, J=8.6 Hz, 1H), 7.92 (d, J=8.7 Hz, 1H), 7.82 (broad s, 1H), 7.70 (d, J=7.6 Hz, 1H); 7.49-7.45 (m, 1H), 7.33 (m, 2H), 7.23 (t, J=8.6 Hz, 1H); 7.04 (t, J=8.5 Hz, 2H); 5.24 (d, J=15 Hz, 1H), 4.72 (m, 1H), 4.28 (d, J=15 Hz, 1H), 2.61-2.56 (m, 1H); 2.53-2.46 (m, 1H); 2.00-1.95 (m, 2H). MS: m/z (MH+) 433.

Example 48

3-[7-Fluoro-2-(4-fluoro-benzyl)-3-oxo-2,3-dihydro-1H-isoindol-1-yl]-N-(5-methanesulfonyl-pyridin-2-yl)-propionamide

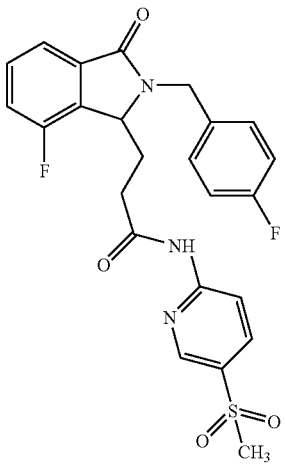 [SMILES: CS(=O)(=O)c1ccc(NC(=O)CCC2c3c(F)cccc3C(=O)N2Cc2ccc(F)cc2)nc1]

The product of Example 11, Part D (0.175 g, 0.529 mmol) and 5-Methanesulfonyl-pyridin-2-ylamine (91 mg, 0.529 mmol) were converted to the title compound in a manner analogous to the method described in Example 27 (159 mg, 62%). ¹H NMR (400 MHz, CDCl₃) d 8.74 (s, 1H); 8.30 (d, J=8.8 Hz, 1H), 8.18 (d, J=8.8 Hz, 1H), 8.09 (broad s, 1H), 7.69 (d, J=7 Hz, 1H); 7.49-7.44 (m, 1H); 7.33-7.30 (m, 2H), 7.23 (t, J=8.8 Hz, 1H); 7.04 (t, J=8.6 Hz, 2H); 5.25 (d, J=15 Hz, 1H), 4.73 (m, 1H), 4.28 (d, J=15 Hz, 1H), 3.18 (s, 3H); 2.61-2.59 (m, 1H); 2.53-2.50 (m, 1H); 2.04-1.97 (m, 2H). MS: m/z (MH+) 486.

Example 49

6-{3-[2-(4-Dimethylamino-benzyl)-7-fluoro-3-oxo-2,3-dihydro-1H-isoindol-1-yl]-propionylamino}-nicotinic acid

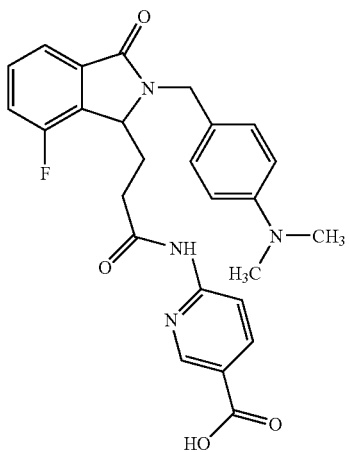 [SMILES: CN(C)c1ccc(CN2C(=O)c3cccc(F)c3C2CCC(=O)Nc2ccc(C(=O)O)cn2)cc1]

A. 3-[2-(4-Dimethylaminobenzyl)-7-fluoro-3-oxo-2,3-dihydro-1H-isoindol-1-yl]-propionitrile A cold (0° C.) mixture of 3M sulfuric acid solution (7 mL) and a 37% formaldehyde solution (8.3 mL) in THF (40 mL) was stirred vigorously. A slurry of the compound prepared in Part B of Example 42 (1.9 g, 6.15 mmol) and NaBH4 (5 g) in THF (40 mL) was then added portionwise (when half of the sodium borohydride solution was added an additional 7 mL of 3M H₂SO₄ was added). The reaction was allowed to warm to room temperature over a 4 hr period with continued stirring. Water (50 mL) was added and the THF was removed under reduced pressure. A 50% KOH solution was added to basic pH and the mixture extracted with EtOAc (3 x). The combined EtOAc extracts were washed with brine, dried over MgSO₄, filtered and evaporated in vacuo to provide crude product. Chromatography (EtOAc/hexane) provided the title compound (1.85 g, 89%).

B. 3-[2-(4-Dimethylamino-benzyl)-7-fluoro-3-oxo-2,3-dihydro-1H-isoindol-1-yl]-propionic acid A 6.6 N NaOH solution (10 mL) was slowly added to a mixture of the compound prepared in Part A (1.85 g, 5.49 mmol) in MeOH (50 mL). The resulting mixture was stirred at 65-70° C. for 16 hr, cooled to room temperature, concentrated, diluted with water, acidified with 1 N HCl, and extracted with dichloromethane (3×). The combined CH₂Cl₂ extracts were washed with brine, dried over MgSO₄, filtered and evaporated in vacuo to provide the title compound (0.68 g).

C. 6-{3-[2-(4-Dimethylamino-benzyl)-7fluoro-3-oxo-2,3-dihydro-1H-isoindol-1-yl]-propionylamino}-nicotinic acid benzyl ester The product of Part B (0.66 g, 1.85 mmol) and the benzyl ester prepared in Part A of Example 46 (0.42 g, 1.85 mmol) were converted to the title compound (0.517 g, 49%) in a manner analogous to the method described in Example 27.

D. 6-{3-[2-(4-Dimethylamino-benzyl)-7-fluoro-3-oxo-2,3-dihydro-1H-isoindol-1-yl]-propionylamino}-nicotinic acid The product of Part C (0.52 g, 0.919 mmol) in EtOAc/MeOH (25 mL/25 mL) containing one drop of acetic acid was hydrogenation in an H-cube apparatus with a 10% Pd/C cartridge to provide the title compound as a pale yellow solid (358 mg, 82%). ¹H NMR (400 MHz, CD₃OD) δ 8.80 (broad s, 1H); 8.25 (d, J=8.8 Hz, 1H), 8.07 (m, 1H), 7.64 (d, J=7.7 Hz, 1H); 7.54-7.51 (m, 2H), 7.32 (t, J=8.8 Hz, 1H); 7.22 (d, J=8.3 Hz, 2H); 6.72 (d, J=8.2 Hz, 2H); 5.02 (d, J=15 Hz, 1H), 4.81 (m, 1H), 4.43 (d, J=15 Hz, 1H), 2.83 (s, 6H); 2.53 (m, 2H); 2.03-1.99 (m, 1H); 1.94-1.88 (m, 1H). MS: m/z (MH+) 477.

Examples 50-51

The enantiomers of the compound prepared in Example 26 were separated by chiral chromatography using a chiral pak AD 25 cm column and a 70/30 CH₃CN/EtOH mobile phase at 220 nm to provide the following title compounds.

(R)-6-{3-[7-Fluoro-2-(4-fluoro-benzyl)-3-oxo-2,3-dihydro-1H-isoindol-1-yl]-propionylamino}-nicotinic acid methyl ester

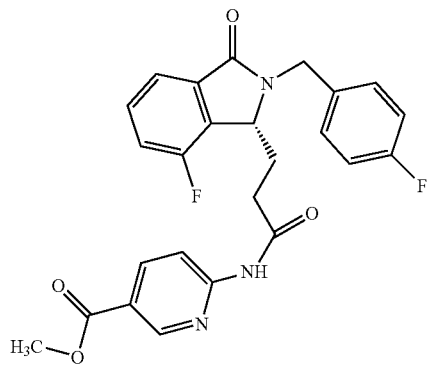

¹H NMR (400 MHz, CDCl₃) δ 8.84 (d, J=2 Hz, 1H), 8.29 (dd, J=8 Hz, 2 Hz, 1H), 8.18 (d, J=9 Hz, 1H), 7.88 (br s, 1H), 7.71 (d, J=7 Hz, 1H), 7.49 (m, 1H), 7.34 (m, 2H), 7.23 (t, J=9 Hz, 1H), 7.04 (t, J=9 Hz, 2H), 5.27 (d, J=15 Hz, 1H), 4.71 (m, 1H), 4.27 (d, J=15 Hz, 1H), 3.92 (s, 3H), 2.60-2.54 (m, 1H); 2.53-2.47 (m, 1H); 2.09-1.91 (m, 2H). MS: m/z (MH⁺) 466.

(S)-6-{3-[7-Fluoro-2-(4-fluoro-benzyl)-3-oxo-2,3-dihydro-1H-isoindol-1-yl]-propionylamino}-nicotinic acid methyl ester

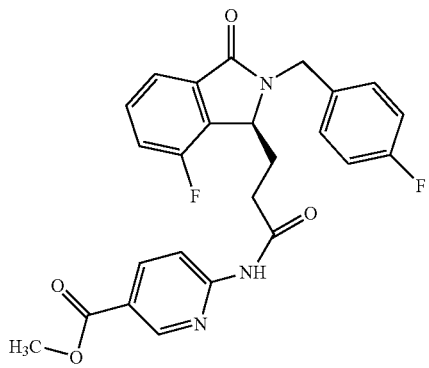 [SMILES: COC(=O)c1ccc(NC(=O)CC[C@H]2c3c(F)cccc3C(=O)N2Cc2ccc(F)cc2)nc1]

$^1$H NMR (400 MHz, CDCl$_3$) δ 8.84 (d, J=2 Hz, 1H), 8.467 (broad s, 1H); 8.35 (dd, J=8 Hz, 2 Hz, 1H), 8.25 (d, J=9 Hz, 1H), 7.71 (d, J=7 Hz, 1H), 7.49 (m, 1H), 7.34 (m, 2H), 7.24 (t, J=9 Hz, 1H), 7.04 (t, J=9 Hz, 2H), 5.27 (d, J=15 Hz, 1H), 4.71 (m, 1H), 4.29 (d, J=15 Hz, 1H), 3.94 (s, 3H), 2.60-2.49 (m, 2H); 2.09-1.92 (m, 2H). MS: m/z (MH$^+$) 466.

D) General Administration, Formulation, and Dosages

The present compounds are glucokinase modulators and are therefore useful in treating, preventing, or inhibiting the progression of glucokinase mediated conditions, such as metabolic disorders including diabetes, diabetes, obesity, and associated symptoms or complications thereof. In particular, a glucokinase mediated condition can be selected, for example, from diabetes such as IDDM and NIDDM, obesity, IGT (Impaired Glucose Tolerance), IFG (Impaired Fasting Glucose), Syndrome X (or Metabolic Syndrome), and insulin resistance.

The invention features a method for treating a subject with a glucokinase mediated disease, said method comprising administering to the subject a therapeutically effective amount of a pharmaceutical composition comprising a compound of the invention. The invention also provides a method for treating or inhibiting the progression of diabetes, obesity, and associated symptoms or complications thereof in a subject, wherein the method comprises administering to the subject a therapeutically effective amount of a pharmaceutical composition comprising a compound of the invention.

Pharmaceutically acceptable salts include the therapeutically active non-toxic salts of disclosed compounds. The latter can conveniently be obtained by treating the base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, palmoic and the like acids. The term "salt" also comprises the solvates which the disclosed compounds, as well as the salts thereof, are able to form. Such solvates are for example hydrates, alcoholates and the like. Conversely the salt form can be converted by treatment with alkali into the free base form.

Stereoisomeric forms define all the possible isomeric forms which the compounds of the invention may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the (R)- or (S)-configuration; substituents on bivalent cyclic saturated radicals may have either the cis- or trans-configuration. The invention encompasses stereochemically isomeric forms including diastereoisomers, as well as mixtures thereof in any proportion of the disclosed compounds. The disclosed compounds may also exist in their tautomeric forms. Such forms although not explicitly indicated in the above and following formulae are intended to be included within the scope of the present invention.

E) Use

The compounds of the present invention are pharmaceutically active, for example, as glucokinase modulators. Examples of glucokinase-mediated diseases include diabetes (such as IDDM, NIDDM, IGT, IFG), obesity and Syndrome X (or Metabolic Syndrome), and conditions associated with such diseases such as hyperglycemia, elevated blood glucose level, and insulin resistance.

According to one aspect of the invention, the disclosed compounds and compositions are useful for the amelioration of symptoms associated with, the treatment of, and the prevention of, the following conditions and diseases: diabetes such as IDDM and NIDDM, obesity, IGT (Impaired Glucose Tolerance), IFG (Impaired Fasting Glucose), Syndrome X (or Metabolic Syndrome), hyperglycemia, elevated blood glucose level, and insulin resistance.

According to one aspect of the invention, the disclosed compounds may be used in a method for treating or inhibiting the progression of a glucokinase-mediated condition and, optionally, an additional glucokinase mediated condition, said method comprising administering to a patient in need of treatment a pharmaceutically effective amount of a composition of the invention.

The invention also features pharmaceutical compositions which include, without limitation, one or more of the disclosed compounds, and pharmaceutically acceptable carriers or excipients.

1. Dosages

Those of skill in the treatment of disorders or conditions mediated by glucokinase could easily determine the effective daily amount from the test results presented hereinafter and other information. The exact dosage and frequency of administration depends on the particular compound of invention used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines in practicing the present invention.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg/kg to about 300 mg/kg (preferably from about 0.01 mg/kg to about 100 mg/kg; and, more preferably, from about 0.01 mg/kg to about 30 mg/kg) and may be given at a dosage of from about 0.01 mg/kg/day to about 300 mg/kg/day (preferably from about 0.01 mg/kg/day to about 100 mg/kg/day, more preferably from about 0.01 mg/kg/day to about 30 mg/kg/day and even more preferably from about 0.01 mg/kg/day to about 10 mg/kg/day). Preferably, the method for the treatment of metabolic disorders described in the present invention using any of the compounds as defined herein, the dosage form will contain a pharmaceutically acceptable carrier containing between from about 0.01 mg to about 100 mg; and, more preferably, from about 5 mg to about 50 mg of the compound, and may be constituted into any form suitable for the mode of administration selected. The dosages, however, may be varied depending upon the requirement of the subjects, the severity of the condition being treated and the compound being employed. The use of either daily administration or postperiodic dosing may be employed.

Preferably these compositions are in unit dosage forms from such as tablets, pills, capsules, dry powders for reconstitution or inhalation, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, dry powder inhaler or other inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid pharmaceutical compositions such as tablets, the principal active ingredient is mixed with a pharmaceutical carrier, e.g. conventional tableting ingredients such as diluents, binders, adhesives, disintegrants, lubricants, antiadherents and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), crosslinked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL™ silica available from Cabot, SYLOID™ silica available from W.R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active form of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate, cellulose acetate trimellitate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agent include pharmaceutical grade lecithins. Suitable flocculating agent include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

Compounds of this invention may be administered in any of the foregoing compositions and dosage regimens or by means of those compositions and dosage regimens established in the art whenever treatment of glucokinase mediated disorders is required for a subject in need thereof.

The daily dose of a pharmaceutical composition of the present invention may be varied over a wide range from about 0.7 mg to about 500 mg per adult human per day; preferably, the dose will be in the range of from about 0.7 mg to about 100 mg per adult human per day; most preferably the dose will be in the range of from about 0.7 mg to about 50 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. An effective amount of the drug is ordinarily supplied at a dosage level of from about 0.01 mg/kg to about 300 mg/kg of body weight per day. Advantageously, a compound of the present invention may be administered in a single daily dose or the total daily dosage may be administered in divided doses of two, three or four times daily.

Optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

2. Formulations

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

The compounds of the present invention may be formulated into various pharmaceutical forms for administration purposes. Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

3. Combination Therapy

The compounds of the present invention may be used in combination with one or more pharmaceutically active agents. These agents include other glucokinase modulators, anti-diabetic agents, other lipid lowering agents, direct thrombin inhibitor (DTI), as well as blood pressure lowering agents such as statin drugs and the fibrates.

Other glucokinase modulators include:

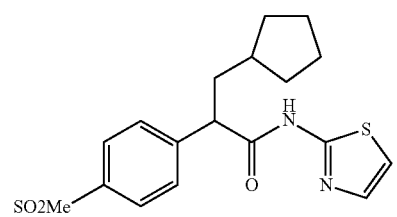

Ro-28-1675

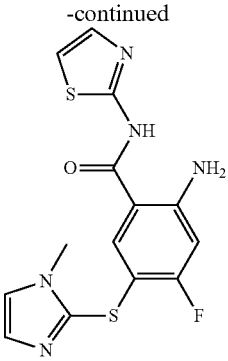

Banyu/Merck glucokinase activator

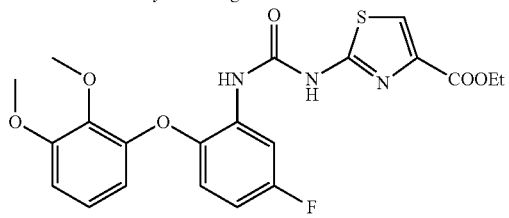

Novo Nordisk IV

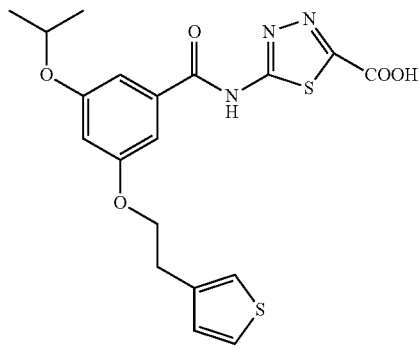

Astra Zeneca glucokinase activator

Anti-diabetic agents include RXR modulators such as:
(1) bexarotene (4-(1-(3,5,5,8,8-pentamethyl-5,6,7,8-tetrahydro-2-naphthalenyl)ethenyl)benzoic acid, known as TARGRETIN, TARGRETYN, TARGREXIN; also known as LGD 1069, LG 100069, LG 1069, LDG 1069, LG 69, RO 264455);
(2) 9-cis-retinoic acid;
(3) AGN-4326 (also known as ALRT-4204, AGN-4204, ALRT-326, ALRT-324, or LGD 1324);
(4) LGD 1324 (ALRT 324);
(5) LG 100754;
(6) LY-510929;
(7) LGD 1268 (6-(1,1,4,4,6-pentamethyl-1,2,3,4-tetrahydro-naphth-7-ylcycloprop-1-yl)nicotinic acid, known as ALRT 268 or LG 100268);
(8) LG 100264; and
(9) substituted heterocycles as disclosed in PCT publications WO 01/16122 and WO 01/16123 by Maxia.

One preferred example of substituted heterocycles is MX-6054, which is 2,4-thiazolidinedione, 5-[[3-(5,6,7,8-tetrahydro-3,5,5,8,8-pentamethyl-2-naphthalenyl)-4-(trifluoromethoxy)phenyl]methylene]-, (5Z)—, also named 3-(3,5, 5,8,8-pentamethyl-5,6,7,8-tetrahydro-2-naphthyl)-4-trifluoromethoxybenzylidene-2,4-thiazolidinedione, represented by the following formula:

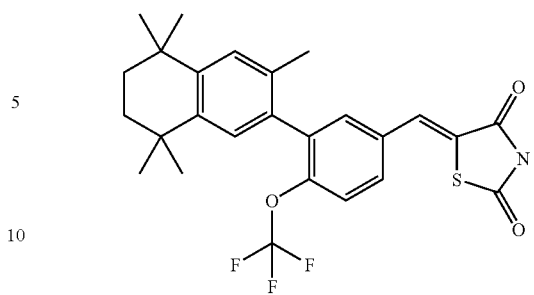

Another preferred example of substituted heterocycles is 2,4-thiazolidinedione, 5-[[3-(1-ethyl-1,2,3,4-tetrahydro-4,4, 6-trimethyl-2-oxo-7-quinolinyl)-4-(trifluoromethoxy)phenyl]methylene]-, (5Z)—, represented by the following formula:

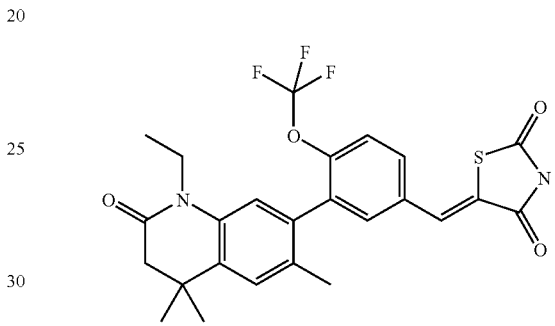

Preferred substituted heterocycles are selected from:
3-(3,5,5,8,8-pentamethyl-5,6,7,8-tetrahydro-2-naphthyl)-4-trifluoromethoxybenzylidene-2,4-thiazolidinedione;
4-[2-(3,5,5,8,8-pentamethyl-5,6,7,8-tetrahydro-2-naphthyl)-1,3-dioxolane]benzylidene-2,4-thiazolidinedione;
4-[2-(5,5,8,8-tetramethyl-5,6,7,8-tetrahydro-2-naphthyl)-2-propyl]benzylidene-2,4-thiazolidinedione;
4-[2-(3,5,5,8,8-pentamethyl-5,6,7,8-tetrahydro-2-naphthyl)-1,3-dioxolane]benzylidene-2-thioxo-2,4-thiazolidinedione;
4-[2-(5,5,8,8-tetramethyl-5,6,7,8-tetrahydro-2-naphthyl)-2-propyl]benzylidene-2-thioxo-2,4-thiazolidinedione;
4-[2-(3,5,5,8,8-pentamethyl-5,6,7,8-tetrahydro-2-naphthyl)-1,3-dioxolane]benzylidene-2-thioxo-2,4-imidazolidinedione;
4-[2-(5,5,8,8-tetramethyl-5,6,7,8-tetrahydro-2-naphthyl)-2-propyl]benzylidene-2-thioxo-2,4-imidazolidinedione;
4-[2-(3,5,5,8,8-pentamethyl-5,6,7,8-tetrahydro-2-naphthyl)-1,3-dioxolane]benzylidene-2,4-imidazolidinedione;
4-[2-(5,5,8,8-tetramethyl-5,6,7,8-tetrahydro-2-naphthyl)-2-propyl]benzylidene-2,4-imidazolidinedione;
4-[2-(3,5,5,8,8-pentamethyl-5,6,7,8-tetrahydro-2-naphthyl)-1,3-dioxolane]benzyl-2,4-thiazolidinedione;
4-[2-(5,5,8,8-tetramethyl-5,6,7,8-tetrahydro-2-naphthyl)-2-propyl]benzyl-2,4-thiazolidinedione;
4-[2-(3,5,5,8,8-pentamethyl-5,6,7,8-tetrahydro-2-naphthyl)-1,3-dioxolane]benzyl-2-thioxo-2,4-thiazolidinedione;
4-[2-(5,5,8,8-tetramethyl-5,6,7,8-tetrahydro-2-naphthyl)-2-propyl]benzyl-2-thioxo-2,4-thiazolidinedione;
4-[2-(3,5,5,8,8-pentamethyl-5,6,7,8-tetrahydro-2-naphthyl)-1,3-dioxolane]benzyl-2-thioxo-2,4-imidazolidinedione;
4-[2-(5,5,8,8-tetramethyl-5,6,7,8-tetrahydro-2-naphthyl)-2-propyl]benzyl-2-thioxo-2,4-imidazolidinedione;

4-[2-(3,5,5,8,8-pentamethyl-5,6,7,8-tetrahydro-2-naphthyl)-1,3-dioxolane]benzyl-2,4-imidazolidinedione; and 4-[2-(5,5,8,8-tetramethyl-5,6,7,8-tetrahydro-2-naphthyl)-2-propyl]benzyl-2,4-imidazolidinedione.

Anti-diabetic agents also include thiazolidinedione and non-thiazolidinedione insulin sensitizers, which decrease peripheral insulin resistance by enhancing the effects of insulin at target organs and tissues.

The following agents are known to bind and activate the nuclear receptor peroxisome proliferator-activated receptor-gamma (PPARγ) which increases transcription of specific insulin-responsive genes. Examples of PPAR-gamma agonists are thiazolidinediones such as:
(1) rosiglitazone (2,4-thiazolidinedione, 5-((4-(2-(methyl-2-pyridinylamino)ethoxy)phenyl)methyl)-, (Z)-2-butenedioate (1:1) or 5-((4-(2-(methyl-2-pyridinylamino)ethoxy)phenyl)methyl)-2,4-thiazolidinedione, known as AVANDIA; also known as BRL 49653, BRL 49653C, BRL 49653c, SB 210232, or rosiglitazone maleate);
(2) pioglitazone (2,4-thiazolidinedione, 5-((4-(2-(5-ethyl-2-pyridinyl)ethoxy)phenyl)methyl)-, monohydrochloride, (+−)- or 5-((4-(2-(5-ethyl-2-pyridyl)ethoxy)phenyl)methyl)-2,4-thiazolidinedione, known as ACTOS, ZACTOS, or GLUSTIN; also known as AD 4833, U 72107, U 72107A, U 72107E, pioglitazone hydrochloride (USAN));
(3) troglitazone(5-((4-((3,4-dihydro-6-hydroxy-2,5,7,8-tetramethyl-2H-1-benzopyran-2-yl)methoxy)phenyl) methyl)-2,4-thiazolidinedione, known as NOSCAL, REZULIN, ROMOZIN, or PRELAY; also known as CI 991, CS 045, GR 92132, GR 92132X);
(4) isaglitazone((+)-5-[[6-[(2-fluorophenyl)methoxy]-2-naphthalenyl]methyl]-2,4-thiazolidinedione or 5-((6-((2-fluorophenyl)methoxy)-2-naphthalenyl)methyl-2, 4-thiazolidinedione or 5-(6-(2-fluorobenzyloxy) naphthalen-2-ylmethyl)thiazolidine-2,4-dione, also known as MCC-555 or neoglitazone); and
(5) 5-BTZD.

Additionally, the non-thiazolidinediones that act as insulin sensitizing agents include, but are not limited to:
(1) JT-501 (JTT 501, PNU-1827, PNU-716-MET-0096, or PNU 182716: isoxazolidine-3,5-dione, 4-((4-(2-phenyl-5-methyl)-1,3-oxazolyl)ethylphenyl-4) methyl-);
(2) KRP-297 (5-(2,4-dioxothiazolidin-5-ylmethyl)-2-methoxy-N-(4-(trifluoromethyl)benzyl)benzamide or 5-((2,4-dioxo-5-thiazolidinyl)methyl)-2-methoxy-N-((4-(trifluoromethyl)phenyl)methyl)benzamide); and
(3) Farglitazar (L-tyrosine, N-(2-benzoylphenyl)-O-(2-(5-methyl-2-phenyl-4-oxazolyl)ethyl)- or N-(2-benzoylphenyl)-O-(2-(5-methyl-2-phenyl-4-oxazolyl) ethyl)-L-tyrosine, or GW2570 or GI-262570).

Other anti-diabetic agents have also been shown to have PPAR modulator activity such as PPAR gamma, SPPAR gamma, and/or PPAR delta/gammaR agonist activity. Examples are listed below:
(1) AD 5075;
(2) R 119702 ((+−)-5-(4-(5-Methoxy-1H-benzimidazol-2-ylmethoxy)benzyl)thiazolin-2,4-dione hydrochloride, or CI 1037 or CS 011);
(3) CLX-0940 (peroxisome proliferator-activated receptor alpha agonist/peroxisome proliferator-activated receptor gamma agonist);
(4) LR-90 (2,5,5-tris(4-chlorophenyl)-1,3-dioxane-2-carboxylic acid, PPAARR delta/γ agonist);
(5) Tularik (PPAR γ agonist);
(6) CLX-0921 (PPAR γ agonist);
(7) CGP-52608 (PPAR agonist);
(8) GW-409890 (PPAR agonist);
(9) GW-7845 (PPAR agonist);
(10) L-764406 (PPAR agonist);
(11) LG-101280 (PPAR agonist);
(12) LM-4156 (PPAR agonist);
(13) Risarestat (CT-112);
(14) YM 440 (PPAR agonist);
(15) AR-H049020 (PPAR agonist);
(16) GW 0072 (4-(4-((2S,5S)-5-(2-(bis(phenylmethyl) amino)-2-oxoethyl)-2-heptyl-4-oxo-3-thiazolidinyl) butyl)benzoic acid);
(17) GW 409544 (GW-544 or GW-409544);
(18) NN 2344 (DRF 2593);
(19) NN 622 (DRF 2725);
(20) AR-H039242 (AZ-242);
(21) GW 9820 (fibrate);
(22) GW 1929 (N-(2-benzoylphenyl)-O-(2-(methyl-2-pyridinylamino)ethyl)-L-tyrosine, known as GW 2331, PPAR alpha/γ agonist);
(23) SB 219994 ((S)-4-(2-(2-benzoxazolylmethylamino) ethoxy)-alpha-(2,2,2-trifluoroethoxy)benzenepropanoic acid or 3-(4-(2-(N-(2-benzoxazolyl)-N-methylamino)ethoxy)phenyl)-2(S)-(2,2,2-trifluoroethoxy) propionic acid or benzenepropanoic acid, 4-(2-(2-benzoxazolylmethylamino)ethoxy)-alpha-(2,2,2-trifluoroethoxy)-, (alphaS)-, PPAR alpha/γ agonist);
(24) L-796449 (PPAR alpha/γ agonist);
(25) Fenofibrate (Propanoic acid, 2-[4-(4-chlorobenzoyl) phenoxy]-2-methyl-, 1-methylethyl ester, known as TRICOR, LIPCOR, LIPANTIL, LIPIDIL MICRO PPAR alpha agonist);
(26) GW-9578 (PPAR alpha agonist);
(27) GW-2433 (PPAR alpha/γ agonist);
(28) GW-0207 (PPAR γ agonist);
(29) LG-100641 (PPAR/γ agonist);
(30) LY-300512 (PPAR γ agonist);
(31) NID525-209 (NID-525);
(32) VDO-52 (VDO-52);
(33) LG 100754 (peroxisome proliferator-activated receptor agonist);
(34) LY-510929 (peroxisome proliferator-activated receptor agonist);
(35) bexarotene (4-(1-(3,5,5,8,8-pentamethyl-5,6,7,8-tetrahydro-2-naphthalenyl)ethenyl)benzoic acid, known as TARGRETIN, TARGRETYN, TARGREXIN; also known as LGD 1069, LG 100069, LG 1069, LDG 1069, LG 69, RO 264455); and
(36) GW-1536 (PPAR alpha/γ agonist).

Other insulin sensitizing agents include, but are not limited to:
(1) INS-1 (D-chiro inositol or D-1,2,3,4,5,6-hexahydroxycyclohexane);
(2) protein tyrosine phosphatase 1 B (PTP-1B) inhibitors;
(3) glycogen synthase kinase-3 (GSK3) inhibitors;
(4) beta 3 adrenoceptor agonists such as ZD 2079 ((R)—N-(2-(4-(carboxymethyl)phenoxy)ethyl)-N-(2-hydroxy-2-phenethyl)ammonium chloride, also known as ICI D 2079) or AZ 40140;
(5) glycogen phosphorylase inhibitors;
(6) fructose-1,6-bisphosphatase inhibitors;
(7) chromic picolinate, vanadyl sulfate (vanadium oxysulfate);
(8) KP 102 (organo-vanadium compound);
(9) chromic polynicotinate;
(10) potassium channel agonist NN 414;

(11) YM 268 (5,5'-methylene-bis(1,4-phenylene)bismethylenebis(thiazolidine-2,4-dione);
(12) TS 971;
(13) T 174 ((+−)-5-(2,4-dioxothiazolidin-5-ylmethyl)-2-(2-naphthylmethyl)benzoxazole);
(14) SDZ PGU 693 ((+)-trans-2(S-((4-chlorophenoxy)methyl)-7alpha-(3,4-dichlorophenyl)tetrahydropyrrolo(2,1-b)oxazol-5(6H)-one);
(15) S 15261 ((−)-4-(2-((9H-fluoren-9-ylacetyl)amino)ethyl)benzoic acid 2-((2-methoxy-2-(3-(trifluoromethyl)phenyl)ethyl)amino)ethyl ester);
(16) AZM 134 (Alizyme);
(17) ARIAD;
(18) R 102380;
(19) PNU 140975 (1-(hydrazinoiminomethyl)hydrazino) acetic acid;
(20) PNU 106817 (2-(hydrazinoiminomethyl)hydrazino) acetic acid;
(21) NC 2100 (5-((7-(phenylmethoxy)-3-quinolinyl)methyl)-2,4-thiazolidinedione;
(22) MXC 3255;
(23) MBX 102;
(24) ALT 4037;
(25) AM 454;
(26) JTP 20993 (2-(4-(2-(5-methyl-2-phenyl-4-oxazolyl)ethoxy)benzyl)-malonic acid dimethyl diester);
(27) Dexlipotam (5(R)-(1,2-dithiolan-3-yl)pentanoic acid, also known as (R)-alpha lipoic acid or (R)-thioctic acid);
(28) BM 170744 (2,2-Dichloro-12-(p-chlorophenyl)dodecanoic acid);
(29) BM 152054 (5-(4-(2-(5-methyl-2-(2-thienyl)oxazol-4-yl)ethoxy)benzothien-7-ylmethyl)thiazolidine-2,4-dione);
(30) BM 131258 (5-(4-(2-(5-methyl-2-phenyloxazol-4-yl)ethoxy)benzothien-7-ylmethyl)thiazolidine-2,4-dione);
(31) CRE 16336 (EML 16336);
(32) HQL 975 (3-(4-(2-(5-methyl-2-phenyloxazol-4-yl)ethoxy)phenyl)-2(S)-(propylamino)propionic acid);
(33) DRF 2189 (5-((4-(2-(1-Indolyl)ethoxy)phenyl)methyl)thiazolidine-2,4-dione);
(34) DRF 554158;
(35) DRF-NPCC;
(36) CLX 0100, CLX 0101, CLX 0900, or CLX 0901;
(37) IkappaB Kinase (IKK B) Inhibitors
(38) mitogen-activated protein kinase (MAPK) inhibitors p38 MAPK Stimulators
(39) phosphatidyl-inositide triphosphate
(40) insulin recycling receptor inhibitors
(41) glucose transporter 4 modulators
(42) TNF-α antagonists
(43) plasma cell differentiation antigen-1 (PC-1) Antagonists
(44) adipocyte lipid-binding protein (ALBP/aP2) inhibitors
(45) phosphoglycans
(46) Galparan;
(47) Receptron;
(48) islet cell maturation factor;
(49) insulin potentiating factor (IPF or insulin potentiating factor-1);
(50) somatomedin C coupled with binding protein (also known as IGF-BP3, IGF-BP3, SomatoKine);
(51) Diab II (known as V-411) or Glucanin, produced by Biotech Holdings Ltd. or Volque Pharmaceutical;
(52) glucose-6 phosphatase inhibitors;
(53) fatty acid glucose transport protein;
(54) glucocorticoid receptor antagonists; and
(55) glutamine:fructose-6-phosphate amidotransferase (GFAT) modulators.

Anti-diabetic agents can further include biguanides, which decreases liver glucose production and increases the uptake of glucose. Examples of biguanides include metformin such as:

(1) 1,1-dimethylbiguanide (e.g., Metformin—DepoMed, Metformin—Biovail Corporation, or METFORMIN GR (metformin gastric retention polymer)); and
(2) metformin hydrochloride (N,N-dimethylimidodicarbonimidic diamide monohydrochloride, also known as LA 6023, BMS 207150, GLUCOPHAGE, or GLUCOPHAGE XR.

Additionally, anti-diabetic agents include alpha-glucosidase inhibitors, which inhibit alpha-glucosidase. Alpha-glucosidase converts fructose to glucose, thereby delaying the digestion of carbohydrates. The undigested carbohydrates are subsequently broken down in the gut, reducing the postprandial glucose peak.

Examples of alpha-glucosidase inhibitors include, but are not limited to:

(1) acarbose (D-glucose, O-4,6-dideoxy-4-(((1S-(1alpha,4alpha,5beta,6alpha))-4,5,6-trihydroxy-3-(hydroxymethyl)-2-cyclohexen-1-yl)amino)-alpha-D-glucopyranosyl-(1-4)-O-alpha-D-glucopyranosyl-(1-4)-, also known as AG-5421, Bay-g-542, BAY-g-542, GLUCOBAY, PRECOSE, GLUCOR, PRANDASE, GLUMIDA, or ASCAROSE);
(2) Miglitol (3,4,5-piperidinetriol, 1-(2-hydroxyethyl)-2-(hydroxymethyl) (2R(2alpha,3beta,4alpha,5beta))- or (2R,3R,4R,5S)-1-(2-hydroxyethyl)-2-(hydroxymethyl-3,4,5-piperidinetriol, also known as BAY 1099, BAY M 1099, BAY-m-1099, BAYGLITOL, DIASTABOL, GLYSET, MIGLIBAY, MITOLBAY, PLUMAROL);
(3) CKD-711 (0-4-deoxy-4-((2,3-epoxy-3-hydroxymethyl-4,5,6-trihydroxycyclohexane-1-yl)amino)-alpha-b-glucopyranosyl-(1-4)-alpha-D-glucopyranosyl-(1-4)-D-glucopyranose);
(4) emiglitate (4-(2-((2R,3R,4R,5S)-3,4,5-trihydroxy-2-(hydroxymethyl)-1-piperidinyl)ethoxy)benzoic acid ethyl ester, also known as BAY o 1248 or MKC 542);
(5) MOR 14 (3,4,5-piperidinetriol, 2-(hydroxymethyl)-1-methyl-, (2R-(2alpha,3beta,4alpha,5beta))-, also known as N-methyldeoxynojirimycin or N-methylmoranoline); and
(6) Voglibose (3,4-dideoxy-4-((2-hydroxy-1-(hydroxymethyl)ethyl)amino)-2-C-(hydroxymethyl)-D-epi-inositol or D-epi-Inositol, 3,4-dideoxy-4-((2-hydroxy-1-(hydroxymethyl)ethyl)amino)-2-C-(hydroxymethyl)-, also known as A 71100, AO 128, BASEN, GLUSTAT, VOGLISTAT.

Anti-diabetic agents also include insulins such as regular or short-acting, intermediate-acting, and long-acting insulins, non-injectable or inhaled insulin, tissue selective insulin, glucophosphokinin (D-chiroinositol), insulin analogues such as insulin molecules with minor differences in the natural amino acid sequence and small molecule mimics of insulin (insulin mimetics), and endosome modulators. Examples include, but are not limited to:

(1) Biota;
(2) LP 100;
(3) (SP-5-21)-oxobis(1-pyrrolidinecarbodithioato-S,S') vanadium,
(4) insulin aspart (human insulin (28B-L-aspartic acid) or B28-Asp-insulin, also known as insulin X14, INA-X14, NOVORAPID, NOVOMIX, or NOVOLOG);

(5) insulin detemir (Human 29B-(N-6-(1-oxotetradecyl)-L-lysine)-(1A-21A), (1B-29B)-Insulin or NN 304);
(6) insulin lispro ("28B-L-lysine-29B-L-proline human insulin, or Lys(B28), Pro(B29) human insulin analog, also known as lys-pro insulin, LY 275585, HUMALOG, HUMALOG MIX 75/25, or HUMALOG MIX 50/50);
(7) insulin glargine (human (A21-glycine, B31-arginine, B32-arginine) insulin HOE 901, also known as LANTUS, OPTISULIN);
(8) Insulin Zinc Suspension, extended (Ultralente), also known as HUMULIN U or ULTRALENTE;
(9) Insulin Zinc suspension (Lente), a 70% crystalline and 30% amorphous insulin suspension, also known as LENTE ILETIN II, HUMULIN L, or NOVOLIN L;
(10) HUMULIN 50/50 (50% isophane insulin and 50% insulin injection);
(11) HUMULIN 70/30 (70% isophane insulin NPH and 30% insulin injection), also known as NOVOLIN 70/30, NOVOLIN 70/30 PenFill, NOVOLIN 70/30 Prefilled;
(12) insulin isophane suspension such as NPH ILETIN II, NOVOLIN N, NOVOLIN N PenFill, NOVOLIN N Prefilled, HUMULIN N;
(13) regular insulin injection such as ILETIN II Regular, NOVOLIN R, VELOSULIN BR, NOVOLIN R PenFill, NOVOLIN R Prefilled, HUMULIN R, or Regular U-500 (Concentrated);
(14) ARIAD;
(15) LY 197535;
(16) L-783281; and
(17) TE-17411.

Anti-diabetic agents can also include insulin secretion modulators such as:
(1) glucagon-like peptide-1 (GLP-1) and its mimetics;
(2) glucose-insulinotropic peptide (GIP) and its mimetics;
(3) exendin and its mimetics;
(4) dipeptyl protease (DPP or DPPIV) inhibitors such as
  (4a) DPP-728 or LAF 237 (2-pyrrolidinecarbonitrile, 1-(((2-((5-cyano-2-pyridinyl)amino)ethyl)amino)acetyl), known as NVP-DPP-728, DPP-728A, LAF-237);
  (4b) P 3298 or P32/98 (di-(3N-((2S,3S)-2-amino-3-methyl-pentanoyl)-1,3-thiazolidine)fumarate);
  (4c) TSL 225 (tryptophyl-1,2,3,4-tetrahydroisoquinoline-3-carboxylic acid);
  (4d) Valine pyrrolidide (valpyr);
  (4e) 1-aminoalkylisoquinolinone-4-carboxylates and analogues thereof;
  (4f) SDZ 272-070 (1-(L-Valyl)pyrrolidine);
  (4g) TMC-2A, TMC-2B, or TMC-2C;
  (4h) Dipeptide nitriles (2-cyanopyrrolodides);
  (4i) CD26 inhibitors; and
  (4j) SDZ 274-444;
(5) glucagon antagonists such as AY-279955; and
(6) amylin agonists which include, but are not limited to, pramlintide (AC-137, Symlin, tripro-amylin or pramlintide acetate).

Well-known anti-diabetic agents include insulin, sulfonylureas, biguanides, meglitinides, AGI's (Alpha-Glucosidase Inhibitors; e.g., Glyset), PPAR alpha agonists, and PPAR gamma agonists, and dual PPAR alpha/gamma agonists.

Examples of lipid lowering agents include bile acid sequestrants, fibric acid derivatives, nicotinic acid, and HMGCoA reductase inhibitors. Specific examples include statins such as LIPITOR®, ZOCOR®, PRAVACHOL®, LESCOL®, and MEVACOR®, and pitavastatin (nisvastatin) (Nissan, Kowa Kogyo, Sankyo, Novartis) and extended release forms thereof, such as ADX-159 (extended release lovastatin), as well as Colestid, Locholest, Questran, Atromid, Lopid, and Tricor.

Examples of blood pressure lowering agents include antihypertensive agents, such as angiotensin-converting enzyme (ACE) inhibitors (Accupril, Altace, Captopril, Lotensin, Mavik, Monopril, Prinivil, Univasc, Vasotec, and Zestril), adrenergic blockers (such as Cardura, Dibenzyline, Hylorel, Hytrin, Minipress, and Minizide) alpha/beta adrenergic blockers (such as Coreg, Normodyne, and Trandate), calcium channel blockers (such as Adalat, Calan, Cardene, Cardizem, Covera-HS, Dilacor, DynaCirc, Isoptin, Nimotop, Norvace, Plendil, Procardia, Procardia XL, Sula, Tiazac, Vascor, and Verelan), diuretics, angiotensin II receptor antagonists (such as Atacand, Avapro, Cozaar, and Diovan), beta adrenergic blockers (such as Betapace, Blocadren, Brevibloc, Cartrol, Inderal, Kerlone, Lavatol, Lopressor, Sectral, Tenormin, Toprol-XL, and Zebeta), vasodilators (such as Deponit, Dilatrate, SR, lmdur, Ismo, Isordil, Isordil Titradose, Monoket, Nitro-Bid, Nitro-Dur, Nitrolingual Spray, Nitrostat, and Sorbitrate), and combinations thereof (such as Lexxel, Lotrel, Tarka, Teczem, Lotensin HCT, Prinzide, Uniretic, Vaseretic, Zestoretic).

In addition, a second glucokinase modulator, as described above in Section B), may also be utilized as a third antidiabetic agent, provided that it is different from the first glucokinase modulator.

F) Biological Example

Glucokinase Enzyme Assay

An enzymatic Glucokinase (GK) assay using purified recombinant human liver/pancreas enzyme was used to evaluate the effects of potential small molecule modulators.

In this assay, GK catalyzes glucose phosphorylation in the presence of ATP. The product of this reaction, glucose-6-phosphate, was then oxidized by an excess of glucose-6-phosphate dehydrogenase to produce gluconate-6-phosphate with concomitant reduction of nicotinamide adenine dinucleotide (NAD). Production of reduced adenine dinucleotide (NADH) resulted in increase in fluorescence, which was used to monitor GK activity. Human GK (Liver/Pancreas) was expressed in *Escherichia coli* as a (His) 6-tagged fusion protein and was purified by metal chelate affinity chromatography. The assay was performed in a final incubation volume of 80 µl in a 96-well clear low UV absorption plates. The incubation mixture consisted of 25 mM HEPES, 2 mM MgSO$_4$, 1 mM dithiothreotol (DTT), 1 mg/mL bovine serum albumin (BSA), 1 mM ATP, 1 mM NAD, and 12 mM glucose, 10 units per mL glucose-6-phosphate dehydrogenase, and +/−300 ng per mL GK. For determination of the affinity ($K_m$) and $V_{max}$, different concentrations of glucose ranging from 0.5 mM to 40 mM were used in the assay; see Grimsby, J., Sarabu, R.; Grippo, J. F.; et. al. Science 2003, 301, 370-373. Production of reduced NAD (Nicotinamide Adenine Dinucleotide) was measured as changes in absorption at 340 nm in 96-well plate reader (Envision model #2101 Multilabel Plate reader). % Activation @ 50 µM was calculated as the percentage increase in GK activity above the vehicle control with the effective concentration of the compound being 50 µM. EC$_{50\%}$ (µM) was calculated as the effective concentration of the compound that produces 50% activation above the vehicle control, and EC$_{100}$% (µM) was calculated as the effective concentration of the compound that produces 100% activation above the vehicle control.

Compounds listed in Tables II and III below were tested in the above assay(s):

TABLE II

Liver GK data

| Compound # | % Activation @ 50 μM | EC$_{50\%}$ (μM) | EC$_{100\%}$ (μM) |
|---|---|---|---|
| 1 | 46 | 15 | — |
| 2 | 150, 112, 97 | 1.29 | 8.39 |
| 3 | 176, 188, 141 | 2.52 | 8.78 |
| 4 | 15 | — | — |
| 5 | 137.8 | 1.9 | 8 |

TABLE III

Pancreas GK data

| Compound # | % Activation @ 50 μM | EC50% (μM) | EC100% (μM) |
|---|---|---|---|
| 5 | 305.6 | 2.9 | 18 |
| 6 | 7.92 | — | — |
| 7 | 152.8 | 3.9 | 15 |
| 8 | 166.86 | 3.2 | 11 |
| 9 | 172.06 | 0.4 | 1.7 |
| 10 | 15.85 | — | — |
| 11 | 229.03 | 0.067 | 0.128 |
| 12 | 179.49 | 0.094 | 0.74 |
| 13 | 271.62 | 0.24 | 0.88 |
| 14 | 219 | 0.108 | 0.699 |
| 15 | 187.84 | 0.53 | 3.4 |
| 16 | 13.75 | — | — |
| 17 | 23.75 | — | — |
| 18 | 95 | 2 | 46 |
| 19 | 115 | 4.8 | 70 |
| 20 | 302 | 0.203 | 0.65 |
| 21 | 94.44 | 3.1 | 26.6 |
| 22 | 73.68 | 21 | 188 |
| 23 | 30.56 | — | — |
| 24 | 4.39 | — | — |
| 25 | 72.5 | — | — |
| 26 | 172.75 | 0.025 | 0.46 |
| 27 | 65 | 40 | — |
| 28 | 120 | 0.13 | 6.3 |
| 29 | 212 | 0.046 | 0.32 |
| 30 | 175 | 0.23 | 1.2 |
| 31 | 64.1 | 1.9 | 300 |
| 32 | 146.7 | 0.013 | 0.39 |
| 33 | 176.56 | 0.488 | 4.5 |
| 34 | 142.19 | 0.407 | 4.3 |
| 35 | 306.25 | 0.23 | 0.75 |
| 36 | 342.42 | 0.143 | 0.411 |
| 37 | 259.375 | 0.054 | 0.225 |
| 38 | 309.09 | 0.173 | 0.615 |
| 39 | 205.71 | 0.433 | 2.5 |
| 40 | 52.27 | — | — |
| 41 | 190.83 | 0.054 | 0.48 |
| 42 | 167.91 | 0.182 | 1.7 |
| 43 | 152 | 0.629 | 5.2 |
| 44 | 168 @ 5 μM | 0.071 | 0.375 |
| 45 | 138 @ 5 μM | 0.125 | 0.813 |
| 46 | 133 @ 5 μM | 0.219 | 1.2 |
| 47 | 113.91 | 0.42 | 15 |
| 48 | 62.82 | 17 | — |
| 49 | 212.5 | 0.06 | 0.34 |
| 50 | 38.64 | — | — |
| 51 | 223.33 | 0.0089 | 0.082 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A compound of Formula (I)

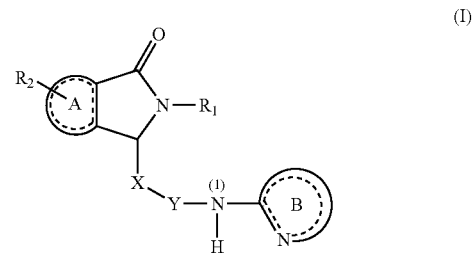

wherein $R_1$ is H or $C_{1-6}$alkyl, wherein the $C_{1-6}$ alkyl is optionally substituted with aryl, wherein said aryl is optionally substituted with $C_{1-6}$alkyl, $C_{2-6}$alkenyl, $C_{2-6}$alkynyl, halo, nitro, hydroxyl, ethynyl, —CN, aryl, —SO$_3$H, —C(O)OH, —C(O)NR'R", —SR', —OR', —C(O)R', —N(R')(R"), —S(O)$_2$—R', and —S(O)$_2$—N(R')(R"), wherein R' and R" are independently selected from H, $C_{1-6}$-alkyl, and aryl;

$R_2$ is 0-3 members independently selected from halo, —OR$_4$, —SR$_4$, —S(O)$_2$—R$_4$, carboxy, nitro, hydroxyl, amido, $C_{1-6}$alkyl, $C_{2-6}$alkenyl, $C_{2-6}$alkynyl, and amino optionally substituted with $C_{1-6}$alkyl, aryl, wherein R$_4$ is selected from H, $C_{1-6}$alkyl, and aryl;

wherein said $C_{1-6}$alkyl is optionally substituted with one to three groups selected from oxo, amino, alkoxy, carboxy, nitro, hydroxyl, and halo;

wherein said $C_{2-6}$alkenyl is optionally substituted with one to three groups selected from amino, alkoxy, carboxy, nitro, hydroxyl, and halo;

wherein said $C_{2-6}$alkynyl is optionally substituted with one to three groups selected from amino, alkoxy, carboxy, nitro, hydroxyl, and halo;

wherein said aryl is optionally substituted with $C_{1-6}$alkyl, $C_{2-6}$alkenyl, $C_{2-6}$alkynyl, halo, nitro, hydroxyl, ethynyl, —CN, aryl, —SO$_3$H, —C(O)OH, —C(O)O—$C_{1-4}$alkyl, —C(O)NR'R", —SR', —OR', —C(O)R', —N(R')(R"), —S(O)$_2$—R', and —S(O)$_2$—N(R')(R"), wherein R' and R" are independently selected from H, $C_{1-6}$-alkyl, and aryl;

A is phenyl;

B is pyridine, said pyridine being connected to N(1) through a ring carbon atom adjacent to a ring nitrogen, and said pyridine being further optionally substituted with 1 or 2 members selected from $C_{1-4}$alkyl, $C_{2-4}$alkenyl, halo, —CN, aryl, —SO$_3$H, —C(O)OH, —C(O)O—$C_{1-4}$alkyl, —OR$_4$, —SR$_4$, —C(O)R$_4$, —N(R$_4$)(R$_5$), —C(O)—N(R$_4$)(R$_5$), —S(O)$_2$—R$_4$, and —S(O)$_2$—N(R$_4$)(R$_5$), wherein R$_4$ and R$_5$ are independently selected from H, $C_{1-6}$alkyl, and aryl;

wherein said $C_{1-6}$alkyl is optionally substituted with one to three groups selected from oxo, amino, alkoxy, carboxy, nitro, hydroxyl, and halo;

wherein said $C_{2-4}$alkenyl is optionally substituted with one to three groups selected from amino, alkoxy, carboxy, nitro, hydroxyl, and halo;

wherein said aryl is optionally substituted with $C_{1-6}$alkyl, $C_{2-6}$alkenyl, $C_{2-6}$alkynyl, halo, nitro, hydroxyl, ethynyl, —CN, aryl, —SO$_3$H, —C(O)OH, —C(O)O—$C_{1-4}$alkyl, —C(O)NR'R", —SR', —OR', —C(O)R', —N(R')(R"), —S(O)$_2$—R', and —S(O)$_2$—N(R')(R"), wherein R' and R" are independently selected from H, C$_{1-6}$-alkyl, and aryl;

X is C$_{1-3}$alkylene, wherein said C$_{1-3}$alkylene is optionally substituted with one or two groups selected from halo; and Y is —C(O)—, wherein said C(O) functionality is adjacent to N(1);

or an optical isomer, enantiomer, diastereomer, racemate or pharmaceutically acceptable salt thereof.

2. The compound of claim 1 wherein
R$_1$ is C$_{1-6}$alkyl, wherein the C$_{1-6}$ alkyl is optionally substituted with C$_6$aryl or C$_{10}$aryl;
wherein said C$_6$aryl or C$_{10}$aryl is optionally substituted with C$_{1-6}$alkyl, C$_{2-6}$alkenyl, C$_{2-6}$alkynyl, halo, nitro, hydroxyl, ethynyl, —CN, aryl, —SO$_3$H, —C(O)OH, —C(O)NR'R", —SR', —OR', —C(O)R', —N(R')(R"), —S(O)$_2$—R', and —S(O)$_2$—N(R')(R"), wherein R' and R" are independently selected from H, C$_{1-6}$-alkyl, and aryl;
R$_2$ is 0-2 members independently selected from halo;
A is phenyl;
B is pyridine, said pyridine being connected to N(1) through a ring carbon atom adjacent to a ring nitrogen and said pyridine being further optionally substituted with 1 or 2 members selected from C$_{1-4}$alkyl, C$_{2-4}$alkenyl, halo, —CN, C$_6$- or C$_{10}$-aryl, —C(O)OH, —C(O)O—C$_{1-4}$alkyl, —SR$_4$, —C(O)R$_4$, —C(O)—N(R$_4$)(R$_5$), —S(O)$_2$—R$_4$, and —S(O)$_2$—N(R$_4$)(R$_6$), wherein R$_4$ and R$_5$ are independently selected from H, C$_{1-6}$alkyl, and aryl;
wherein said C$_{1-4}$alkyl is optionally substituted with one to three groups selected from oxo, amino, alkoxy, carboxy, nitro, hydroxyl, and halo;
wherein said C$_{2-4}$alkenyl is optionally substituted with one to three groups selected from amino, alkoxy, carboxy, nitro, hydroxyl, and halo;
wherein said C$_6$- or C$_{10}$-aryl aryl is optionally substituted with C$_{1-6}$alkyl, C$_{2-6}$alkenyl, C$_{2-6}$alkynyl, halo, nitro, hydroxyl, ethynyl, —CN, aryl, —SO$_3$H, —C(O)OH, —C(O)NR'R", —SR', —OR', —C(O)R', —N(R')(R"), —S(O)$_2$—R', and —S(O)$_2$—N(R')(R"), wherein R' and R" are independently selected from H, C$_{1-6}$-alkyl, and aryl;
X is C$_{1-3}$ alkylene, wherein said C$_{1-3}$alkylene is optionally substituted with one or two groups selected from halo; and
Y is —C(O)—, wherein said C(O) functionality is adjacent to B;

or an optical isomer, enantiomer, diastereomer, racemate, or pharmaceutically acceptable salt thereof.

3. The compound of claim 2 wherein R$_1$ is methyl substituted with phenyl, said phenyl being optionally substituted with halo, methoxy, or dimethoxy.

4. The compound of claim 1 wherein R$_2$ is 0-2 members independently selected from F and Cl.

5. The compound of claim 1 wherein B is

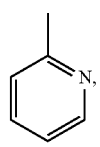

wherein said

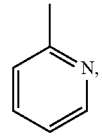

is optionally substituted with C$_{1-6}$alkyl, C$_{2-6}$alkenyl, C$_{2-6}$alkynyl, halo, nitro, hydroxyl, ethynyl, —CN, aryl, —SO$_3$H, —C(O)OH, —C(O)NR'R" —OR', —SR' —C(O)R', —N(R')(R"), —S(O)$_2$—R', and —S(O)$_2$—N(R')(R"), wherein R' and R" are independently selected from H, C$_{1-6}$-alkyl, and aryl.

6. The compound of claim 5 wherein B is substituted with 0-2 members selected from halo, C$_{1-4}$alkyl, aryl, —C(O)OH, —C(O)R$_4$, and —S(O)$_2$—N(R$_4$)(R$_5$),
wherein said C$_{1-4}$alkyl is optionally substituted with one to three groups selected from oxo, amino, alkoxy, carboxy, nitro, hydroxyl, and halo;
wherein said aryl is optionally substituted with C$_{1-6}$alkyl, C$_{2-6}$alkenyl, C$_{2-6}$alkynyl, halo, nitro, hydroxyl, ethynyl, —CN, aryl, —SO$_3$H, —C(O)OH, —C(O)NR'R", —SR', —OR', —C(O)R', —N(R')(R"), —S(O)$_2$—R', and —S(O)$_2$—N(R')(R"), wherein R' and R" are independently selected from H, C$_{1-6}$-alkyl, and aryl.

7. The compound of claim 5 wherein B is substituted with 0-2 members selected from F, Br, —CH$_3$, —CF$_3$, —CH$_2$—C(O)OH, —C(O)—CH$_3$, —CH$_2$—O—CH$_2$—O—CH$_3$, phenyl, aryl, —C(O)OH, —C(O)O—CH$_3$, —C(O)O—CH$_2$—CH$_3$, and —S(O)$_2$—NH$_2$, wherein said aryl is optionally substituted with halo.

8. The compound of claim 1 wherein X is unsubstituted C$_{1-3}$ alkylene.

9. The compound of claim 8 wherein X is methylene or ethylene.

10. The compound of claim 1 selected from
(S)-6-{3-[7-fluoro-2-(4-fluoro-benzyl)-3-oxo-2,3-dihydro-1H-isoindol-1-yl]-propionylamino}-nicotinic acid methyl ester;
(S)-6-{3-[7-fluoro-2-(4-fluoro-benzyl)-3-oxo-2,3-dihydro-1H-isoindol-1-yl]-propionylamino}-nicotinic acid;
6-{3-[2-(4-dimethylamino-benzyl)-7-fluoro-3-oxo-2,3-dihydro-1H-isoindol-1-yl]-propionylamino}-nicotinic acid;
6-{3-[4,7-difluoro-2-(4-fluoro-benzyl)-3-oxo-2,3-dihydro-1H-isoindol-1-yl]-propionylamino}-nicotinic acid;
6-{3-[4-fluoro-2-(4-fluoro-benzyl)-3-oxo-2,3-dihydro-1H-isoindol-1-yl]-propionylamino}-nicotinic acid;
3-[7-fluoro-2-(4-fluoro-benzyl)-3-oxo-2,3-dihydro-1H-isoindol-1-yl]-N-(5-fluoro-pyridin-2-yl)-propionamide;
3-[7-fluoro-2-(4-fluoro-benzyl)-3-oxo-2,3-dihydro-1H-isoindol-1-yl]-N-pyridin-2-yl-propionamide;
N-(5-acetyl-pyridin-2-yl)-3-[7-fluoro-2-(4-fluoro-benzyl)-3-oxo-2,3-dihydro-1H-isoindol-1-yl]-propionamide;
6-{3-[2-(4-methoxy-benzyl)-3-oxo-2,3-dihydro-1H-isoindol-1-yl]-propionylamino}-nicotinic acid;
6-{3-[2-(4-fluoro-benzyl)-3-oxo-2,3-dihydro-1H-isoindol-1-yl]-propionylamino}-nicotinic acid;
3-[7-fluoro-2-(4-fluoro-benzyl)-3-oxo-2,3-dihydro-1H-isoindol-1-yl]-N-(5-methoxymethoxymethyl-pyridin-2-yl)-propionamide;

3-[7-chloro-2-(4-fluoro-benzyl)-3-oxo-2,3-dihydro-1H-isoindol-1-yl]-N-pyridin-2-yl-propionamide; and
3-[7-fluoro-2-(4-fluoro-benzyl)-3-oxo-2,3-dihydro-1H-isoindol-1-yl]-N-[5-(4-fluoro-phenyl)-pyridin-2-yl]-propionamide.
11. The compound of claim 1 selected from
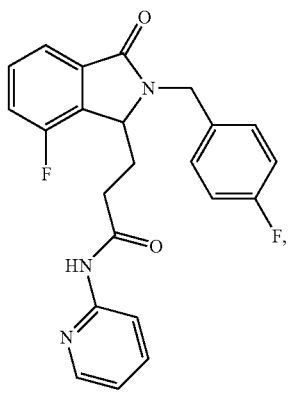
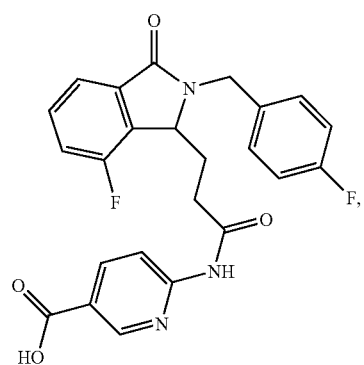
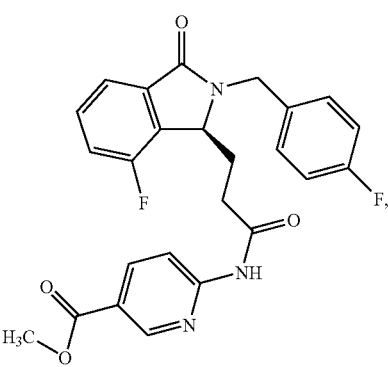
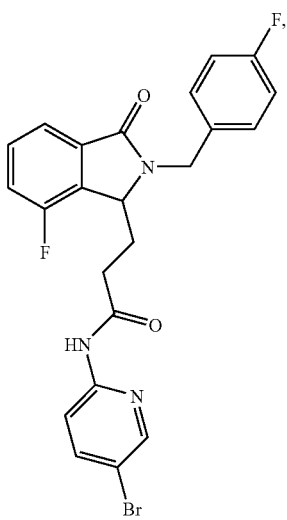
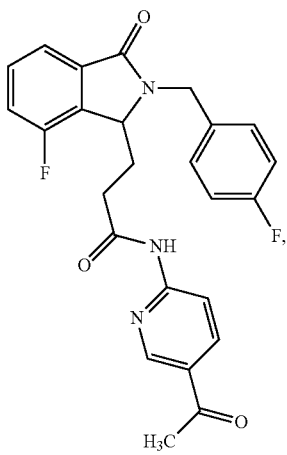
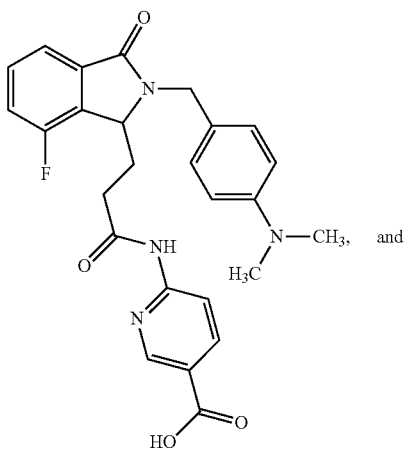

-continued

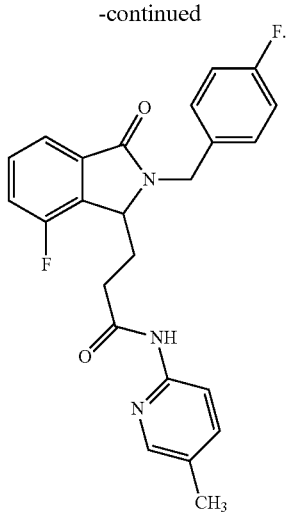

12. The compound of claim 1, wherein
R₁ is methyl substituted with phenyl, said phenyl being optionally substituted with halo, methoxy, dimethoxy, or dimethylamino;
R₂ is 0-2 members independently selected from F and Cl;
A is phenyl;
B is

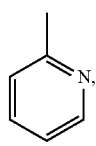

wherein said

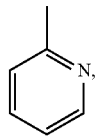

is optionally substituted with C₁₋₆alkyl, C₂₋₆alkenyl, C₂₋₆alkynyl, halo, nitro, hydroxyl, ethynyl, —CN, aryl, —SO₃H, —C(O)OH, —C(O)O—C₁₋₄alkyl, —C(O)NR'R" —OR', —SR'—C(O)R', —N(R')(R"), —S(O)₂—R', and —S(O)₂—N(R')(R"), wherein R' and R" are independently selected from H, C₁₋₆-alkyl, and aryl; and
X is methylene or ethylene.

13. The compound of claim 12 wherein B is substituted with 0-2 members selected from halo, C₁₋₄alkyl, aryl, —C(O)OH, —C(O)R₄, —C(O)O—C₁₋₄alkyl, and —S(O)₂—N(R₄)(R₅),
wherein said C₁₋₄alkyl is optionally substituted with one to three groups selected from oxo, amino, alkoxy, carboxy, nitro, hydroxyl, and halo;
wherein said aryl is optionally substituted with C₁₋₆alkyl, C₂₋₆alkenyl, C₂₋₆alkynyl, halo, nitro, hydroxyl, ethynyl, —CN, aryl, —SO₃H, —C(O)OH, —C(O)O—C₁₋₄alkyl, —C(O)NR'R", —SR', —OR', —C(O)R', —N(R')(R"), —S(O)₂—R', and —S(O)₂—N(R')(R"), wherein R' and R" are independently selected from H, C₁₋₆-alkyl, and aryl.

14. The compound of claim 13 wherein B is substituted with 0-2 members selected from F, Br, —CH₃, —CF₃, —CH₂—C(O)OH, —C(O)—CH₃, —CH₂—O—CH₂—O—CH₃, phenyl, aryl, —C(O)OH, —C(O)O—CH₃, —C(O)O—CH₂—CH₃, and —S(O)₂—NH₂, wherein said aryl is optionally substituted with halo.

15. A pharmaceutical composition comprising at least one compound of claim 1 and at least one pharmaceutically acceptable carrier.

16. The pharmaceutical composition of claim 15 comprising at least one compound selected from
(S)-6-{3-[7-fluoro-2-(4-fluoro-benzyl)-3-oxo-2,3-dihydro-1H-isoindol-1-yl]-propionylamino}-nicotinic acid methyl ester;
(S)-6-{3-[7-fluoro-2-(4-fluoro-benzyl)-3-oxo-2,3-dihydro-1H-isoindol-1-yl]-propionylamino}-nicotinic acid;
6-{3-[2-(4-dimethylamino-benzyl)-7-fluoro-3-oxo-2,3-dihydro-1H-isoindol-1-yl]-propionylamino}-nicotinic acid;
6-{3-[4,7-difluoro-2-(4-fluoro-benzyl)-3-oxo-2,3-dihydro-1H-isoindol-1-yl]-propionylamino}-nicotinic acid;
6-{3-[4-fluoro-2-(4-fluoro-benzyl)-3-oxo-2,3-dihydro-1H-isoindol-1-yl]-propionylamino}-nicotinic acid;
3-[7-fluoro-2-(4-fluoro-benzyl)-3-oxo-2,3-dihydro-1H-isoindol-1-yl]-N-(5-fluoro-pyridin-2-yl)-propionamide;
3-[7-fluoro-2-(4-fluoro-benzyl)-3-oxo-2,3-dihydro-1H-isoindol-1-yl]-N-pyridin-2-yl-propionamide;
N-(5-acetyl-pyridin-2-yl)-3-[7-fluoro-2-(4-fluoro-benzyl)-3-oxo-2,3-dihydro-1H-isoindol-1-yl]-propionamide;
6-{3-[2-(4-methoxy-benzyl)-3-oxo-2,3-dihydro-1H-isoindol-1-yl]-propionylamino}-nicotinic acid;
6-{3-[2-(4-fluoro-benzyl)-3-oxo-2,3-dihydro-1H-isoindol-1-yl]-propionylamino}-nicotinic acid;
3-[7-fluoro-2-(4-fluoro-benzyl)-3-oxo-2,3-dihydro-1H-isoindol-1-yl]-N-(5-methoxymethoxymethyl-pyridin-2-yl)-propionamide;
3-[7-chloro-2-(4-fluoro-benzyl)-3-oxo-2,3-dihydro-1H-isoindol-1-yl]-N-pyridin-2-yl-propionamide; and
3-[7-fluoro-2-(4-fluoro-benzyl)-3-oxo-2,3-dihydro-1H-isoindol-1-yl]-N-[5-(4-fluoro-phenyl)-pyridin-2-yl]-propionamide.

17. The pharmaceutical composition of claim 15 comprising at least one compound selected from

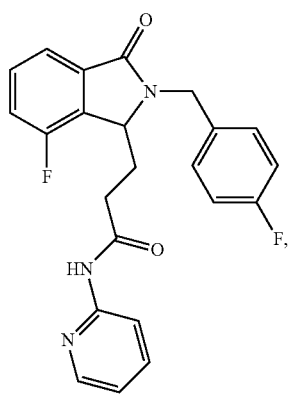

117
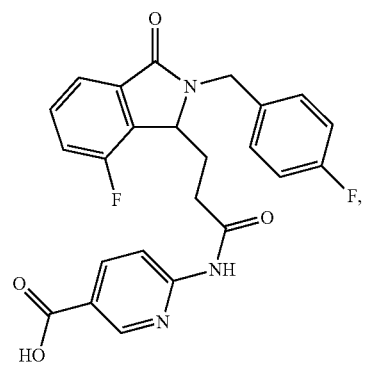
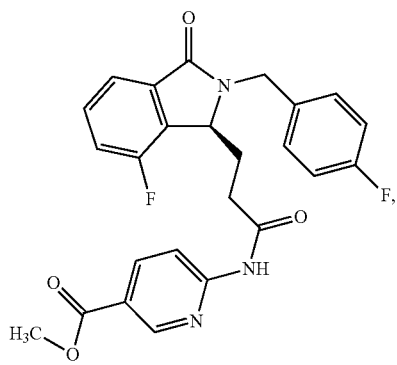
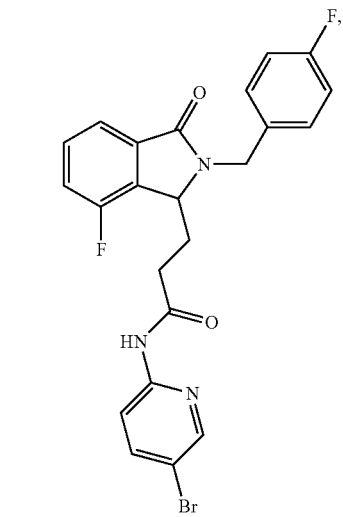
118
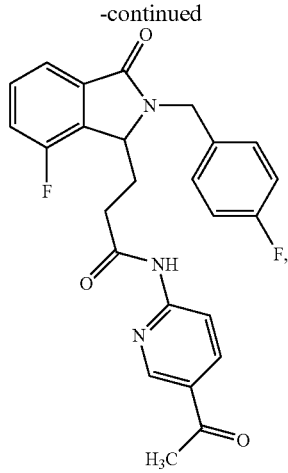
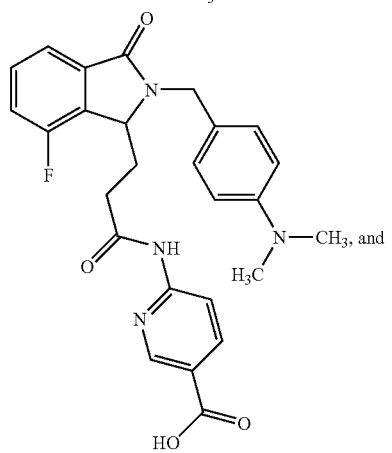
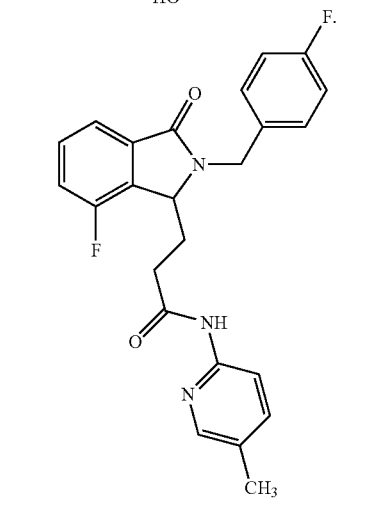
* * * * *